United States Patent
Wicha et al.

(10) Patent No.: US 10,557,850 B2
(45) Date of Patent: *Feb. 11, 2020

(54) ANTI-CXCR1 COMPOSITIONS AND METHODS

(71) Applicant: The Regents of The University of Michigan, Ann Arbor, MI (US)

(72) Inventors: Max S. Wicha, Ann Arbor, MI (US); Christophe Ginestier, Marseilles (FR)

(73) Assignee: THE REGENTS OF UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/566,436

(22) Filed: Dec. 10, 2014

(65) Prior Publication Data

US 2015/0094362 A1 Apr. 2, 2015

Related U.S. Application Data

(63) Continuation of application No. 12/616,579, filed on Nov. 11, 2009, now Pat. No. 8,940,301.

(Continued)

(51) Int. Cl.
*G01N 33/574* (2006.01)
*A61K 31/18* (2006.01)
(Continued)

(52) U.S. Cl.
CPC ....... *G01N 33/57492* (2013.01); *A61K 31/18* (2013.01); *A61K 31/337* (2013.01);
(Continued)

(58) Field of Classification Search
CPC . A61K 31/337; A61K 31/18; G01N 33/57415
See application file for complete search history.

(56) References Cited

U.S. PATENT DOCUMENTS 6,984,522 B2 1/2006 Clarke
7,115,360 B2 10/2006 Clarke
(Continued)

FOREIGN PATENT DOCUMENTS

CA 2417909 4/2002
CN 101014720 A 8/2007
(Continued)

OTHER PUBLICATIONS

Freund et al.; "IL-8 expression and its possible relationship with estrogen-receptor-negative status of breast cancer cells"; 2003; Oncogene; 22(3): 256-265.*

(Continued)

*Primary Examiner* — Timothy P Thomas
(74) *Attorney, Agent, or Firm* — Casimir Jones SC; David W. Staple

(57) ABSTRACT

The present invention provides methods of treating cancer by administering an IL8-CXCR1 pathway inhibitor (e.g., an anti-CXCR1 antibody or Repertaxin) alone or in combination with an additional chemotherapeutic agent such that non-tumorigenic and tumorigenic cancer cells in a subject are killed. The present invention also provides compositions and methods for detecting the presence of and isolating solid tumor stem cells in a patient (e.g., based on the presence of CXCR1 or FBXO21).

12 Claims, 30 Drawing Sheets

Related U.S. Application Data

(60) Provisional application No. 61/113,458, filed on Nov. 11, 2008.

(51) Int. Cl.
 A61K 31/337 (2006.01)
 A61K 45/06 (2006.01)

(52) U.S. Cl.
 CPC .......... A61K 45/06 (2013.01); G01N 33/574 (2013.01); G01N 33/5743 (2013.01); G01N 33/57407 (2013.01); G01N 33/57415 (2013.01); G01N 33/57434 (2013.01); G01N 33/57449 (2013.01); G01N 2333/7158 (2013.01)

(56) References Cited

U.S. PATENT DOCUMENTS

| | | | |
|---|---|---|---|
| 7,919,083 | B2 | 4/2011 | Lilard et al. |
| 8,940,301 | B2 | 1/2015 | Wicha et al. |
| 9,606,124 | B2 | 3/2017 | Wicha et al. |
| 2002/0147312 | A1 | 10/2002 | O'Keefe et al. |
| 2005/0142136 | A1 | 6/2005 | Suva et al. |
| 2007/0208074 | A1* | 9/2007 | Bonni .................. A61K 31/337 514/449 |
| 2007/0249672 | A1 | 10/2007 | Busch-Petersen |
| 2008/0178305 | A1 | 7/2008 | Clark et al. |
| 2008/0187938 | A1 | 8/2008 | Wicha |
| 2015/0160227 | A1 | 6/2015 | Wicha et al. |

FOREIGN PATENT DOCUMENTS

| | | |
|---|---|---|
| WO | 2003050502 | 6/2003 |
| WO | 2004045526 A2 | 6/2004 |
| WO | 2005005601 | 1/2005 |
| WO | 2005113534 A2 | 1/2005 |
| WO | 2005074633 | 8/2005 |
| WO | 2005103711 A2 | 11/2005 |
| WO | 2007053648 | 5/2007 |
| WO | 2008036419 A2 | 3/2008 |
| WO | 2010009121 A2 | 1/2010 |
| WO | WO2010056753 A1 | 5/2010 |

OTHER PUBLICATIONS

Slichenmyer et al.; "Taxol: a new and effective anti-cancer drug"; 1991; Anti-Cancer Drugs; 2:519-530.*
Patel et al.; "Paclitaxel sensitivity of breast cancer cells with constitutively active NF-κB is enhanced by IκBα super-repressor and parthenolide"; 2000 Oncogene; 19; 4159-4169.*
Sousa et al.; "The balance between the production of tumor necrosis factor-α and interleukin-10 determines tissue injury and lethality during intestinal ischemia and reperfusion"; 2005; Mem. Inst. Oswaldo Cruz, Rio de Janerio; 100(Suppl. I); 59-66.*
Waugh et al.; "The Interleukin-8 Pathway in Cancer"; Clin. Cancer Res.; Nov. 1, 2008; 14(21): 6735-6741.*
de la Iglesia et al.; "Identification of a PTEN-regulated STAT3 brain tumor suppressor pathway"; Feb. 7, 2008; Genes & Development ; 22:449-462; doi: 10.1101/gad.1606508 (Year: 2008).*
Mamot et al.; "Epidermal Growth Factor Receptor (EGFR)-targeted Immunoliposomes Mediate Specific and Efficient Drug Delivery to EGFR- and EGFRvIII-overexpressing Tumor Cells"; 2003; Cancer Research; 63:3154-3161 (Year: 2003).*
Peng et al. "Cross-talk between Epidermal Growth Factor Receptor and Hypoxia-inducible Factor-1α Signal Pathways Increases Resistance to Apoptosis by Up-regulating Survivin Gene Expression"; 2006; The Journal of Biological Chemistry; 281(36): 25903-25914 (Year: 2006).*
Freund et al.; "IL-8 expression and its possible relationship with estrogen-receptor-negative status of breast cancer cells"; 2003; Oncogene; 22(2): 256-265 (Year: 2003).*

Li et al., "Expression of Interleukin 8 and Its Receptors in Human Colon Carcinoma Cells with Different Metastatic Potential," clin Cancer Res, 2001, 7:3298-3304.
Li, et al. "Beyond tumorigenesis: cancer stem cells in metastasis" Cell Res. 2007; 17: 3-14.
Li, et al. "Identification of pancreatic cancer stem cells" Cancer Res. 2007; 67: 1030-1037.
Li, et al. "Intrinsic resistance of tumorigenic breast cancer cells to chemotherapy" J Natl. Cancer Inst. 100:672-679 (2008).
Luo, et al. "Mammary epithelial-specific ablation of the focal adhesion kinase suppresses mammary tumorigenesis by affecting mammary cancer stem/progenitor cells" Cancer Res. 69:466-474 (2009).
Luppi et al., "Interleukin-8 stimulates cell proliferation in non-smell lung cancer through epidermal growth factor receptor transactivation." Lung Cancer 2007, 56:25-33.
Matsuo et al., "CXCL8/IL-8 and CXCL12/SDF-1a Co0operatively Promote Invasiveness and Angiogenesis in Pacreatic Cancer." 2009 Int. J. Ca. 124:853-862.
Maxwell, et al. "HIF-1 and NF-kappaB-mediated upregulation of CXCR1 and CXCR2 expression promotes cell survival in hypoxic prostate cancer cells" Oncogene 2007; 26: 7333-7345.
Merritt et al., "Effect of Interleukin-8 Gene Silencing With Liposome-Encapsulated Small Interfering RNA on Ovarian Cancer Cell Grownth," J Natl Cancer Institute, 2008, 100:359-372.
Miller et al., "Expression of interleukin-8 receptors on tumor cells and vascular endothelial cells in human breast cancer tissue," Anticancer Res., 1998, 18:77-81.
Murphy, et al. "Nonapical and cytoplasmic expression of interleukin-8, CXCR1, and CXCR2 correlates with cell proliferation and microvessel density in prostate cancer" Clin. Cancer Res. 2005; 11: 4117-4127.
Phillips, et al. "The response of CD24(−/low)/CD44+ breast cancer-initiating cells to radiation" J Natl. Cancer Inst. 98:1777-1785 (2006).
Ponti, et al. "Isolation and in vitro propagation of tumorigenic breast cancer cells with stem/progenitor cell properties" Cancer Res. 2005; 65: 5506-5511.
Ramjeesingh et al., "Interleukin-8 secreted by Endothelial Cells induces chemotaxis of melanoma cells through the chemokine receptor CXCR1." FASEB J. 2003, 17:1292-4.
Reya, et al. "Stem cells, cancer, and cancer stem cells" Nature 414:105-111 (2001).
Ricci-Vitiani, et al. "Identification and expansion of human colon-cancer-initiating cells" Nature 2007; 445: 111-115.
Richards et al., "Coexpression of interleukin-8 receptors in head and neck squamous cell carcinoma," Am J Surg., 1997, 174:507-512.
Ringe, et al. "Towards in situ tissue repair: human mesenchymal stem cells express chemokine receptors CXCR1, CXCR2 and CCR2, and migrate upon stimulation with CXCL8 but not CCL2" J Cell Biochem. 2007; 101: 135-146.
Sansone, et al. "IL-6 triggers malignant features in mammospheres from human ductal breast carcinoma and normal mammary gland" J Clin.Invest 2007; 117: 3988-4002.
Schafer, et al. "IL-6 involvement in epithelial cancers" J Clin. Invest. 2007; 117: 3660-3663.
She et al., "Identification of side population cells from bladder cancer cells by DyeCycle Violet Staining," Cancer Biol Ther, 2008, 7:1663-1668.
Shibakura, et al. "Induction of IL-8 and monoclyte chemoattractant protein-1 by doxorubicin in human small cell lung carcinoma cells" 2003, Int. J. Can., 103:380-386.
Singh et al., "Small molecule antagonists for CXCR1 and CXCR2 inhibit tumor growth of human melanoma by decreasing cell proliferation and angiogenesis and enhancing apoptosis." 98th AACR Annual Meeting Apr. 14-18, 2007, Los Angeles, CA, 2 pages.
Slichenmyer & Von Hoff; "Taxol: a new and effective anti-cancer drug." Anticancer Drugs. Dec. 1991;2(6):519-30.
Song, et al. "Roles of Fas and Fas ligand during mammary gland remodeling" J Clin. Invest 106:1209-1220 (2000).

(56) References Cited

OTHER PUBLICATIONS

Souza, et al. "Reperlaxin, a novel inhibitor of rat CXCR2 function, inhibits inflammatory responses that follow intestinal ischaemia and reperfusion injury" Br J Pharmacol. 2004, vol. 143(1), p. 132-142.
Sugden & Holness, "Mechanisms underlying regulation of the expression and activities of the mammalian pyruvate dehydrogenase kinases." Arch Physiol Biochem. Jul. 2006;112(3):139-49.
Sutherland et al., "Characterization of a Hierarchy in Human Acute Myeloid Leukemia Progenitor Cells," Blood, 1996, 11:4754-4761.
Tamatani, et al. "Enhanced radiosensitization and chemosensitization in NF-kappaB-suppressed human oral cancer cells via the inhibition of gamma-irradiation- and 5-FU-induced production of IL-6 and IL-8" 2004, Int., J. Can., 108:912-921.
Todaro, et al. "Colon cancer stem cells dictate tumor growth and resist cell death by production of interleukin-4" Cell Stem Cell 2007; 1: 389-402.
Trentin, et al. "Multiple myeloma plasma cells show different chemokine receptor profiles at sites of disease activity" Br. J. Haematol. 2007; 138: 594-602.
Tsuruta et al., "Hyperplasia and Carcinomas in Pten-Deficient Mice and Reduced PTEN Protein in Human Bladder Cancer Patients," Cancer Res, 2006, 66:8389-8396.
Uslu, et al. "Predictive value of serum interleukin-8 levels in ovarian cancer patients treated with paclitaxel-containing regimens" 2005, Int. J. Gynecol. Cancer, 15:240-245.
Varney et al., "Expression of CXCR1 and CXCR2 receptors in malignant melanoma with different metastatic potential and their role in interleukin-8 (CXCL-8)-mediated modulation of metastatic phenotype," Clin & Eperimental Metastasis, 2003, 20:723-731.
Varney, et al. "Distinct expression of CXCL8 and its receptors CXCR1 and CXCR2 and their association with vessel density and aggressiveness in malignant melanoma" Am.J Clin. Pathol. 2006; 125: 209-216.
Varney, et al., "Small molecule antagonists for CXCR1 and CXCR2 inhibit human colon cancer metastasis by decreasing angiogenesis and enhancing apoptosis." 98 AACR Annual Meeting—Apr. 14-18, 2007, Los Angeles, CA, 2 pages.
Visvader, et al. "Cancer stem cells in solid tumours: accumulating evidence and unresolved questions" Nat. Rev. Cancer 8:755-768 (2008).
Vivanco, et al. "The phosphatidylinositol 3-Kinase AKT pathway in human cancer" Nat. Rev. Cancer 2:489-501 (2002).
Waugh, et al. "The interleukin-8 pathway in cancer" Clin. Cancer Res. 14:6735-6741 (2008).
Wicha, M. S., "The cancer stem cell hypothesis: Biological and clinical implications," AACR Annual Meeting 2008; San Diego, CA.
Xu, et al. "The focal adhesion kinase suppresses transformation-associated, anchorage-independent apoptosis in human breast cancer cells. Involvement of death receptor-related signaling pathways" J Biol. Chem. 275:30597-30604 (2000).
Yilmaz, et al. "Pten dependence distinguishes haematopoietic stem cells from leukaemia-initiating cells" Nature 441:475-482 (2006).
Yu, et al. "let-7 regulates self renewal and tumorigenicity of breast cancer cells" Cell 131:1109-1123 (2007).
Zhu et al., "Interleukin-8/CXCL8 is a growth factor for human lung cancer cells," British J of Cancer, 2004, 91:1970-1976.
Al Hajj, et al. "Prospective identification of tumorigenic breast cancer cells" Proc.Natl.Acad.Sci.U.S.A 2003; 100: 3983-3988.
Balbay, et al. "Highly metastatic human prostate cancer growing within the prostate of athymic mice overexpresses vascular endothelial growth factor" Clin.Cancer Res. 1999; 5: 783-789.
Bapat et al., "Stem and Progenitor-Like Cells contribute to the Aggressive Behaviour or Human Epithelial Ovarian Cancer," Cancer Res, 2005, 65:3025-3029.
Bates et al., "The epithelial-mesenchymal transition of colon carcinoma involves expression of IL-8 and CXCR-1-mediated chemotaxis." Experimental Cell Research Oct. 2004, 299(2):315-324

Beech, et al. "The MHP36 line of murine neural stem cells expresses functional CXCR1 chemokine receptors that initiate chemotaxis in vitro" J Neuroimmunol. 184:198-208 (2007).
Bertini, et al. "Noncompetitive allosteric inhibitors of the inflammatory chemokine receptors CXCR1 and CXCR2: prevention of reperfusion injury" Proc. Natl. Acad. Sci. U. S A 101:11791-11796 (2004).
Bizzarri et al. "ELR+ CXC chemokines and their receptors (CXC chemokine receptor 1 and CXC chemokine receptor 2) as new therapeutic targets." Pharmacol Ther. Oct. 2006; 112(1):139-49.
Bonnet, et al. "Human acute myeloid leukemia is organized as a hierarchy that originates from a primitive hematopoietic cell" Nat.Med. 1997; 3: 730-737.
Brunet, et al. "Protein kinase SGK mediates survival signals by phosphorylating the forkhead transcription factor FKHRL1 (FOXO3a)" Mol. Cell Biol. 21:952-965 (2001).
Casilli et al., "Inhibition of interleukin-9 (CXCL8/IL-8) responses by repertaxin, a new inhibitor of the cheokine receptors CXCR1 and CXCR2." Biochemical Pharmacology 2005, 69: 385-394.
Charafe-Jauffret, et al. "Breast cancer cell lines contain functional cancer stem cells with metastatic capacity and a distinct molecular signature" Cancer Res. 69:1302-1313 (2009).
Chhipa, et al. "Bystander killing of breast cancer MCF-7 cells by MDA-MB-231 cells exposed to 5-fluorouracil is mediated via Fas" J Cell Biochem. 101:68-79 (2007).
Collins et al., "Prospective Identification of Tumorigenic Prostate Cancer Stem Cells," Cancer Res., 2005, 65:10946-10951.
Collins, et al. "Paclitaxel up-regulates interleukin-8 synthesis in human lung carcinoma through an NF-kappaB- and AP-1-dependent mechanism" 2000, Can. Imm. Immuno., 49:78-84.
Croker, et al. "High aldehyde dehydrogenase and expression of cancer stem cell markers selects for breast cancer cells with enhanced malignant and metastatic ability" J Cell Mol Med. Aug. 4, 2008 (e-pub ahead of print) J. Cell. Mol. Med. vol. 13, No. 8B, 2009 pp. 2236-2252.
De Larco, et al. "Progression and enhancement of metastatic potential after exposure of tumor cells to chemotherapeutic agents" 2001, Can. Res. 61:2857-2861.
Dontu , et al. "In vitro propagation and transcriptional profiling of human mammary stem/progenitor cells" Genes Dev. 2003; 17: 1253-1270.
Dubrovska, et al. "The role of PTEN/Akt/PI3K signaling in the maintenance and viability of prostate cancer stem-like cell populations" Proc. Natl. Acad. Sci. U. S A 106:268-273 (2009).
Eramo et al., "Identification and expansion of the tumorigenic lung cancer stem cell population," Cell Death and Differentiation, 2008, 15:504-514.
Fang et al., "A Tumorigenic Subpopulation with Stem Cell Properties in Melanomas," Cancer Res, 2005, 65:9328-9337.
Fillmore et al., "Human breast cancer cell lines contain stem-like cells that self-renew, give rise to phenotypically diverse progeny and survive chemotherapy," Breast Cancer Research, 2008, 10:R25(doi:10.1186/bcr1982).
Freund,et al. "IL-8 expression and its possible relationship with estrogen-receptor-negative status of breast cancer cells" Oncogene 2003; 22: 256-265.
Ginestier et al., "CXCR1 blockade selectively targets human barest cancer stem cells in vitro and in xenografts," J Clin Invest doi:10.1172/JCI39397.
Ginestier et al., "The IL8/CXCR1 axis regulates breast carcinoma stem cells," Abstract, Presented at AACR Annual Meeting, Apr. 12-16, 2008.
Ginestier, et al. "ALDH1 Is a Marker of Normal and Malignant Human Mammary Stem Cells and a Predictor of Poor Clinical Outcome" Cell Stem Cell 2007; 1: 555-567.
Glinsky "Stem cell origin of death-from-cancer phenotypes of human prostate and breast cancers" Stem Cell Rev. 2007; 3: 79-93.
Glinsky, et al. "Microarray analysis identifies a death-from-cancer signature predicting therapy failure in patients with multiple types of cancer" J Clin.Invest 2005; 115: 1503-1521.

(56) References Cited

OTHER PUBLICATIONS

Grimsditch, et al. "C3H apoE(−/−) mice have less atherosclerosis than C57BL apoE(−/−) mice despite having a more atherogenic serum lipid profile" Atherosclerosis. Aug. 2000, vol. 151(2), pp. 389-397 (formerly Benson).
Gupta, et al. "ID genes mediate tumor reinitiation during breast cancer lung metastasis" Proc.Natl.Acad.Sci.U.S.A 2007; 104: 19506-19511.
Hambardzumyan, et al. "Cancer stem cells and survival pathways" Cell Cycle 2008; 7, pp. 1371-1378.
Harper et al., "Stem Cell Patterns in Cell Lines Derviced from Head and Neck Squamous Cell Carcinoma," J Oral Pathol Med, 2007, 36:594-603.
Hjortoe et al., "Tissue factor-factor VIIa-specific up-regulation of IL-8 expression in MDA-MB-231 cells is mediated by PAR-2 and results in increased cell migration." Blood. Apr. 15, 2004; 103(8):3029-37.
Hollestelle, et al. "Phosphatidylinositol-3-OH kinase or RAS pathway mutations in human breast cancer cell lines" Mol. Cancer Res. 5:195-201, 2007.
Huang et al., "Fully Humanized Neutralizing Antibodies to Interleukin-8 (ABX-IL8) Inhibit Angiogenesis, Tumor Growth, and Metastasis of Human Melanoma." American Journal of Pathology Jul. 2002, 161(1): 125-134.
Huang et al., "Isolation and Identification of cancer stem-like cells in esophageal carcinoma cell lines," Stem Cells Dev., 2009, 18:465-473.
Hughes, et al. "Characterisation of breast cancer cell lines and establishment of a novel isogenic subclone to study migration, invasion gration, and tumourigenicity" Clin.Exp.Metastasis, 2008, vol. 25, pp. 549-557.
Inoue, et al. "Interleukin 8 expression regulates tumorigenicity and metastases in androgen-independent prostate cancer" Clin. Cancer Res. 2000; 6: 2104-2119.
Itoh, et al. "IL-8 promotes cell proliferation and migration through metalloproteinase-cleavage proHB-EGF in human colon carcinoma cells." Cytokine 2005; 29: 275-282.
Jagani, et al. "Cancer stem cells and impaired apoptosis" Adv. Exp. Med. Biol. 2008; 615: 331-344.
Jaiswal, et al. "Expression of BCR/ABL and BCL-2 in myeloid progenitors leads to myeloid leukemias" Proc. Natl. Acad. Sci. USA, 2003; 100: 10002-10007.
Jonsson, et al. "Inflammatory arthritis requires Foxo3a to prevent Fas ligand-induced neutrophil apoptosis" Nat. Med. 11:666-671 (2005).
Jordan, "Cancer stem cell biology: from leukemia to solid tumors." Curr Opin Cell Biol. Dec. 2004; 16(6):708-12.
Karnoub, et al. "Mesenchymal stem cells within tumour stroma promote breast cancer metastasis" Nature 2007; 449: 557-563.
Kim, et al. "Expression of interleukin-8 correlates with angiogenesis, tumorigenicity, and metastasis of human prostate cancer cells implanted orthotopically in nude mice" Neoplasia. 2001; 3: 33-42.
Korkaya, et al. "Regulation of Mammary Stem/Progenitor Cells by PTEN/Akt/β-Catenin Signaling" PLoS Biolog. 7: e1000121.
Krivtsov, et al. "Transformation from committed progenitor to leukaemia stem cell initiated by MLL-AF9" Nature 2006; 442: 818-822.
Kurenova, et al. "Focal adhesion kinase suppresses apoptosis by binding to the death domain of receptor-interacting protein" Mol. Cell Biol. 24:4361-4371 (2004).
Landi, et al. "Interleukin-4 and interleukin-4 receptor polymorphisms and colorectal cancer risk" Eur.J Cancer 2007; 43: 762-768.
Lev, et al. "Dacarbazine causes transcriptional up-regulation of interleukin 8 and vascular endothelial growth factor in melanoma cells: a possible escape mechanism from chemotherapy" 2003, Mol. Can. Ther., 2:753-763.
Levina, et al. "Drug-Selected Human Lung Cancer Stem Cells: Cytokine Network, Tumorigenic and Metastatic Properties" PLoS ONE. 3:e3077.
Bendre et al. "Expression of Interleukin 8 and not Parathyroid Hormone-related Protein by Human Breast Cancer Cells Correlates with Bone Metastasis in Vivo", Cancer Res., 2002, 62: 5571-5579.
Bendre et al. "Tumor-derived interleukin-8 stimulates osteolysis independent of the receptor activator of nuclear factor-kappaB ligand pathway", 2005, Cancer Res., 2005, 65(23): 11001-9.
Campbell et al., "Models of bone metastasis," 2012, J. Vis. Exp. 67: e4260.
Iglesia et al. "STAT3 regulation of glioblastoma pathogenesis", Curr. Mol. Med., 2009, 9(5): 580-90.
Iglesia et al. "Identification of a PTEN-regulated STAT3 brain tumor suppressor pathway", Genes Dev., 2008, 22(4): 449-62.
Iglesia et al. "Deregulation of a STAT3-interleukin 8 signaling pathway promotes human glioblastoma cell proliferation and invasiveness", J Neurosci. Jun. 4, 2008;28(23):5870-8.
International Preliminary Report on Patentability for WO/2010056753 dated May 17, 2011, 8 pages.
International Search Report for WO2010056753 dated Jan. 26, 2010, 8 pages.
Ling and Arlinghaus. "Knockdown of STAT3 expression by RNA interference inhibits the induction of breast tumors in immunocompetent mice", Cancer Res. 2005, 65(7): 2532-6.
Yao et al., "Interleukin-8 modulates growth and invasiveness of estrogen receptor-negative breast cancer cells", Int. J. Cancer, 2007, 121(9): 1949-57.
Sharma et al., 2013, "Targeting CXCR2 Enhances Chemotherapeutic Response, Inhibits Mammary Tumor Growth, Angiogenesis, and Lung Metastasis", Molecular Cancer Therapeutics, 12(5): 799-808.
Li et al., 2006, "Enhancement of antitumor activity of the anti-EGF receptor monoclonal antibody cetuximab/C225 by perifosine in PTEN-deficient cancer cells", Oncogene, 25(4): 525-535.
Lu et al., 1999, "The PTEN/MMAC1/TEP tumor suppressor gene decreases cell growth and induces apoptosis and anoikis in breast cancer cells", Oncogene, 18(50):7034-7045.
Brandolini et al., 2015, "Targeting CXCR1 on breast cancer stem cells: signaling pathways and clinical application modelling", Oncotarget, vol. 6, No. 41: 43375-43394.
Chang et al., Monolayer and spheroid culture of human liver hepatocellular carcinoma cell line cells demonstrate distinct global gene expression patterns and functional phenotypes. Tissue Eng Part A., 15(3):559-67 (2009).
Grimshaw et al., Mammosphere culture of metastatic breast cancer cells enriches for tumorigenic breast cancer cells.Breast Cancer Res., 10(3): R52 (2008).
Hirose et al., Chemokine gene transfection into tumour cells reduced tumorigenicity in nude mice in association with neutrophilic infiltration. Br J Cancer., 72(3):708-14 (1995).
Kamohara et al., Regulation of tumour necrosis factor-related apoptosis-inducing ligand (TRAIL) and TRAIL receptor expression in human neutrophils. Immunology., 111(2): 186-194 (2004).
Morrison et al., Breast cancer stem cells: implications for therapy of breast cancer. Breast Cancer Res., 10(4): 210 (2008).
Tagaki et al., Three-dimensional Cellular Spheroid Formation Provides Human Prostate Tumor Cells with Tissue-like Features. Anticancer Research, 27: 45-54 (2007).
Wang et al., TNFalpha resistance in MCF-7 breast cancer cells is associated with altered subcellular localization of p21CIP1 and p27KIP1. Cell Death Differ., 12(1):98-100 (2005).
Patel, N. et al. "Paclitaxel sensitivity of breast cancer cells with constitutively active NF-κB is enhanced by IκBα super-repressor and parthenolide" Oncogene vol. 19, pp. 4159-4169 (2000).
Souza, D. et al. "The balance between the production of tumor necrosis factor-a and interleukin-10 determines tissue injury and lethality during intestinal ischemia and reperfusion" Mem Inst Oswaldo Cruz, Rio de Janeiro, vol. 100 (Suppl. 1) 59-66, 2005.
Waugh, D. et al. "The Interleukin-8 Pathway in Cancer" Molecular Pathways, Clin Cancer Res 2008; 14(21) Nov. 1, 2008, 6735-6741.
Bowman et al., STATs in oncogenesis. Oncogene. May 15, 2000;19(21):2474-88.
Bromberg et al., Stat3 as an oncogene. Cell. Aug. 6, 1999;98(3):295-303.
Cavalieri et al., Neutrophil Recruitment in the Reperfused—Injured Rat Liver Was Effectivelyattenuated by Repertaxin, A NovelaI-

(56) References Cited

OTHER PUBLICATIONS losteric Noncompetitive Inhibitor of CXCL8 Receptors: Atherapeutic Approach for the Treatment of Post-Ischemic Hepatic Syndromes. Intl J Immuno Pharma; 2005;18(3)475-86.

Chau et al., Development of a STAT3 reporter prostate cancer cell line for high throughput screening of STAT3 activators and inhibitors. Send to Biochem Biophys Res Cornmun. Dec. 12, 2008;377(2):627-631.

Garcia et al., Constitutive activation of Stat3 in fibroblasts transformed by diverse oncoproteins and in breast carcinoma cells. Cell Growth Differ. Dec. 1997;8(12):1267-76.

Hirose et al., Chemokine gene transfection into tumour cells reduced tumorigenicity in nude mice in association with neutrophilic infiltration. Br J Cancer. Sep. 1995;72(3):708-14.

Hojilla et al., Inflammation and breast cancer: metalloproteinases as common effectors of inflammation and extracellular matrix breakdown in breast cancer. Breast Cancer Res. 2008;10(2):205.

Kamohara et al., Regulation of tumour necrosis factor-related apoptosis-inducing ligand (TRAIL) and TRAIL receptor expression in human neutrophils. Immunology. Feb. 2004;111(2):186-94.

Lee et al., IL-8 reduced tumorigenicity of human ovarian cancer in vivo due to neutrophil infiltration. J Immunol. Mar. 1, 2000;164(5):2769-75.

Leitner et al., Reparixin, a Specific Interleukin-8 Inhibitor, Has no Effects on Inflammation During Endotoxemia. Intl J Immuno Pharma 2007;20(1):25-36.

Ling et al., Knockdown of STAT3 expression by RNA interference inhibits the induction of breast tumors in immunocompetent mice. Cancer Res. Apr. 1, 2005;65(7):2532-6.

Rae et al., EGFR and EGFRvIII expression in primary breast cancer and cell lines, Breast Cancer Research and Treatment 2004;87:87-95.

Raman et al., Role of chemokines in tumor growth. Cancer Lett. Oct. 28, 2007;256(2):137-65.

Reparixin in Prevention of Delayed Graft Dysfunction After Kidney Transplantation. ClinicalTrials.gov Identifiier NCT00248040. First posted Nov. 3, 2005. Retrieved from www.clinicaltrials.gov/ct2/show/record/NCT00248040?TERM=NCT00248040. Retrieved Oct. 1, 2018. 7 pages.

Yao et al., Interleukin-8 modulates growth and invasiveness of estrogen receptor-negative breast cancer cells. Int J Cancer. Nov. 1, 2007;121(9):1949-57.

\* cited by examiner

B.

A.

ANTI-CXCR1 COMPOSITIONS AND METHODS

CROSS-REFERENCE TO RELATED APPLICATIONS

The present application is a continuation of U.S. patent application Ser. No. 12/616,579, filed Nov. 11, 2009, which claims priority to U.S. Provisional Patent Application No. 61/113,458, filed Nov. 11, 2008, each of which are hereby incorporated by reference in its entirety.

STATEMENT REGARDING FEDERALLY SPONSORED RESEARCH OR DEVELOPMENT

This invention was made with government support under CA129765, CA101860 and CA046592 awarded by the National Institutes of Health. The government has certain rights in the invention.

FIELD OF THE INVENTION

The present invention provides methods of treating cancer by administering an IL8-CXCR1 pathway inhibitor (e.g., an anti-CXCR1 antibody or Repertaxin) alone or in combination with an additional chemotherapeutic agent such that non-tumorigenic and tumorigenic cancer cells in a subject are killed. The present invention also provides compositions and methods for detecting the presence of and isolating solid tumor stem cells in a patient (e.g., based on the presence of CXCR1 or FBXO21).

BACKGROUND

Cancer remains the number two cause of mortality in this country, resulting in over 500,000 deaths per year. Despite advances in detection and treatment, cancer mortality remains high. Despite the remarkable progress in understanding the molecular basis of cancer, this knowledge has not yet been translated into effective therapeutic strategies.

In particular, breast cancer is the most common cancer in American women, with approximately one in nine women developing breast cancer in their lifetime. Unfortunately, metastatic breast cancer is still an incurable disease. Most women with metastatic breast cancer succumb to the disease.

Traditional modes of therapy (radiation therapy, chemotherapy, and hormonal therapy), while useful, have been limited by the emergence of treatment-resistant cancer cells. Clearly, new approaches are needed to identify targets for treating metastatic breast cancer and cancer generally.

SUMMARY OF THE INVENTION

The present invention provides methods of treating cancer by administering an IL8-CXCR1 pathway inhibitor (e.g., an anti-CXCR1 antibody or Repertaxin) alone or in combination with an additional chemotherapeutic agent such that non-tumorigenic and tumorigenic cancer cells in a subject are killed. The present invention also provides compositions and methods for treating and diagnosing the presence of solid tumor stem cells in a patient (e.g., based on the presence of CXCR1 or FBXO21).

In some embodiments, the present invention provides methods of treating cancer comprising: administering an IL8-CXCR1 pathway antagonist and an additional chemotherapeutic agent to a subject. In certain embodiments, the present invention provides methods of reducing or eliminating cancer stem cells and non-tumorigenic cancer cells in a subject comprising: administering Repertaxin or derivative thereof to a subject under conditions such that at least a portion of the cancer stem cells and at least a portion of the non-tumorigenic cancer cells are killed. In other embodiments, the present invention provides methods of reducing or eliminating cancer stem cells and non-tumorigenic cancer cells in a subject comprising: administering an IL8-CXCR1 pathway antagonist and an additional chemotherapeutic agent to a subject under conditions such that at least a portion of the cancer stem cells and at least a portion of the non-tumorigenic cancer cells are killed. In particular embodiments, the present invention provides compositions or kits comprising an IL8-CXCR1 pathway antagonist and an additional chemotherapeutic agent.

In certain embodiments, the IL8-CXCR1 pathway antagonist comprises an agent that specifically blocks the binding of IL8 to CXCR1. In some embodiments, the agent binds to (is specific for) CXCR1, but does not bind to CXCR2. In other embodiments, the agent binds to CXCR1. In particular embodiments, the agent comprises an anti-CXCR1 antibody or antibody fragment. In additional embodiments, the agent comprises Repertaxin or a derivative thereof. In further embodiments, the additional chemotherapeutic agent comprises an anti-mitotic compound. In certain embodiments, the anti-mitotic compound is selected from the group consisting of: docetaxel, doxorubicin, paclitaxel, fluorouracil, vincristine, vinblastine, nocodazole, colchicine, podophyllotoxin, steganacin, and combretastatin. In other embodiments, the anti-mitotic compound is a catharalthus alkaloids (e.g., vincristine and vinblastine); or a benzimidazole carbamates such as nocodazole; or colchicine or related compounds such as podophyllotoxin, steganacin or combretastatin; or a taxane such as paclitaxel and docetaxel. In certain embodiments, the additional chemotherapeutic agent comprises docetaxel.

In particular embodiments, the subject has a type of cancer that, when treated with a chemotherapeutic, has increased levels of IL-8 production (e.g., which causes an increase in cancer stem cell number of motility). In some embodiments, the subject has a type of cancer selected from the group consisting of: prostate cancer, ovarian cancer, breast cancer, melanoma, non-small cell lung cancer, small-cell lung cancer, and esophageal adenocarcinoma.

In other embodiments, the present invention provides methods of detecting solid tumor stem cells comprising; a) providing: i) a sample taken from a tumor of a subject, and ii) an antibody, or antibody fragment (or other binding molecule), specific for the CXCR1 protein or FBXO21 protein (or another protein from Table 1); and b) contacting the tissue sample with the antibody, or antibody fragment, under conditions such that the presence or absence of CXCR1+ or FBXO21+ solid tumor stem cells are detected.

In particular embodiments, the antibody, or antibody fragment, is conjugated to a signal molecule. In further embodiments, the signal molecule comprises a fluorescent molecule. In other embodiments, the signal molecule comprises an enzyme that can catalyze a color producing reaction in the presence of a colorimetric substrate. In certain embodiments, the method further comprises contacting the sample with a secondary antibody, or secondary antibody fragment, specific for the antibody or antibody fragment. In other embodiments, the secondary antibody, or secondary antibody fragment, comprises a signal molecule. In particular embodiments, no other proteins or nucleic acids are assayed in order to determine the presence or absence of the CXCR1 or FBXO21+ solid tumor stem cells. In additional embodiments, the tumor is selected from the group consisting of: a prostate cancer tumor, an ovarian cancer tumor, a breast cancer tumor, a melanoma, a non-small cell lung cancer tumor, a small-cell lung cancer tumor, and an esophageal adenocarcinoma tumor.

In some embodiments, the present invention provides methods of enriching for a population of solid tumor stem cells comprising: a) disassociating a solid tumor to generate disassociated cells; b) contacting the disassociated cells with a reagent that binds CXCR1 or FBXO21 (or other protein from Table 1); and c) selecting cells that bind to the reagent under conditions such that an a population enriched for solid tumor stem cells is generated.

In certain embodiments, no additional reagents are employed in order to generate the population enriched for solid tumor stem cells. In some embodiments, the tumor is selected from the group consisting of: a prostate cancer tumor, an ovarian cancer tumor, a breast cancer tumor, a melanoma, a non-small cell lung cancer tumor, a small-cell lung cancer tumor, and an esophageal adenocarcinoma tumor. In further embodiments, the reagent is an antibody or antibody fragment (e.g., Fab fragment). In additional embodiments, the reagent is conjugated to a fluorochrome or magnetic particles. In other embodiments, the selecting cells is performed by flow cytometry, fluorescence activated cell sorting, panning, affinity column separation, or magnetic selection.

In particular embodiments, the present invention provides an enriched population of solid tumor stem cells isolated by the methods described herein.

In some embodiments, the present invention provides isolated populations of cancer stem cells that are: a) tumorigenic; and b) CXCR1+ or FBXO21+. In certain embodiments, the cancer stem cells are cancer stem cells selected from the group consisting of: prostate cancer stem cells, ovarian cancer stem cells, breast cancer stem cells, skin cancer stem cells, non-small cell lung cancer stem cells, small-cell lung cancer stem cells, and esophageal adenocarcinoma stem cells. In other embodiments, the population comprises at least 60% cancer stem cells and less than 40% non-tumorigenic tumor cells. In further embodiments, the cancer stem cells: are enriched at least two-fold compared to unfractionated non-tumorigenic tumor cells (e.g., 2-fold, 3-fold, 4-fold, 5-fold, . . . , 10-fold, . . . 100-fold, . . . 1000-fold).

In some embodiments, the present invention provides methods for obtaining from a tumor a cellular composition comprising cancer stem cells and non-tumorigenic tumor cells, wherein at least 60% are tumorigenic stem cells and 40% or less are non-tumorigenic tumor cells, the method comprising: a) obtaining a dissociated mixture of tumor cells from a tumor; b) separating the mixture of tumor cells into a first fraction comprising at least 60% cancer stem cells and 40% or less non-tumorigenic tumor cells and a second fraction of tumor cells depleted of cancer stem cells wherein the separating is by contacting the mixture with a reagent against CXCR1 or FBXO21; and c) demonstrating the first fraction to be tumorigenic by: i) serial injection into a first host animal and the second fraction to be non-tumorigenic by serial injection into a second host animal. In certain embodiments, the separating is performed by flow cytometry, fluorescence activated cell sorting (FACS), panning, affinity chromatography or magnetic selection. In some embodiments, the separating is performed by fluorescence activated cell sorters (FACS) analysis.

In particular embodiments, the present invention provides methods for selecting a treatment for a patient having a solid tumor, comprising: (a) obtaining a sample from the patient; (b) identifying the presence of CXCR1+ or FBXO21+ solid tumor stem cell in the sample; and (c) selecting a treatment for the patient that targets CXCR1+ or FBXO21+ solid tumor stem cells (e.g., selecting the use of an anti-CXCR1 antibody or antibody fragment). In certain embodiments, the CXCR1+ or FBXO21+ solid tumor stem cells are cancer stem cells selected from the group consisting of: prostate cancer stem cells, ovarian cancer stem cells, breast cancer stem cells, skin cancer stem cells, non-small cell lung cancer stem cells, small-cell lung cancer stem cells, and esophageal adenocarcinoma stem cells.

In some embodiments, the present invention provides methods for screening a compound, comprising: a) exposing a sample comprising a CXCR1+ or FBXO21+ cancer stem cell to a candidate anti-neoplastic compound, wherein the candidate anti-neoplastic compound comprises a CXCR1 or FBXO21 antagonist or a IL8-CXCR1 signaling pathway antagonist; and b) detecting a change in the cell in response to the compound.

In certain embodiments, the sample comprises a non-adherent mammosphere. In further embodiments, the CXCR1 or FBXO21 antagonist, or IL8-CXCR1 signaling pathway antagonist comprises an antibody or antibody fragment. In some embodiments, the CXCR1 antagonist is a derivative of Repartaxin. In other embodiments, the detecting comprises detecting cell death of the tumorigenic breast cell. In further embodiments, the methods further comprise identifying the candidate anti-neoplastic agent as capable of killing tumorigenic cells as well as non-tumorigenic cancer cells.

In some embodiments, the present invention provides methods for determining the capability of a test compound to inhibit tumorigenesis of solid tumor stem cells comprising: a) obtaining enriched solid tumor stem cells, wherein the solid tumor stem cells: i) are enriched at least two-fold compared to unfractionated tumor cells; and ii) express CXCR1 or FBXO21; b) exposing a first set, but not a second set, of the solid tumor stem cells to a test compound; c) injecting the first set of the solid tumor stem cells into a first host animal and injecting the second set of solid tumor stem cells into a second host animal; and d) comparing a tumor, if present, in the first animal with a tumor formed in the second animal in order to determine if the test compound inhibits tumor formation. In particular embodiments, the test compound is a CXCR1 or FBXO21 inhibitor, or a IL8-CXCR1 inhibitor pathway inhibitor.

In further embodiments, the present invention provides methods for determining the capability of a test compound to inhibit tumorigenesis of solid tumor stem cells comprising: a) obtaining a sample comprising at least 60% solid tumor stem cells, wherein the solid tumor stem cells express CXCR1 or FBXO21; b) injecting the solid tumor stem cells into first and second host animals; c) treating the first host animal with a test compound, and not treating the second host animal with the test compound; and d) comparing a tumor, if present, in the first animal with a tumor formed in the second animal in order to determine if the test compound inhibits tumor formation. In other embodiments, the test compound is a CXCR1 or FBXO21 inhibitor or an IL8-CXCR1 pathway inhibitor.

have cancer stem cell properties. A-B, G-H. Representative flow cytometry analysis of ALDH enzymatic activity in MDA-MB-453 (A-B) and SUM159 cells (G-H). The ALDEFLUOR assay was performed as described in Example 1 below. (C, I) The ALDEFLUOR-positive population was capable of generating tumors in NOD/SCID mice which recapitulated the phenotypic heterogeneity of the initial tumor. (F, L) Tumor growth curves were plotted for different numbers of cells injected (for MDA-MB-453: 50,000 cells, 5,000 cells, and 500 cells and for SUM159: 100,000 cells, 10,000 cells, and 1,000 cells) and for each population (ALDEFLUOR-positive, ALDEFLUOR-negative, unseparated). Tumor growth kinetics correlated with the latency and size of tumor formation and the number of ALDEFLUOR-positive cells (F, L). (D, J) H&E staining of ALDEFLUOR-positive cells' injection site, revealing presence of tumor cells (D: MDA-MB-453 ALDEFLUOR-positive cells' injection site, and J: SUM59 ALDEFLUOR-positive cells' injection site). (E, K) The ALDEFLUOR-negative cells' injection site contained only residual Matrigel, apoptotic cells, and mouse tissue (E: MDA-MB-453 ALDEFLUOR-negative cells' injection site, and K: SUM59 ALDEFLUOR-negative cells' injection site). Data represent mean±SD.

Figure 2:
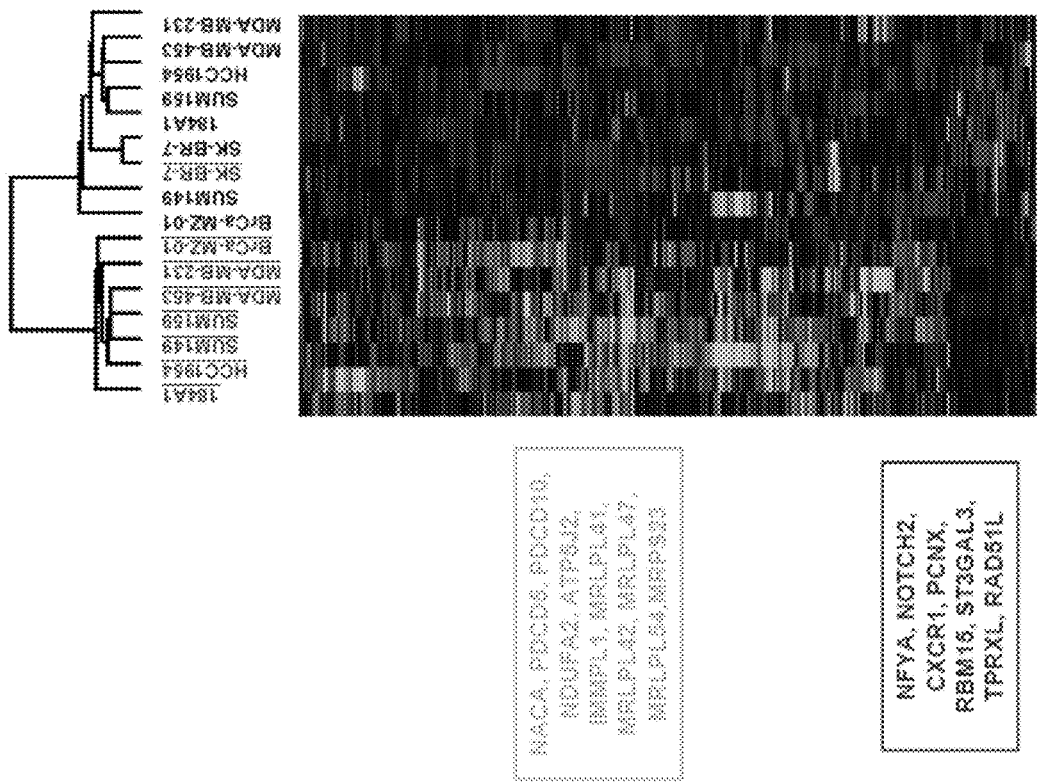

FIG. 2 shows classification of the ALDEFLUOR-positive and ALDEFLUOR-negative populations isolated from breast cell lines based on the "cancer stem cell signature". FIG. 2A. Hierarchical clustering of 16 samples based on a 413-gene expression signature. Each row of the data matrix represents a gene and each column represents a sample. Note the separation between ALDEFLUOR-positive (underlined names) and negative samples (non-underlined names) with the 413 genes for 15 out of the 16 samples. Some genes included in the signature are referenced by their HUGO abbreviation as used in 'Entrez Gene' (Genes down-regulated in the ALDEFLUOR-positive populations are labeled in green and genes up-regulated in the ALDEFLUOR-positive populations are labeled in red). FIG. 2B-C. To confirm the gene expression results, in a set of five breast cancer cell lines sorted for the ALDEFLUOR phenotype, the expression of five discriminator genes overexpressed in ALDEFLUOR-positive populations (CXCR1/IL8RA, FBXO21, NFYA, NOTCH2 and RAD51L1) were measured by quantitative RT-PCR. The quantitative RT-PCR expression levels of CXCR1 and FBXO21 are presented in this figure. Gene expression levels measured by quantitative RT-PCR confirm the results obtained using DNA microarrays with an increase of CXCR1 and FBXO21 mRNA level in the ALDEFLUOR-positive population compared to the ALDEFLUOR-negative population ($p<0.05$).

Figure 3:
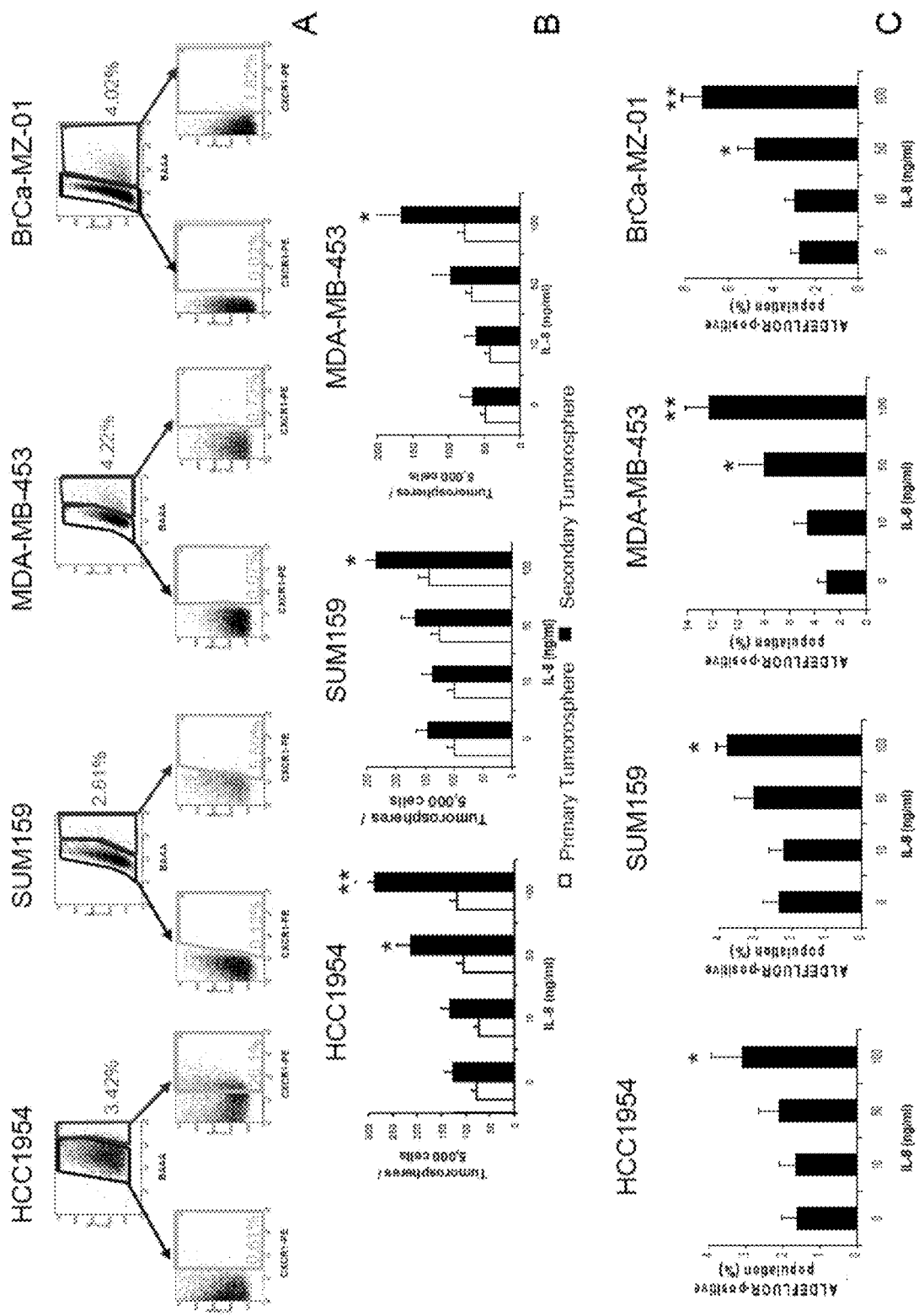

FIG. 3 shows the role of the IL8/CXCR1 axis in the regulation of breast cancer stem cells. A. Cells expressing CXCR1 are contained in the ALDEFLUOR-positive population. The ALDEFLUOR-positive and -negative population from four different breast cell lines (HCC1954, SUM159, MDA-MB-453, BrCa-MZ-01) were isolated by FACS, fixed, and analyzed for the expression of CXCR1 protein by immunostaining and FACS analysis. ALDEFLUOR-positive cells were highly enriched in CXCR1-positive cells compared to the ALDEFLUOR-negative population. B. Effect of IL8 treatment on tumorosphere formation of three different cell lines (HCC1954, SUM159, MDA-MB-453). IL8 treatment increased the formation of primary and secondary tumorospheres in a dose-dependent manner. C. Effect of IL8 treatment on the ALDEFLUOR-positive population of four different cell lines cultured in adherent conditions. IL8 increased the ALDEFLUOR-positive population in a dose-dependent manner in each of the four cell lines analyzed (* $p<0.05$/** $p<0.01$, statistically significant differences from the control group).

Figure 4:
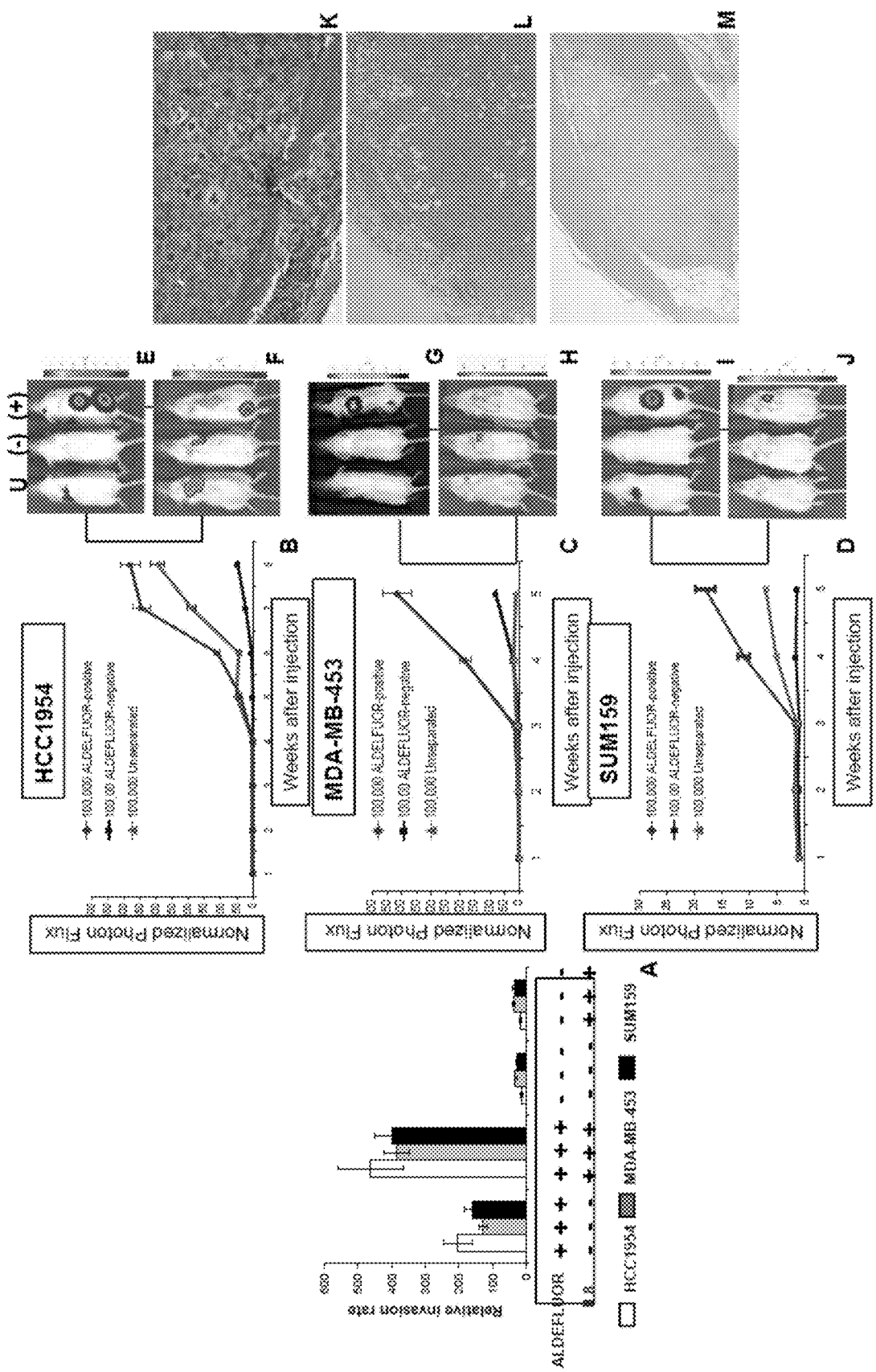

FIG. 4 shows ALDEFLUOR-positive cells display increased metastatic potential. A. The IL8/CXCR1 axis is involved in cancer stem cell invasion. The role of the IL8/CXCR1 axis in invasion was assessed by a Matrigel invasion assay using serum or IL8 as attractant for three different cell lines (HCC1954, MDA-MB-453, SUM159). ALDEFLUOR-positive cells were 6- to 20-fold more invasive than ALDEFLUOR-negative cells ($p<0.01$). When using IL8 (100 ng/ml) as attractant, it was observed that a significant increase of ALDEFLUOR-positive cells were invading through Matrigel compared to serum as attractant ($p<0.05$). In contrast IL8 had no effect on the invasive capacity of the ALDEFLUOR-negative population. B-M. The ALDEFLUOR-positive population displayed increased metastatic potential. B-D. Quantification of the normalized photon flux measured at weekly intervals following inoculation of 100,000 luciferase infected cells from each group (ALDEFLUOR-positive, ALDEFLUOR-negative, unseparated). E-J Detection of metastasis utilizing the bioluminescence imaging software (E, G, I: Mice facing down; F, H, J: Mice facing up). Mice inoculated with ALDEFLUOR-positive cells developed several metastasis localized at different sites (bone, muscle, lung, soft tissue) and displayed a higher photon flux emission than mice inoculated with unseparated cells, which developed no more than one metastasis per mouse. In contrast, mice inoculated with ALDEFLUOR-negative cells developed only an occasional small metastasis, which was limited to lymph nodes. K-M. Histologic confirmation, by H&E staining, of metastasis in bone (K), soft tissue (L) and muscle (M) resulting from injection of ALDEFLUOR-positive cells.

Figure 5:
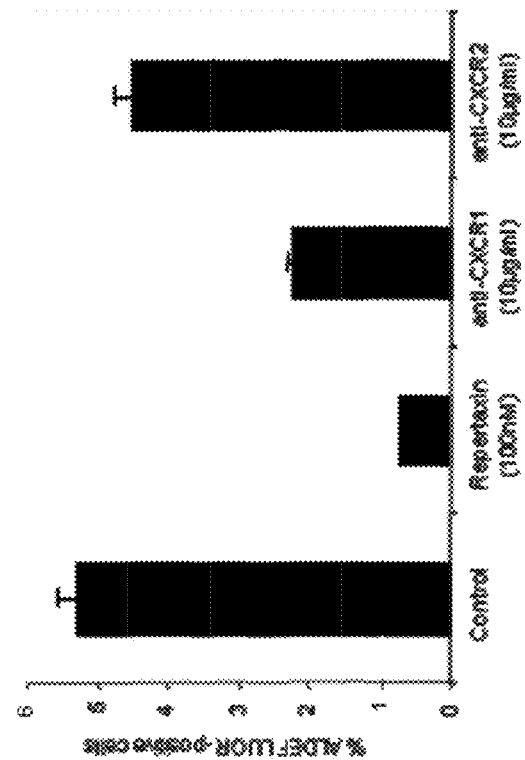
Figure 5:
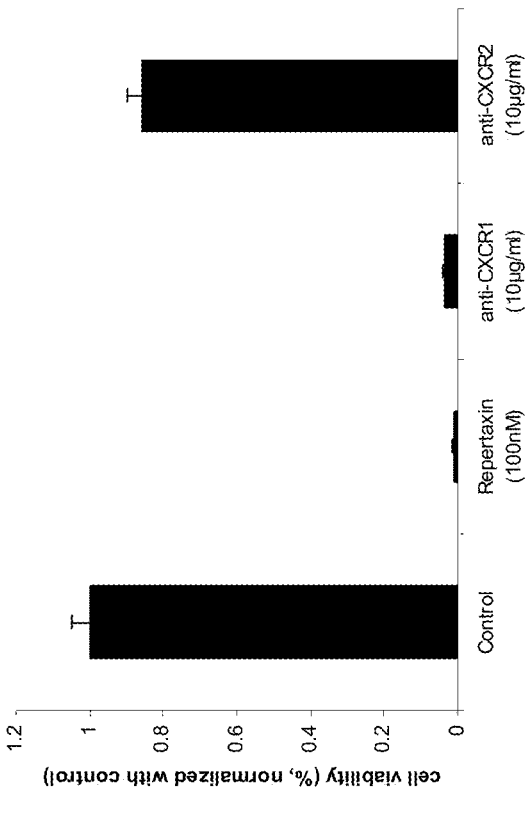

FIG. 5 shows the effect of CXCR1 inhibition on tumor cells viability (FIG. 5A) as well as on cancer stem cell viability (FIG. 5B).

Figure 6:
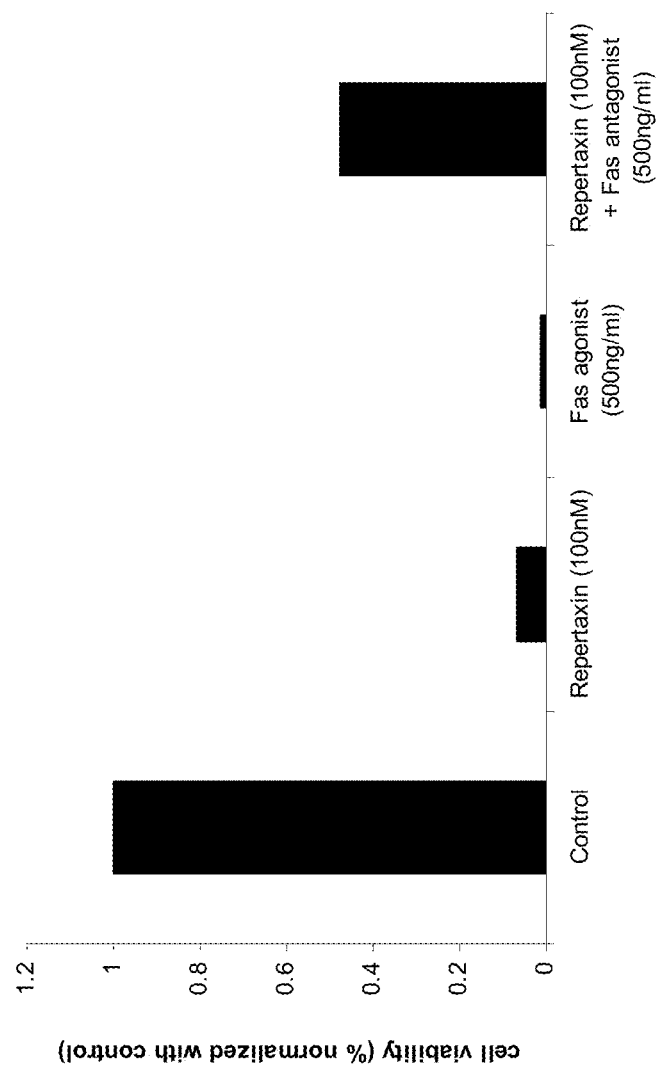

FIG. 6 shows that Repertaxin treatment induces a bystander effect mediated by the FAS/FAS ligand signaling, and specifically shows that the cell growth inhibition induced by the Repertaxin treatment was partially rescued by the addition of a FAS antagonist and that the cells treated with a FAS agonist displayed a similar cell growth inhibition than the cells treated with Repertaxin.

Figure 7:
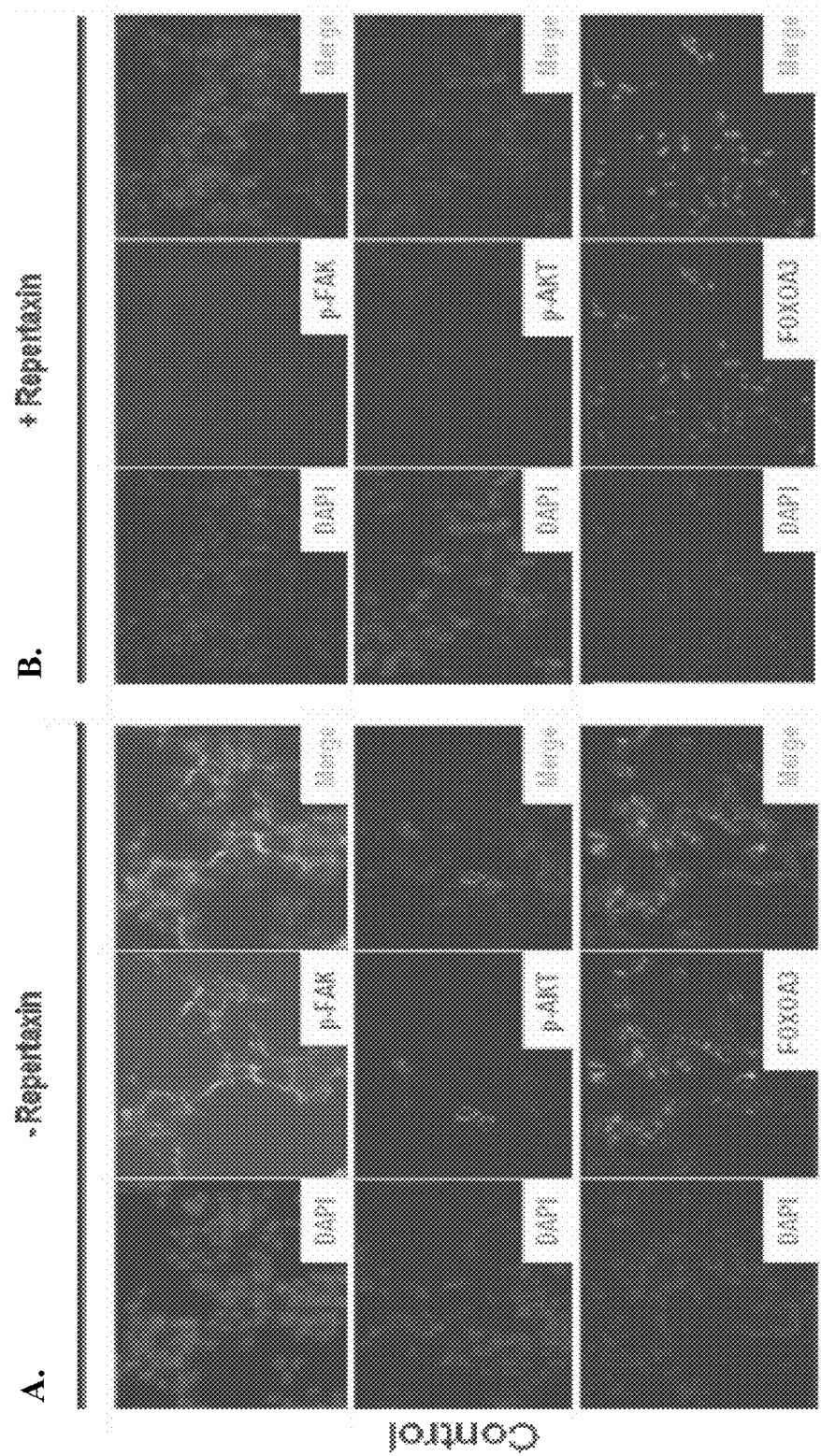

FIG. 7 shows the activation of FAK, AKT and FOXOA3 activation without Repertaxin treatment (7A) and in the presence of Repertaxin (7B).

Figure 8:
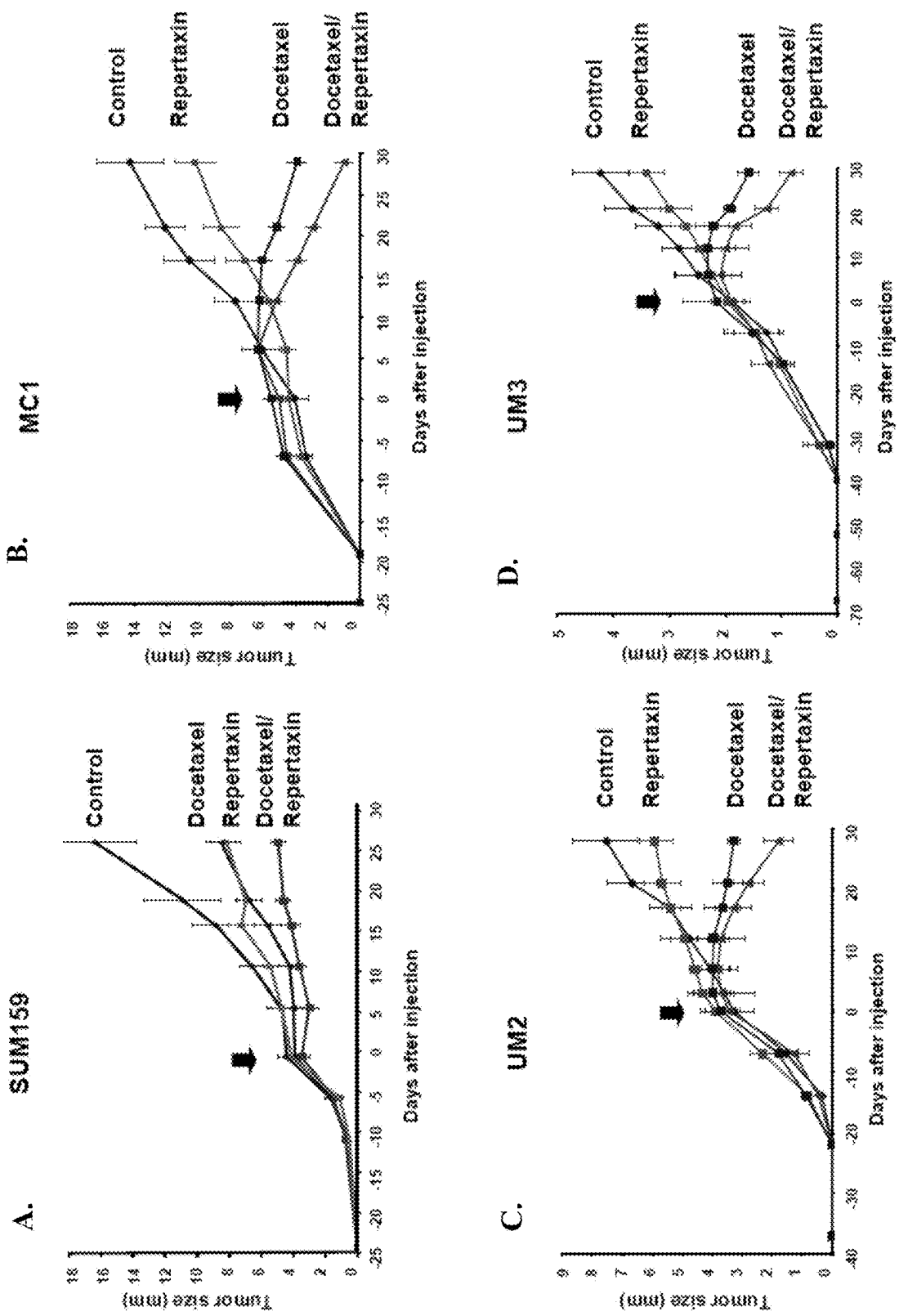

FIG. 8 shows the effect of Repertaxin, docetaxel, or the combination thereof on one breast cancer cell line (8A, SUM159) and three human breast cancer xenografts generated from different patients (8B, MC1; 8C, UM2; and 8D, UM3).

Figure 9:
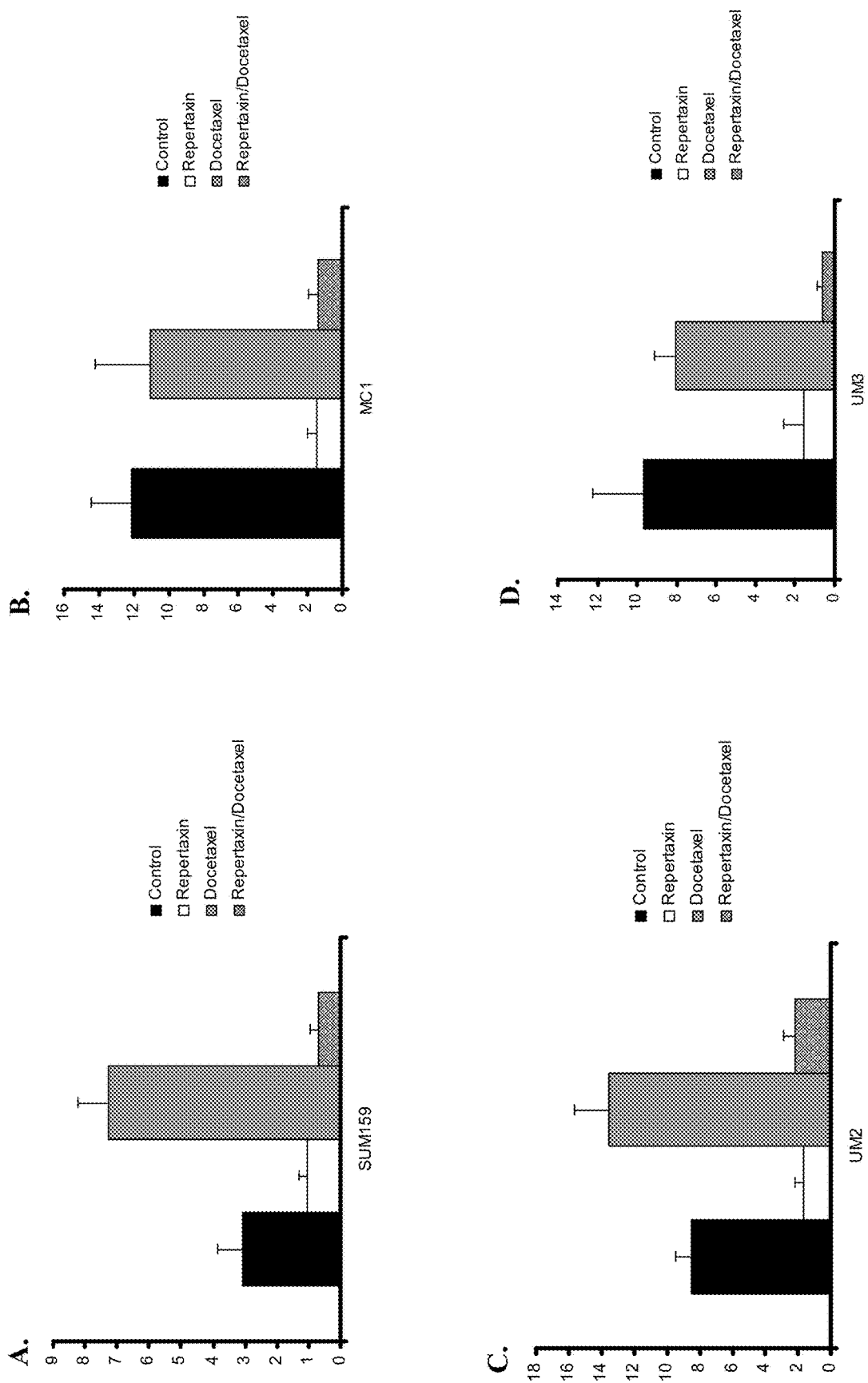

FIG. 9 shows the effect of Repertaxin, docetaxel, or the combination treatment on the cancer stem cell population as assessed by the ALDEFLUOR assay on various cells lines including SUM159 (9A), MC1 (9B), UM2 (9C), UM3 (9D).

Figure 10:
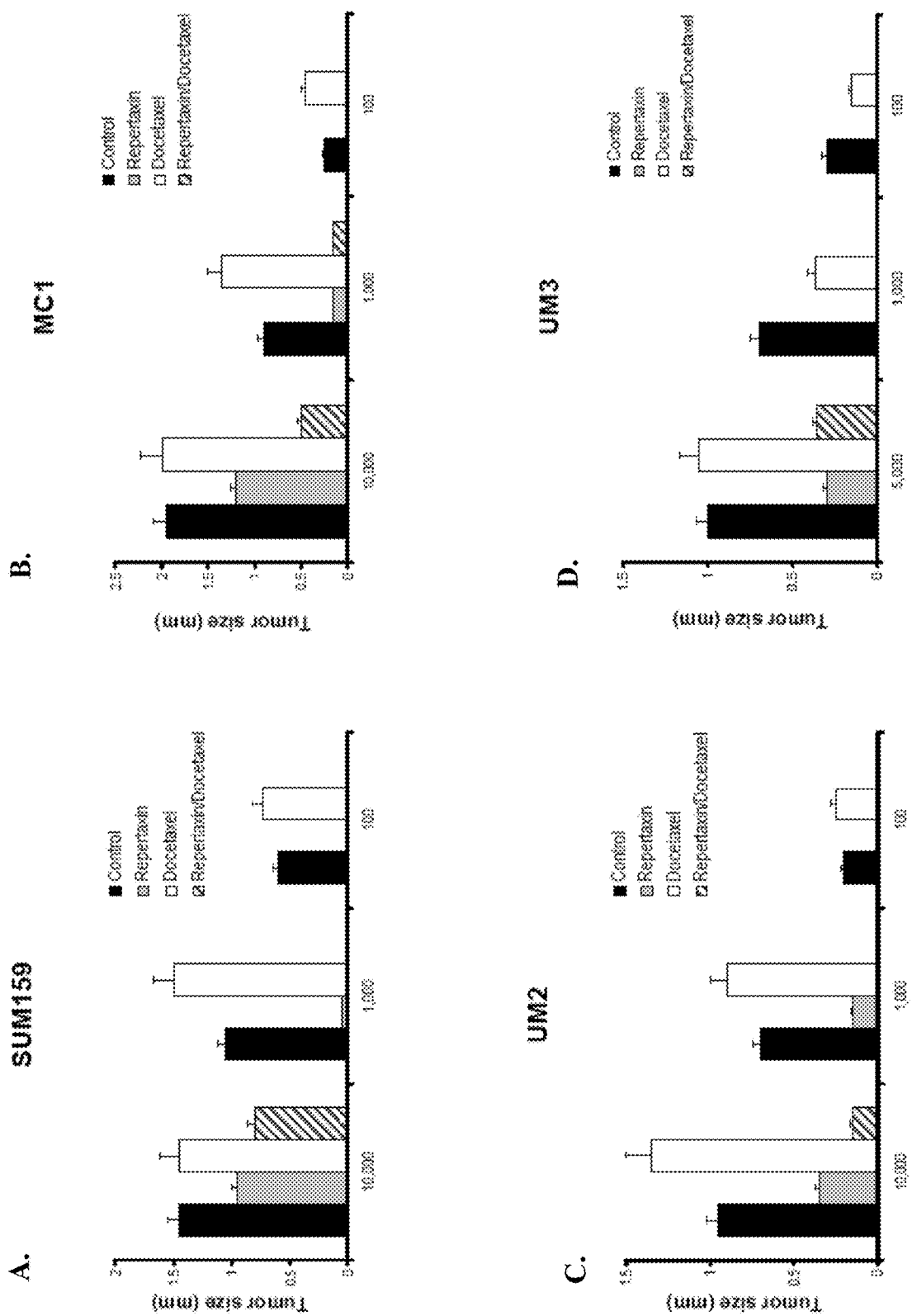

FIG. 10 shows the effect of Repertaxin, docetaxel or the combination on serial dilutions of primary tumors (10A. SUM159, 10B. MC1, 10C. UM2, 10D. UM3) that were implanted in the mammary fat pad of secondary NOD-SCID mice.

Figure 11:
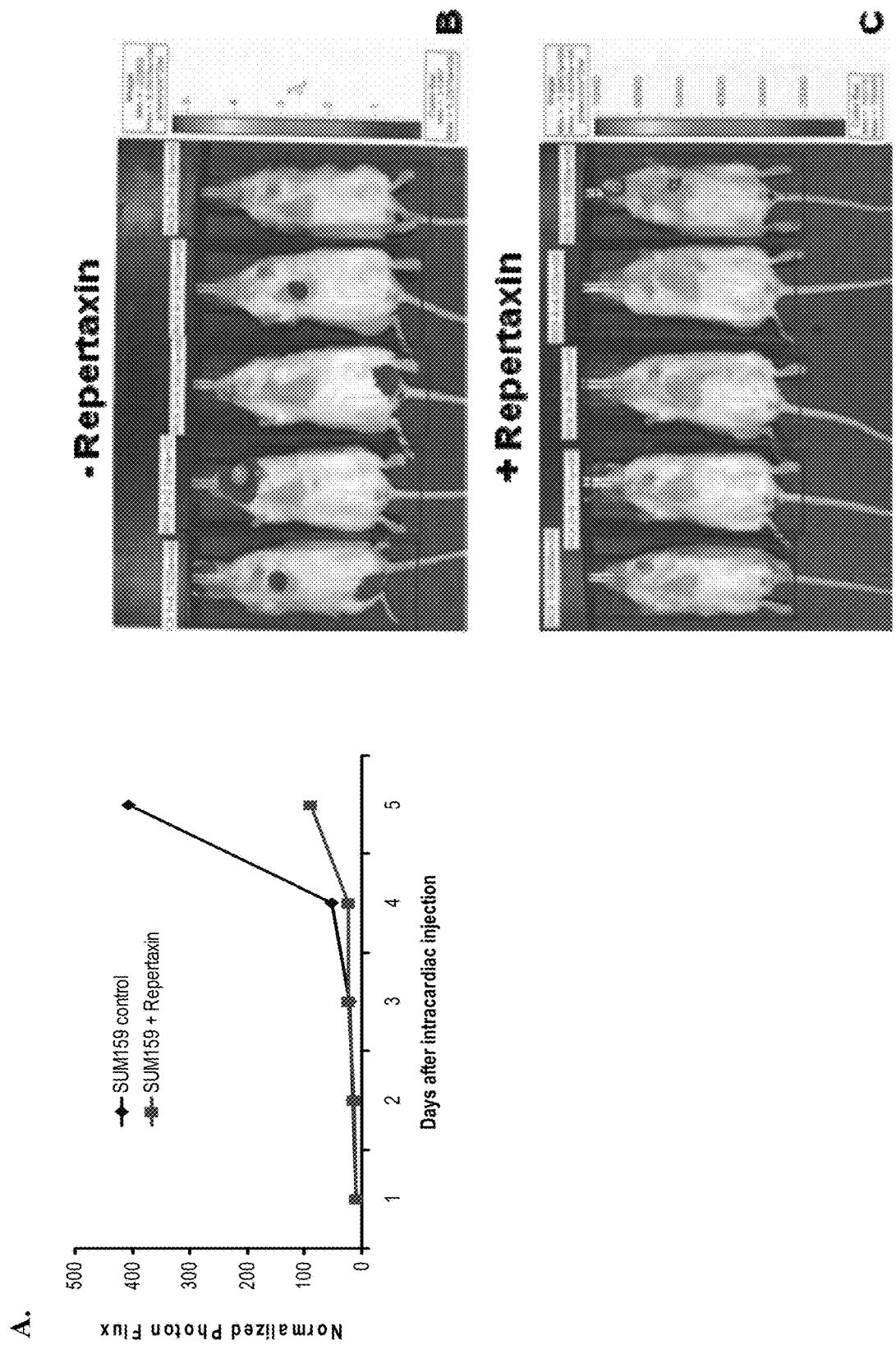

FIG. 11 shows that Repertaxin treatment reduces the metastatic potential of SUM159 cell line. FIG. 11A shows a quantification of the normalized photon flux measured at weekly intervals following inoculation with intracardiac administered SUM 159 cells. Metastasis formation was monitored using bioluminescence imaging (11B: Mice treated with saline solution; 11C: Mice treated with Repertaxin).

Figure 12:
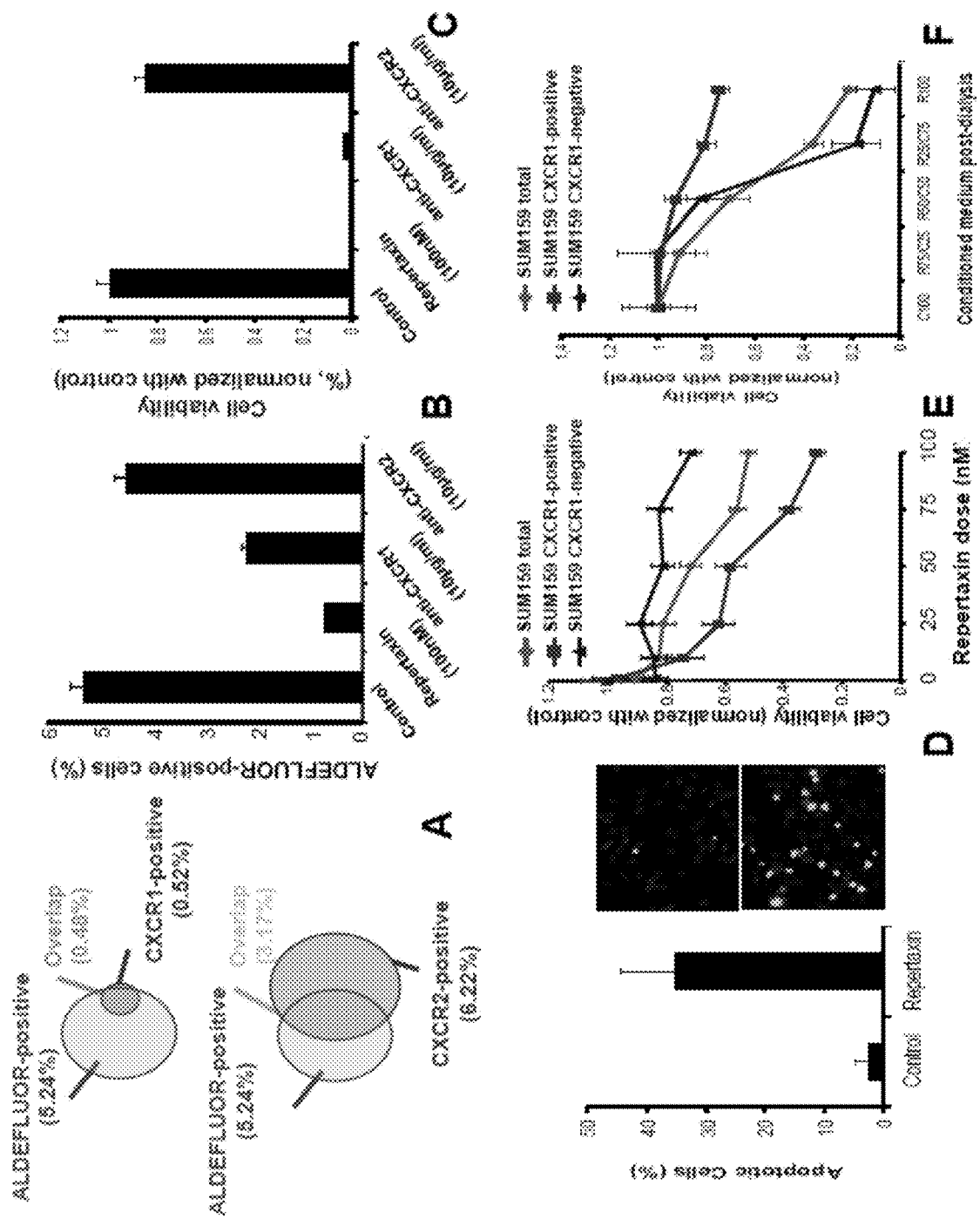

FIG. 12 shows representations of the overlap between the ALDEFLUOR-positive subpopulation and the CXCR1-positive subpopulation (top) or CXCR2-positive subpopulation (bottom) of SUM159 cells. B-C. SUM159 cells were cultured in adherent conditions and treated with repertaxin (100 nM) or two specific blocking antibodies for CXCR1 (10 µg/ml) or CXCR2 (10 µg/ml). After three days, the effect on the cancer stem cell population was analyzed using the ALDEFLUOR assay (B) cell viability was accessed after five days of treatment using the MTT assay (C). A significant reduction of the ALDEFLUOR-positive population and cell viability was observed following treatment with repertaxin or anti-CXCR1 antibody. In contrast no significant effect was observed with anti-CXCR2 antibody. D. After 4 days of treatment, the number of apoptotic cells was evaluated utilizing a TUNEL assay. 36% apoptotic cells (stained in green) were detected in repertaxin treated cells compared to the controls where mostly viable cells (stained in blue) were present. E-F. To determine whether cell death was mediated via a bystander effect. CXCR1-positive and CXCR1-negative populations were flow sorted and each population treated with various concentrations of repertaxin (D). A decrease in cell viability in CXCR1-positive and unsorted populations were detected whereas no effect was observed in the CXCR1-negative population (E). Dialyzed conditioned medium (dCM) from CXCR1-positive cells treated for three days with repertaxin was utilized to treat sorted CXCR1-positive, CXCR1-negative, or unsorted populations. Serial dilutions of dialyzed conditioned medium were utilized (Control, dCM ¼, dCM ½, dCM ¾, dCM). After two days of treatment, cell viability was evaluated utilizing the MTT assay. A massive decrease in cell viability was observed in both CXCR1-negative and unseparated populations whereas no effect was observed in the CXCR1-positive population (F).

Figure 13:
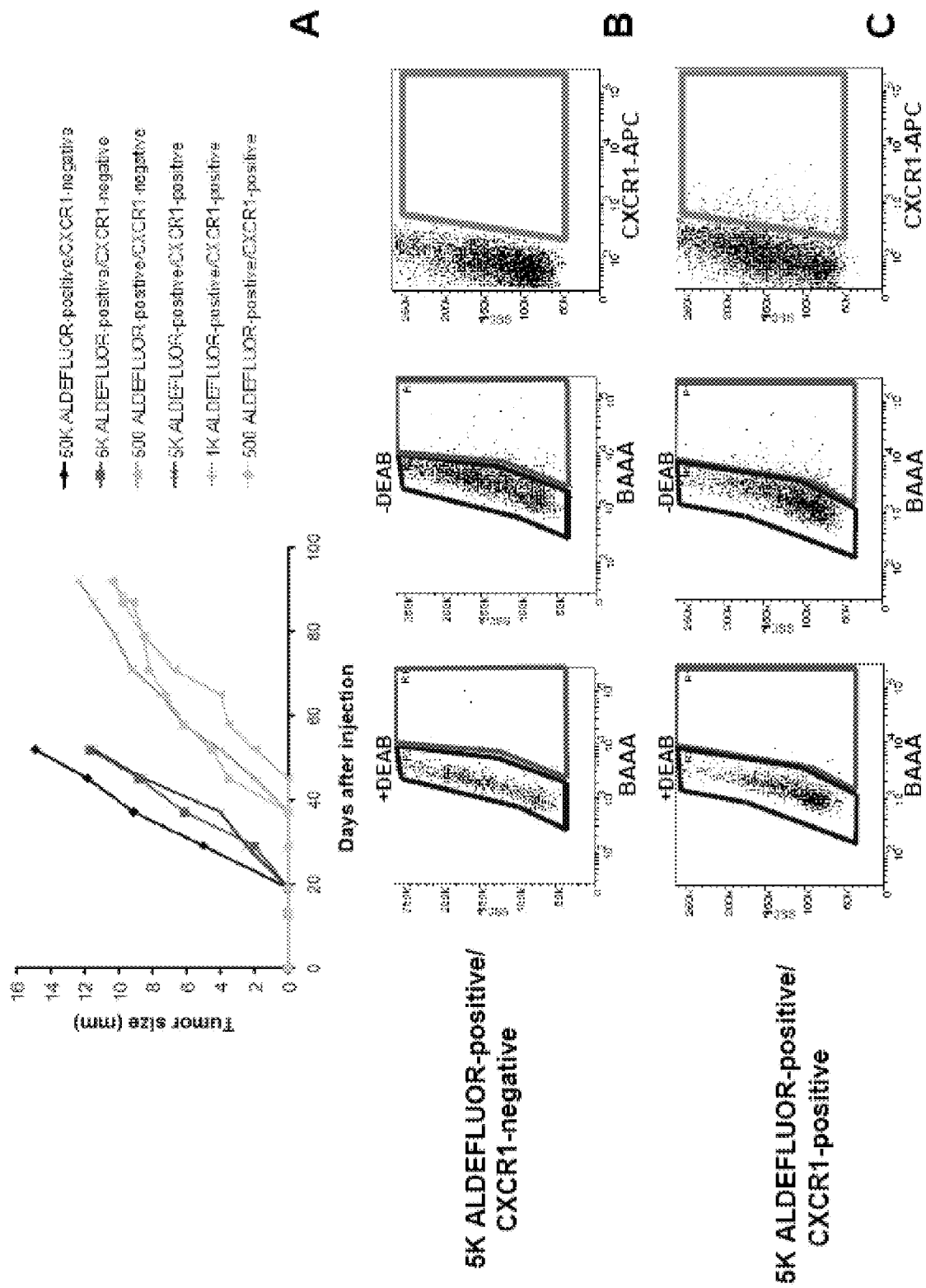

FIG. 13 shows tumorigenicity of the ALDEFLUOR-positive/CXCR1-positive and ALDEFLUOR-positive/CXCR1-negative cell populations from SUM159 cell line. A. Tumor growth curves were plotted for different numbers of cells injected (50,000 cells, 5,000 cells, 1,000 cells, and 500 cells) and for each population (ALDEFLUOR-positive/CXCR1-positive, ALDEFLUOR-positive/CXCR1-negative). Both cell populations generated tumors. Tumor growth kinetics correlated with the latency and size of tumor formation and the number of cells injected. B-C. Tumors generated by the ALDEFLUOR-positive/CXCR1-positive population reconstituted the phenotypic heterogeneity of the initial tumor upon serial passages whereas the ALDEFLUOR-positive/CXCR1-negative population gave rise to tumors containing only ALDEFLUOR-positive/CXCR1-negative cells. We transplanted both cell population for three passages.

Figure 14:
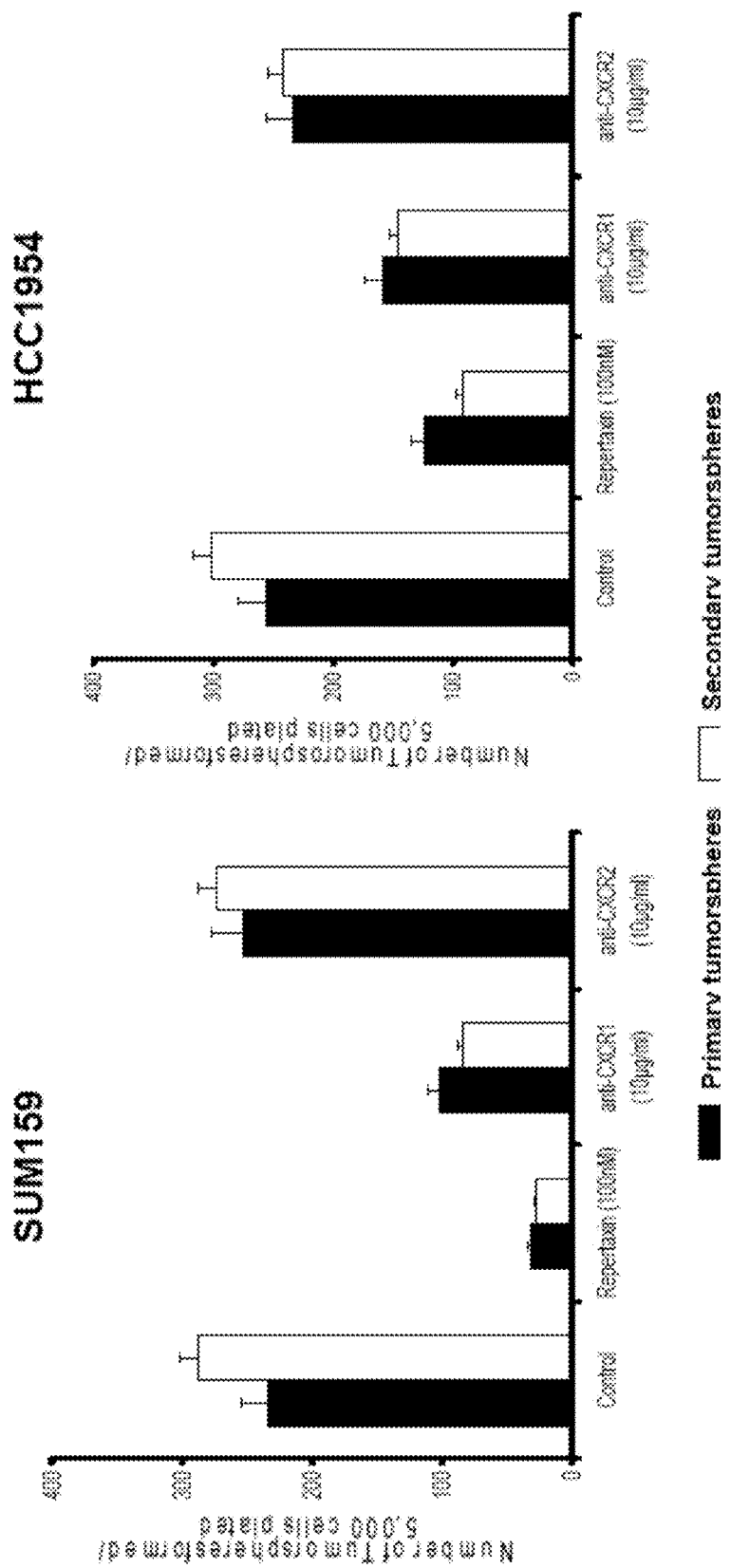

FIG. 14 shows the effect of CXCR1 blockade on tumorsphere formation. SUM159 and HCC1954 cells were cultured in adherent conditions and treated for three days with repertaxin (100 nM), an anti-CXCR1 blocking antibody (10 µg/ml), or an anti-CXCR2 blocking antibody (10 µg/ml). After three days of treatment, cells were detached and cultured in suspension. The number of tumorspheres formed after 5 days of culture were evaluated. Similar results were observed for the both cell lines with a significant decrease in primary and secondary tumorosphere formation in the repertaxin and anti CXCR1-treated conditions compared to controls. In contrast, anti-CXCR2 blocking antibody had no effect on tumorosphere formation.

Figure 15:
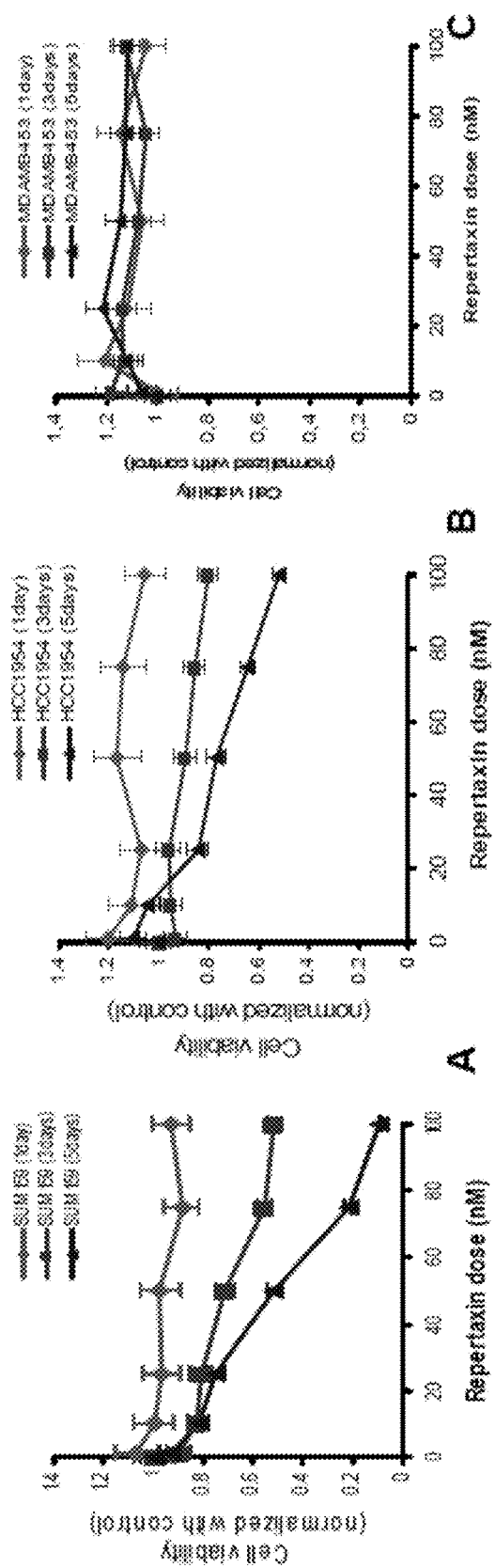

FIG. 15 shows the effect of repertaxin treatment on cell viability of SUM159, HCC1954, and MDA-MB-453 cell lines. Three different cell lines (SUM159, HCC1954, MDA-MB-453) were cultured in adherent conditions and treated with repertaxin (100 nM). Cell viability was evaluated after one, three, and five days of treatment using the MTT assay. A decrease in cell viability was observed after 3 days of treatment for SUM159 and HCC1954 cell line. However, repertaxin did not effect the viability of MDA-MB 453 cells.

Figure 16:
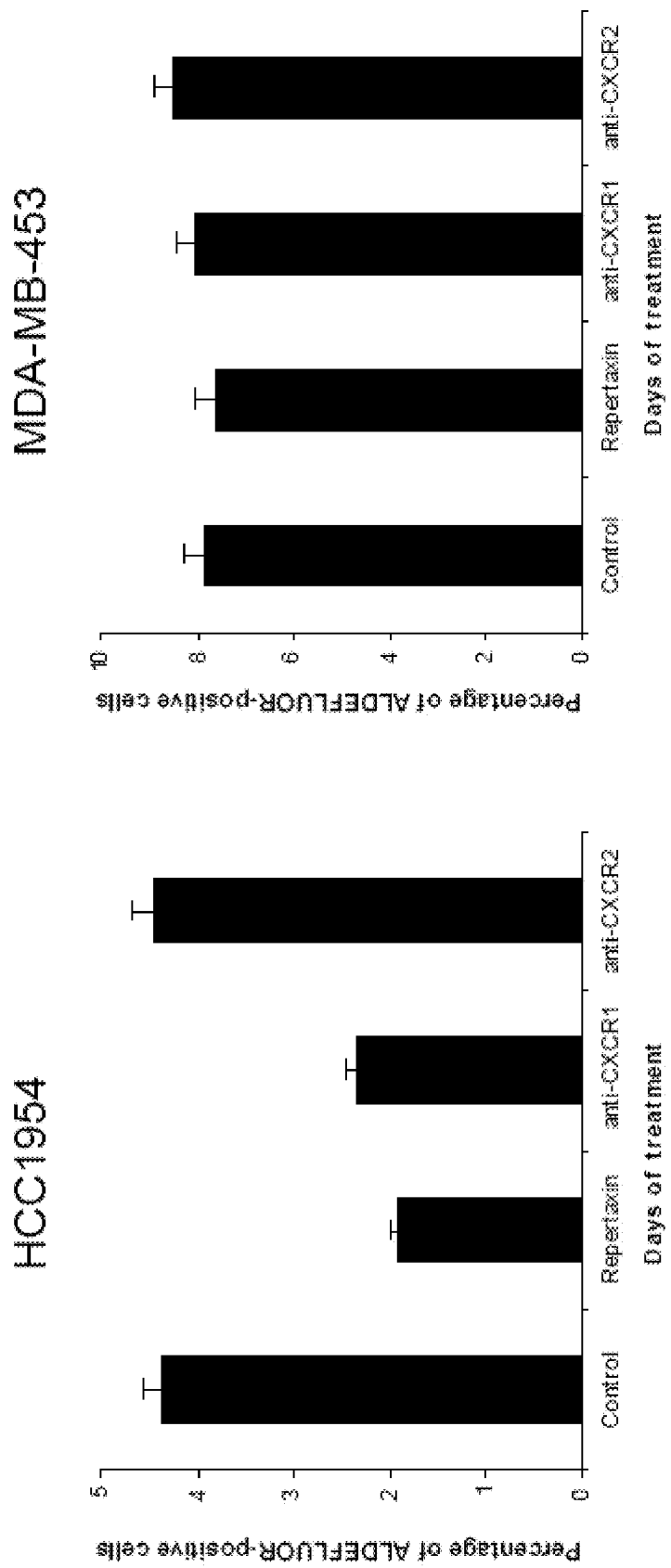

FIG. 16 shows the effect of CXCR1 blockade on the ALDEFLUOR-positive population in vitro. A-B. HCC1954 (A) and MDA-MB-453 (B) cells were cultured in adherent conditions and treated with repertaxin (100 nM) or two specific blocking antibodies for CXCR1 (10 µg/ml) or CXCR2 (10 µg/ml). After three days, the effect on the cancer stem cell population was analyzed using the ALDEFLUOR assay. For HCC1954, a significant reduction of the ALDEFLUOR-positive population and cell viability was observed following treatment with repertaxin or anti-CXCR1 antibody. In contrast no significant effect was observed with anti-CXCR2 antibody (A). For MDA-MB-453, np any effect on the ALDEFLUOR-positive population was observed (B).

Figure 17:
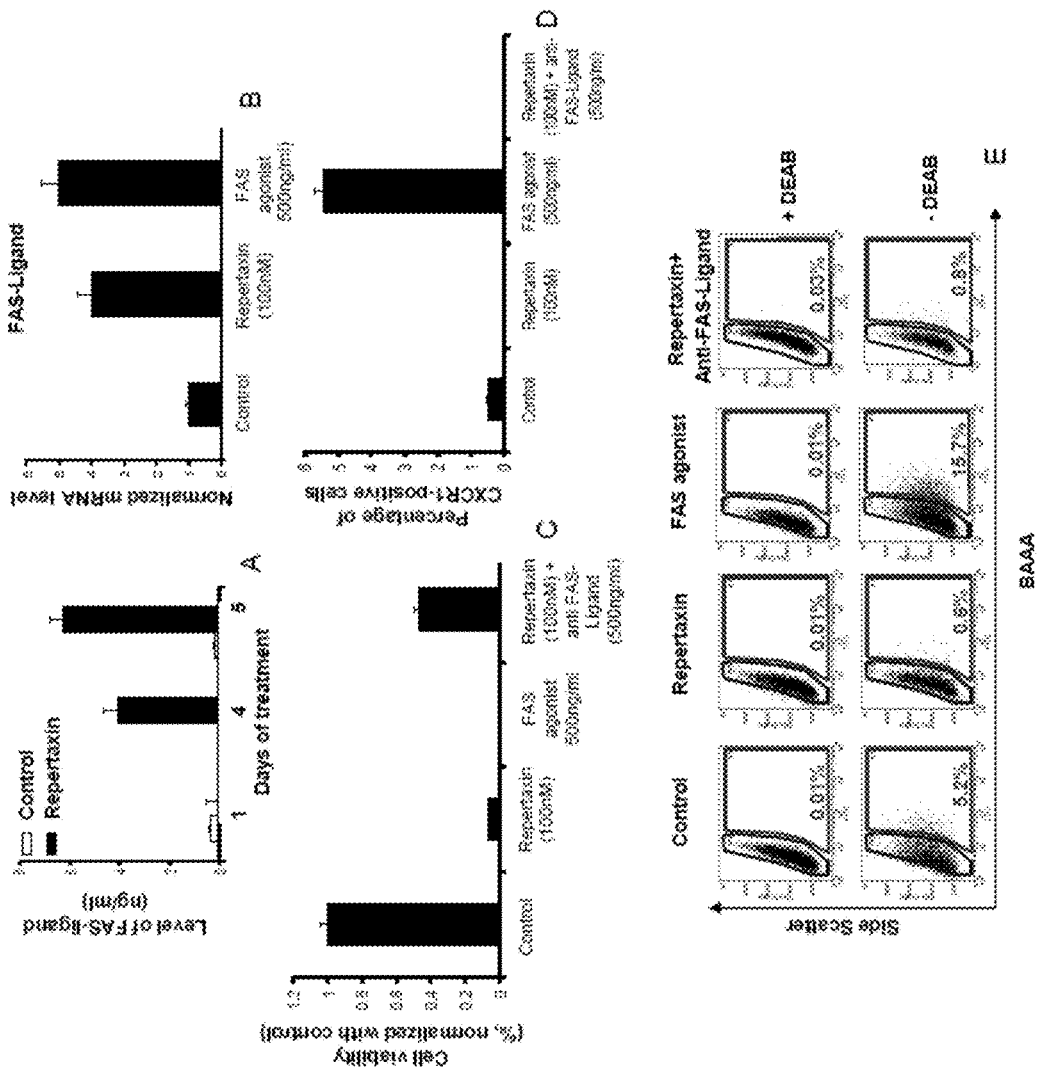

FIG. 17 shows repertaxin treatment induces a bystander effect mediated by FAS/FAS-ligand signaling. A. To determine whether the bystander killing effect induced by the repertaxin treatment was mediated by FAS-ligand, the level of soluble FAS-ligand in the medium was measured utilizing an ELISA assay. After 4 days of treatment, greater than a four-fold increase of soluble FAS-Ligand was detected in the medium of cells treated with repertaxin compared to non-treated controls. B. The level of FAS-ligand mRNA was measured by RT-PCR and confirmed the increase of FAS-ligand production after treatment with repertaxin. Similar results were observed after 4 days of treatment with a FAS agonist that activates FAS signaling, with a five-fold increase of the FAS-ligand mRNA compared to the control. C. SUM159 cells were cultured in adherent conditions and treated with repertaxin alone or in combination with an anti-FAS-ligand. Cell growth inhibition induced by the Repertaxin treatment was partially rescued by addition of anti-FAS-Ligand. Cells treated with a FAS agonist displayed similar cell growth inhibition to cells treated with repertaxin alone. D-E. The effect of repertaxin treatment alone or in combination with an anti-FAS-ligand and the treatment of a FAS-agonist on the CXCR1-positive and ALDEFLUOR-positive population was analyzed. The massive decrease in the CXCR1-positive and ALDEFLUOR-positive population induced by repertaxin treatment was not rescued by the anti-FAS-ligand and treatment with FAS-agonist produced a ten-fold and three-fold increase in the percent of the CXCR1-positive and ALDEFLUOR-positive population, respectively.

Figure 18:
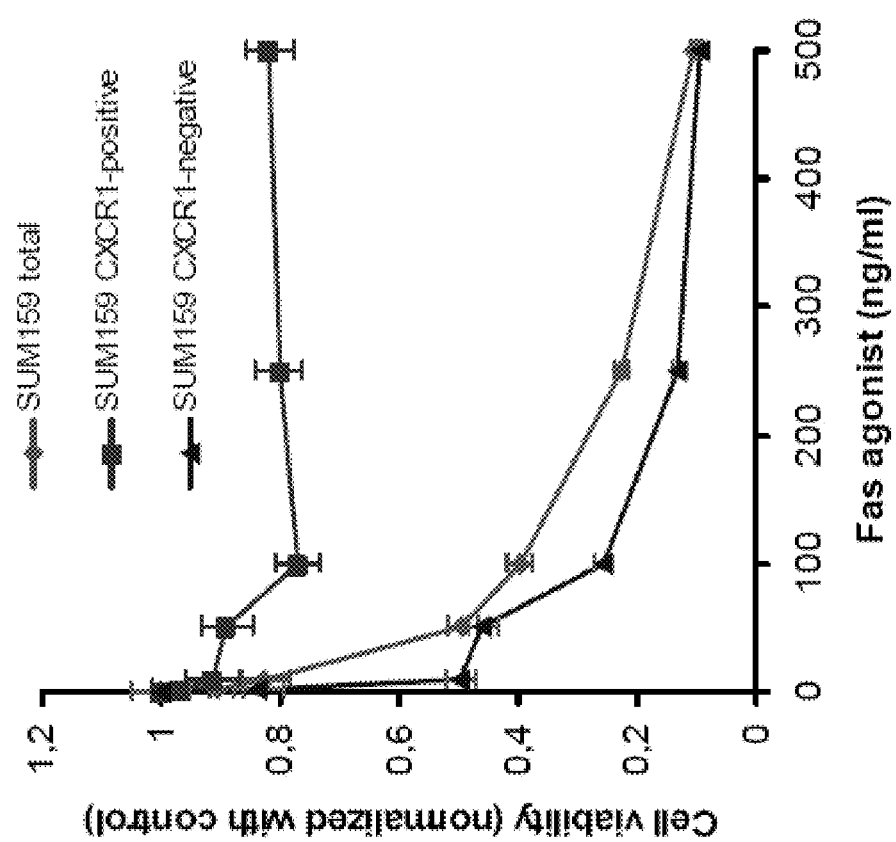

FIG. 18 shows the effect of FAS agonist on CXCR1-positive and CXCR1-negative cells. CXCR1-positive and CXCR1-negative populations were flow sorted and each population treated with various concentrations of FAS agonist. A decrease in cell viability in CXCR1-negative and unsorted populations were detected whereas no effect was observed in the CXCR1-positive population.

Figure 19:
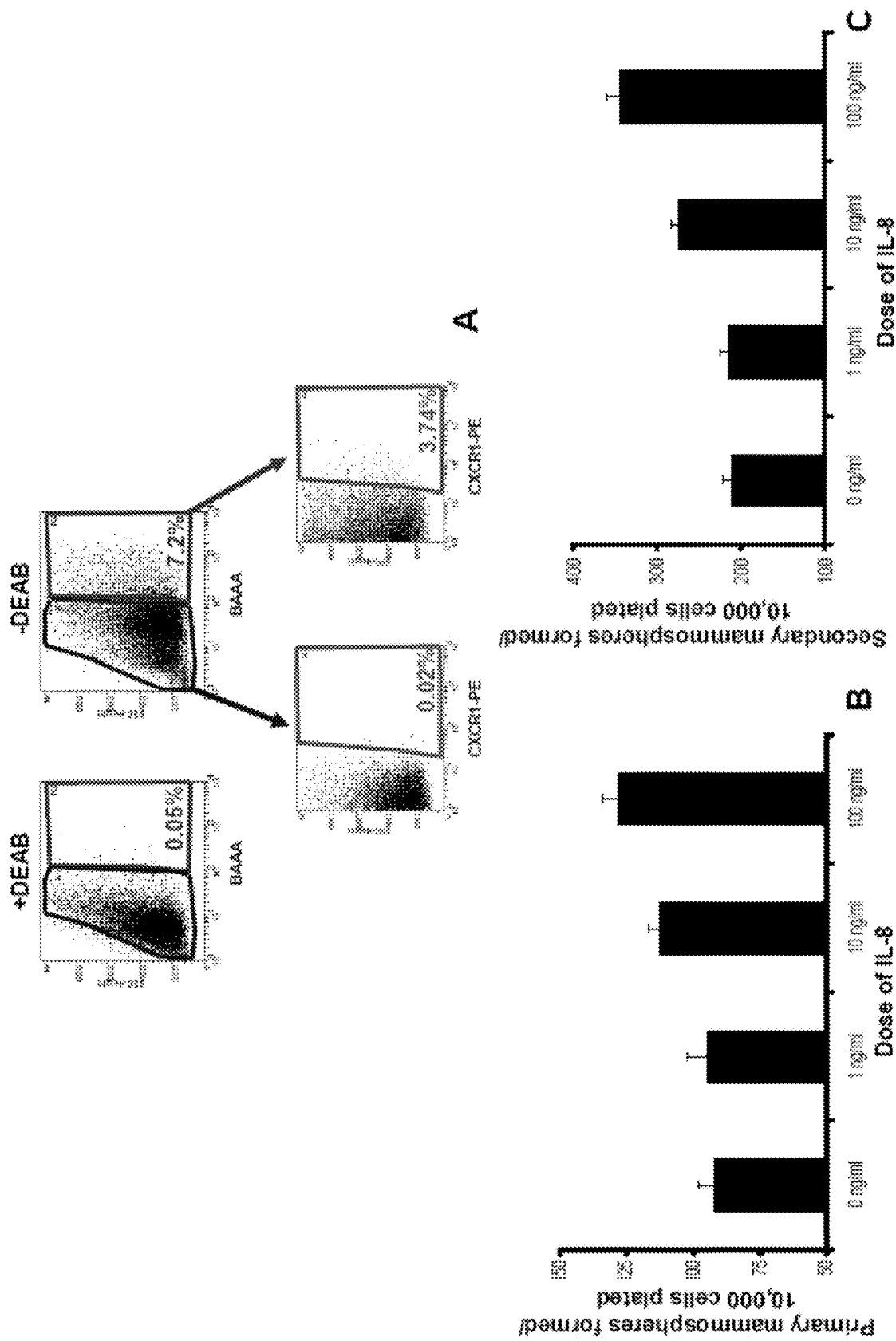

FIG. 19 shows analysis of CXCR1 protein expression in the normal breast stem/progenitor population and effect of IL-8 treatment on mammosphere formation. A. The ALDEFLUOR-positive and -negative population from normal breast epithelial cells isolated form reduction mammoplasties was isolated by FACS, fixed, and analyzed for the expression of CXCR1 protein by immunostaining and FACS analysis. ALDEFLUOR-positive cells were highly enriched in CXCR1-positive cells compared to the ALDEFLUOR-negative population. B-C. Effect of IL8 treatment on mammosphere formation. IL8 treatment increased the formation of primary (B) and secondary mammospheres (C) in a dose-dependent manner.

Figure 20:
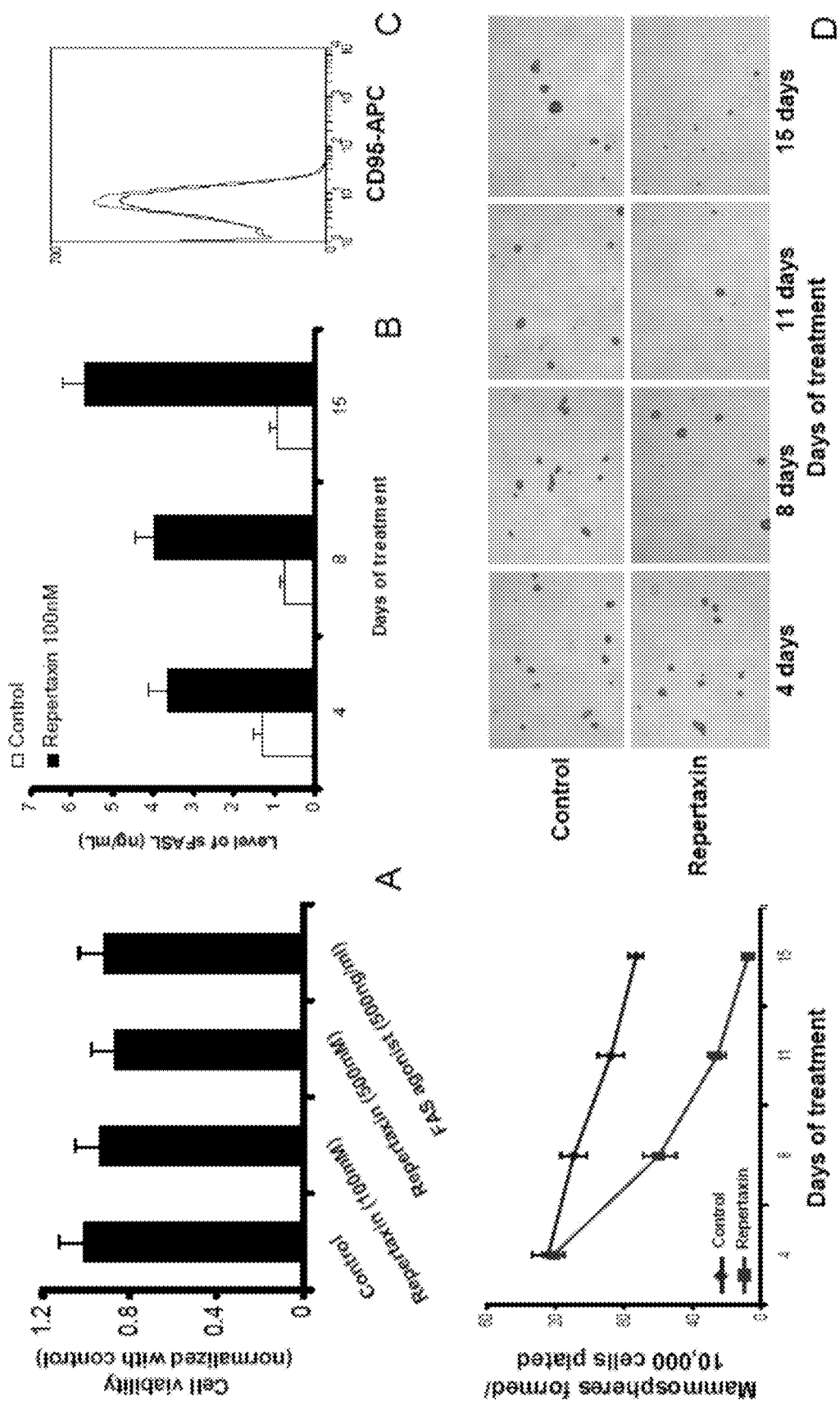

FIG. 20 shows the effect of repertaxin treatment on the normal mammary epithelial cells. A. Normal mammary epithelial cells isolated from reduction mammoplasties were cultured in adherent condition and treated with repertaxin (100 nM or 500 nM) or FAS agonist (500 ng/ml). After five days of treatment cell viability was evaluated using MTT assay. Repertaxin treatment or the FAS agonist had no effect on the viability of normal mammary epithelial cells cultured in adherent conditions, even when high concentrations of repertaxin (500 nM) were utilized. B. The level of soluble FAS-ligand was evaluated by Elisa assay in the medium of normal mammary epithelial cells treated with repertaxin. After 4 days of treatment an increase of soluble FAS-ligand was detected in the medium from treated cells. C. Analysis of FAS/CD95 expression in the normal mammary epithelial cells by FACS analysis. No FAS/CD95 expression was detected in the normal mammary epithelial cells cultured in adherent condition. D. Effect of repertaxin treatment on mammosphere formation. Normal mammary epithelial cells were cultured in adherent condition and treated during four, eight, eleven and fifteen days with repertaxin (100 nM). After repertaxin treatment cells were detached and cultured in suspension. A significant decrease of mammosphere-initiating cells was observed in the repertaxin-treated condition.

Figure 21:
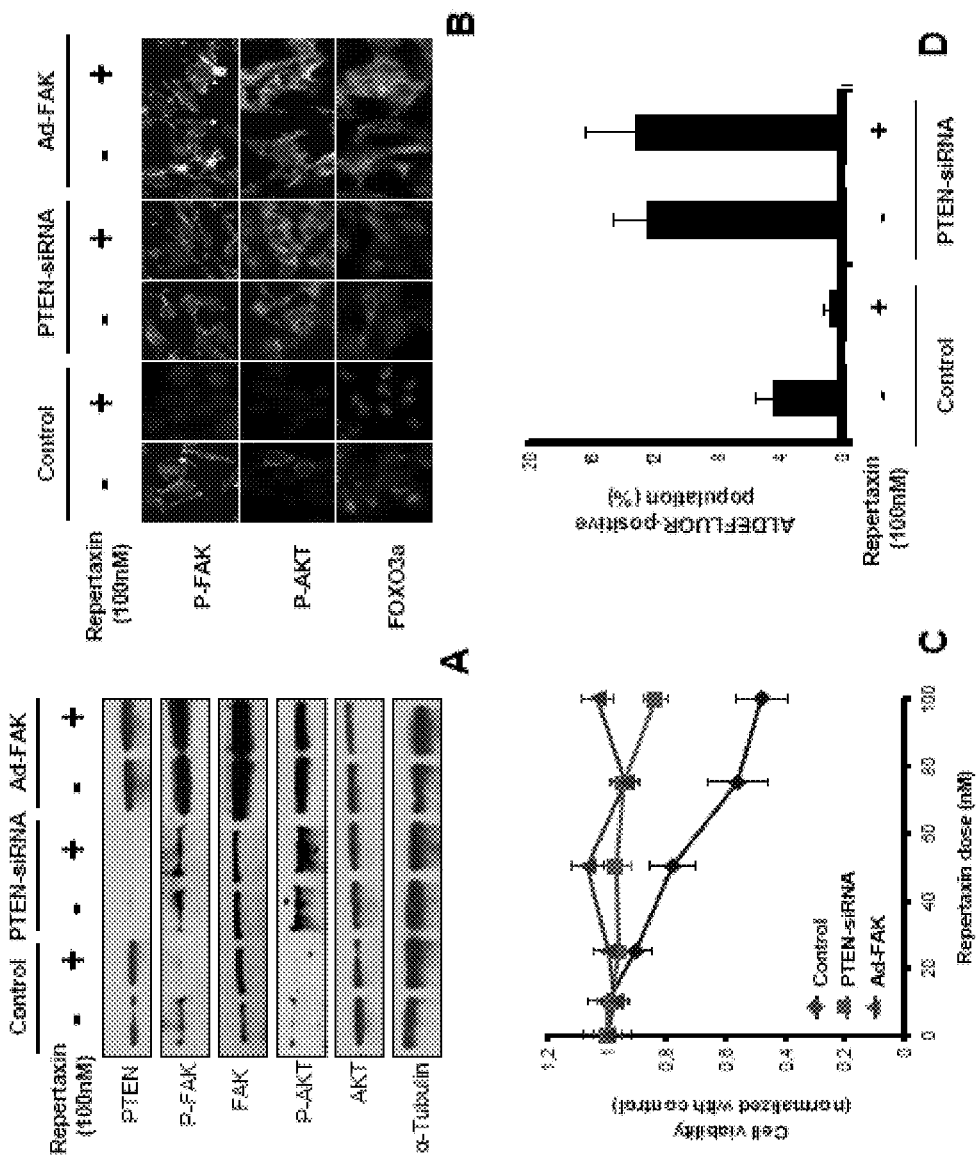

FIG. 21 shows the effect of repertaxin treatment on FAK, AKT and FOXO3a activation. To evaluate the effect of repertaxin treatment on CXCR1 downstream signaling, two different viral constructs were utilized, one knocking down PTEN expression via a PTEN-siRNA and the other leading to FAK overexpression (Ad-FAK). A. SUM159 control, SUM159 PTEN-siRNA, and SUM159 Ad-FAK cells were cultured in adherent conditions for two days in the absence or presence of 100 nM repertaxin and the activation of the FAK/AKT pathway was accessed by western blotting. Repertaxin treatment led to a decrease in FAK Tyr397 and AKT Ser473 phosphorylation whereas PTEN deletion and FAK overexpression blocked the effect of repertaxin treatment on FAK and AKT activity. B. Utilizing immunofluorescence staining on CXCR1-positive cells, we confirmed that Repertaxin treatment results in a disappearance of phospho-FAK (membranous staining in red) and phospho-AKT expression (cytoplasmic staining in red). Immunofluorescence staining with an anti-FOXO3A revealed a cytoplasmic location of FOXO3a (in red) in the untreated cells whereas repertaxin treatment induced a re-localization of FOXO3A to the nucleus. In contrast, cells with PTEN deletion or FAK overexpression display a high level of phospho-FAK, phospho-AKT and cytoplasmic FOXO3A expression in both the repertaxin treated and untreated cells. In all samples, nuclei were counterstained with DAPI (in blue). C-D. The effect of Repertaxin on the SUM159 PTEN-siRNA and SUM159 Ad-FAK cell viability and on the cancer stem cell population was assessed utilizing the MTT and ALDEFLUOR assays, respectively. After 3 days of treatment, cells with PTEN deletion or FAK overexpression developed resistance to repertaxin (C). Repertaxin treatment did not alter the proportion of ALDEFLUOR-positive SUM159 PTEN knockdown cells. (D).

Figure 22:
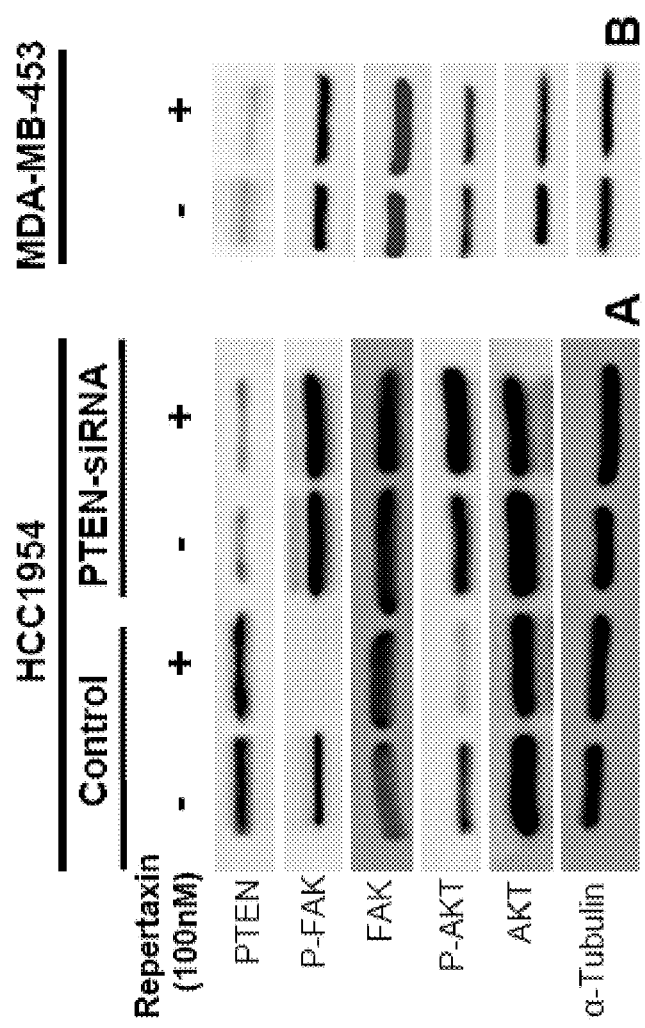

FIG. 22 shows the effect of repertaxin treatment on FAK/AKT activation in HCC1954 and MDA-MB-453 cell lines. To evaluate the effect of repertaxin treatment on CXCR1 downstream signaling we utilized a lentiviral construct knocking down PTEN expression via a PTEN-siRNA A. HCC1954 control and HCC1954 PTEN-siRNA cells were cultured in adherent conditions for two days in the absence or presence of 100 nM repertaxin and the activation of the FAK/AKT pathway was accessed by western blotting. Repertaxin treatment led to a decrease in FAK Tyr397 and AKT Ser473 phosphorylation whereas PTEN deletion blocked the effect of repertaxin treatment on FAK and AKT activity. B. Repertaxin treatment did not have any effect on cell viability of MDA-MB-453 cell line which harbor PTEN mutation. Utilizing western blot analysis we confirmed that FAK/AKT pathway was not perturbated by repertaxin treatment.

Figure 23:
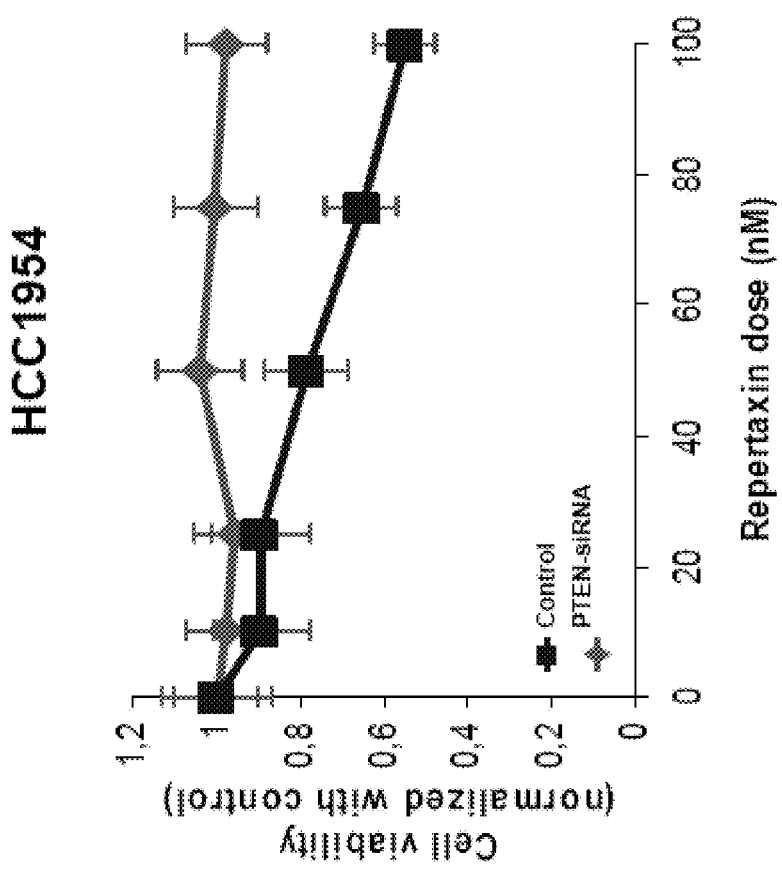

FIG. 23 shows the effect of repertaxin on the HCC1954 PTEN-siRNA cell viability, assessed utilizing the MTT assay. After 3 days of treatment, cells with PTEN deletion developed resistance to repertaxin.

Figure 24:
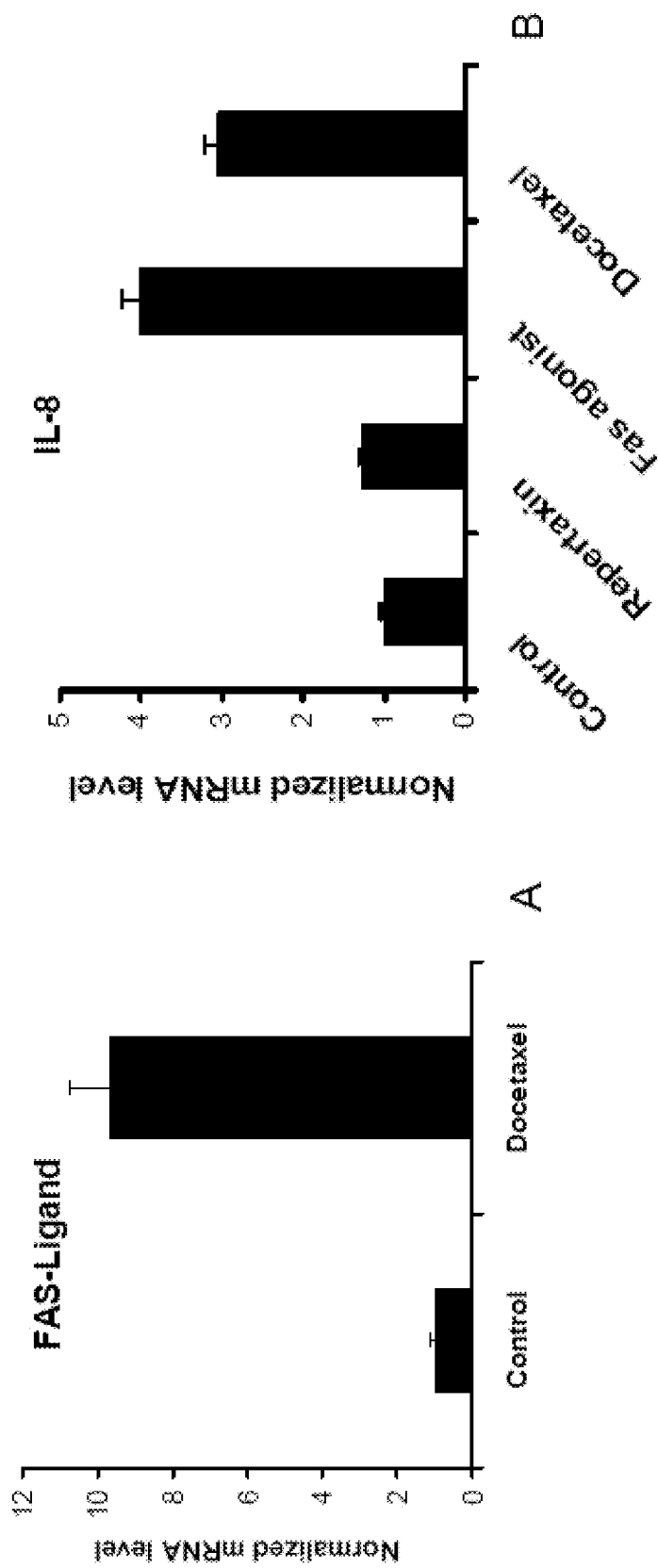

FIG. 24 shows expression of FAS-ligand and IL-8 mRNA after docetaxel or repertaxin treatment measured by quantitative RT-PCR. A-B. SUM159 cells cultured in adherent condition were treated with repertaxin (100 nM), FAS agonist (500 ng/ml) or docetaxel (10 nM). After three days of treatment cells were collected and RNA extracted. Docetaxel, induced both FAS-ligand (A) and IL-8 (B) mRNA in SUM159 cells. A 4-fold increase of IL-8 mRNA level was detected after FAS agonist or docetaxel treatment (B).

Figure 25:
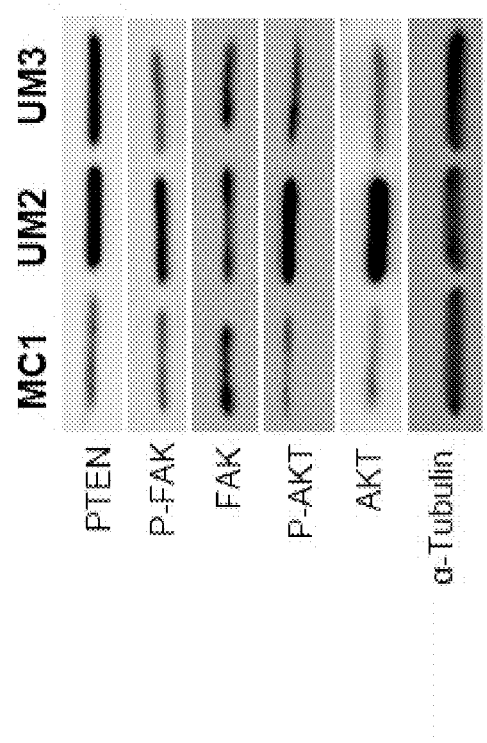

FIG. 25 shows evaluation of PTEN/FAK/AKT activation in the three different breast cancer xenografts. Western blot analysis revealed that both xenografts presented an expression of PTEN and an activation of FAK/AKT pathway as shown by FAK Tyr397 and AKT Ser473 phosphorylation.

Figure 26:
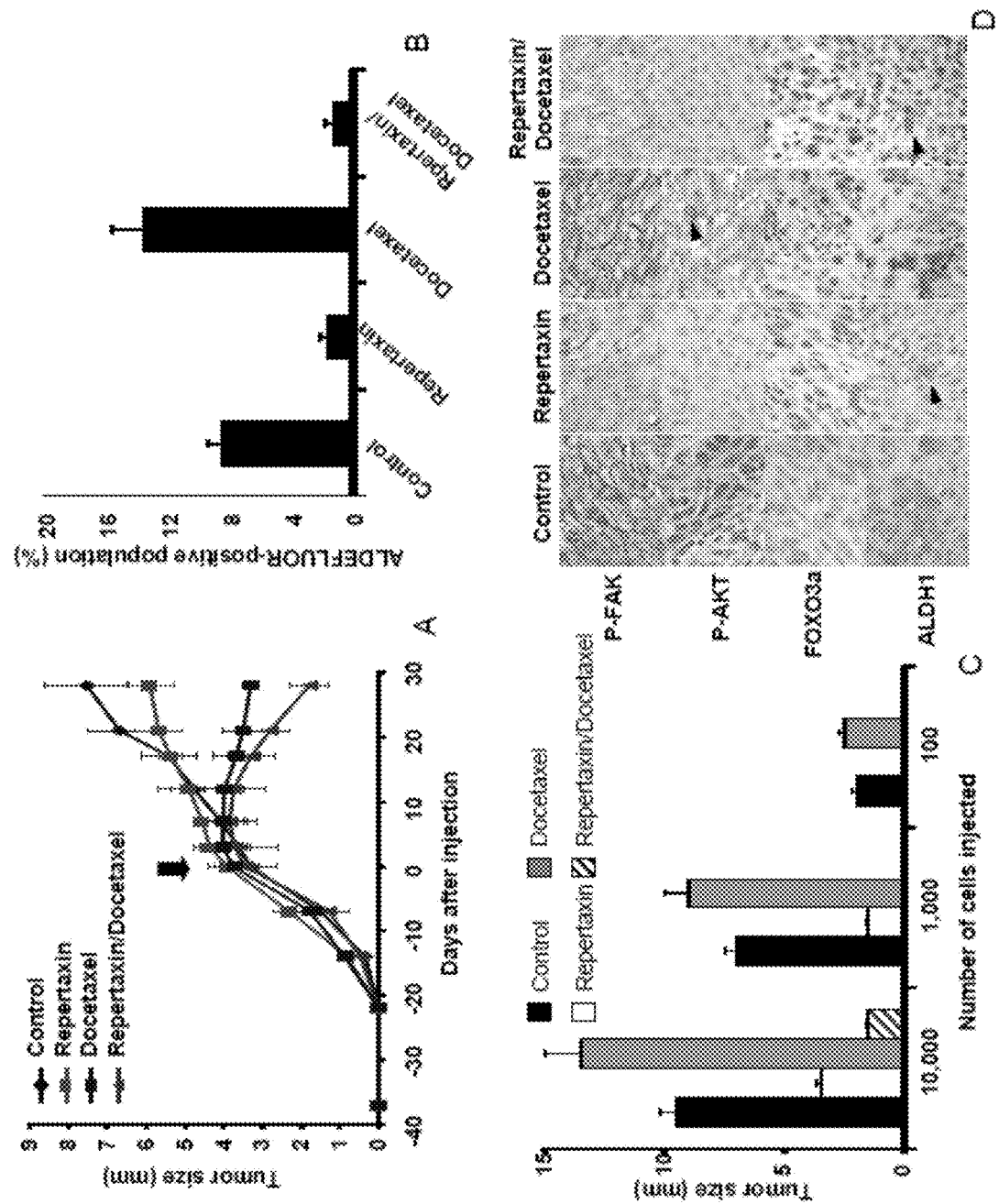

FIG. 26 shows Effect of Repertaxin treatment on the breast cancer stem cell population in vivo. A-C. To evaluate the effect of repertaxin treatment on tumor growth and the cancer stem cell population in vivo a breast cancer cell line (SUM159) and three human breast cancer xenografts generated from different patients (MC1, UM2, UM3) were utilized. A. For each sample, 50,000 cells were injected into the humanized mammary fat pad of NOD/SCID mice and monitored tumor size. When the tumors were about 4 mm, s.c. injection of repertaxin (15 mg/Kg) twice/day for 28 days or once/week I.P. injection of docetaxel (10 mg/Kg) or the combination (repertaxin/docetaxel) was initiated. The graph shows the tumor size before and during the course of each indicated treatment (arrow, beginning of the treatment). Similar results were observed for each sample with a statistically significant reduction of the tumor size in docetaxel alone or the combination repertaxin/docetaxel treated groups compared to the control, whereas no difference was observed between the growth of the control tumors and the tumors treated with repertaxin alone. B-C. Evaluation of repertaxin, docetaxel, or the combined treatment on the cancer stem cell population as assessed by the ALDEFLUOR assay (B) and by reimplantation into secondary mice (C). Docetaxel-treated tumor xenografts showed similar or increase percentage of ALDEFLUOR-positive cells compared to the control, whereas repertaxin treatment alone or in combination with docetaxel produced a statistically significant decrease in ALDEFLUOR-positive cells with a 65% to 85% decrease in cancer stem cells compared to the control (p<0.01) (B). Serial dilutions of cells obtained from primary tumors, non treated (control), and treated mice were implanted in the mammary fat pad of secondary NOD/SCID mice which received no further treatment. Control and docetaxel treated primary tumors formed secondary tumors at all dilutions whereas, only higher numbers of cells obtained from primary tumors treated with repertaxin or in combination with docetaxel were able to form tumors. Furthermore, tumor growth was significantly delayed and resulting tumors were significantly smaller in size than the control or docetaxel treated tumors (C). D. Xenotransplants from each group were collected and immunohistochemistry staining was done to detect the expression of phospho-FAK, phospho-AKT, FOXO3A, and ALDH1. Membranous phospho-FAK expression and cytoplasmic phospho-AKT expression (arrow) was detected in the control and docetaxel-treated tumors whereas no expression was detected in the tumors treated with repertaxin alone or in combination with docetaxel. Nuclear FOXO3A expression (in brown) was detected in the cells treated with docetaxel or repertaxin alone or in combination. A decrease of ALDH1 expression (arrow) was detected in tumors treated with repertaxin alone or in combination compared to control and the docetaxel-treated tumors.

Figure 27:
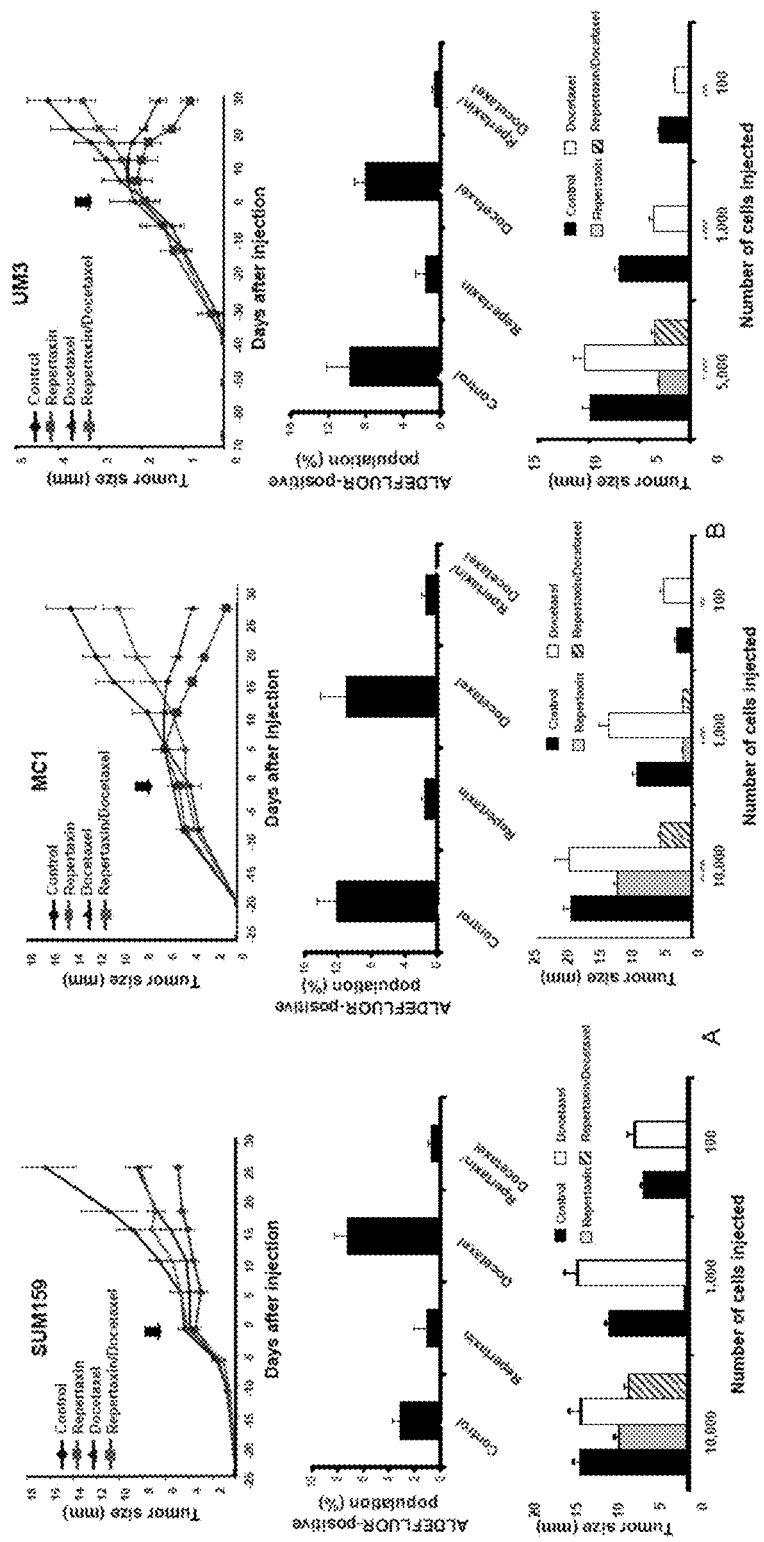

FIG. 27 shows the effect of Repertaxin treatment on the breast cancer stem cell population in vivo. A-C. To evaluate the effect of repertaxin treatment on tumor growth and the cancer stem cell population in vivo, a breast cancer cell line (SUM159, A) and three human breast cancer xenografts generated from different patients. For each sample, 50,000 cells were injected into the humanized mammary fat pad of NOD/SCID mice and monitored tumor size. When the tumors were about 4 mm, s.c. injection of repertaxin (15 mg/Kg) twice/day for 28 days or once/week I.P. injection of docetaxel (10 mg/Kg) or the combination (repertaxin/docetaxel) was initiated. The graph shows the tumor size before and during the course of each indicated treatment (arrow, beginning of the treatment). Similar results were observed for each sample with a statistically significant reduction of the tumor size in docetaxel alone or the combination repertaxin/docetaxel treated groups compared to the control whereas no difference was observed between the growth of the control tumors and the tumors treated with repertaxin alone. Evaluation of repertaxin, docetaxel, or the combined treatment on the cancer stem cell population was assessed by the ALDEFLUOR assay and by reimplantation into secondary mice. Docetaxel-treated tumor xenografts showed similar or increased percentage of ALDEFLUOR-positive cells compared to the control, whereas repertaxin treatment alone or in combination with docetaxel produced a statistically significant decrease in ALDEFLUOR-positive cells with a 65% to 85% decrease in cancer stem cells compared to the control (p<0.01). Serial dilutions of cells obtained from primary tumors, non-treated (control), and treated mice were implanted in the mammary fat pad of secondary NOD/SCID mice which received no further treatment. Control and docetaxel treated primary tumors formed secondary tumors at all dilutions whereas, only higher numbers of cells obtained from primary tumors treated with repertaxin or in combination with docetaxel were able to form tumors. Tumor growth was significantly delayed and resulting tumors were significantly smaller in size than the control or docetaxel treated tumors.

Figure 28:
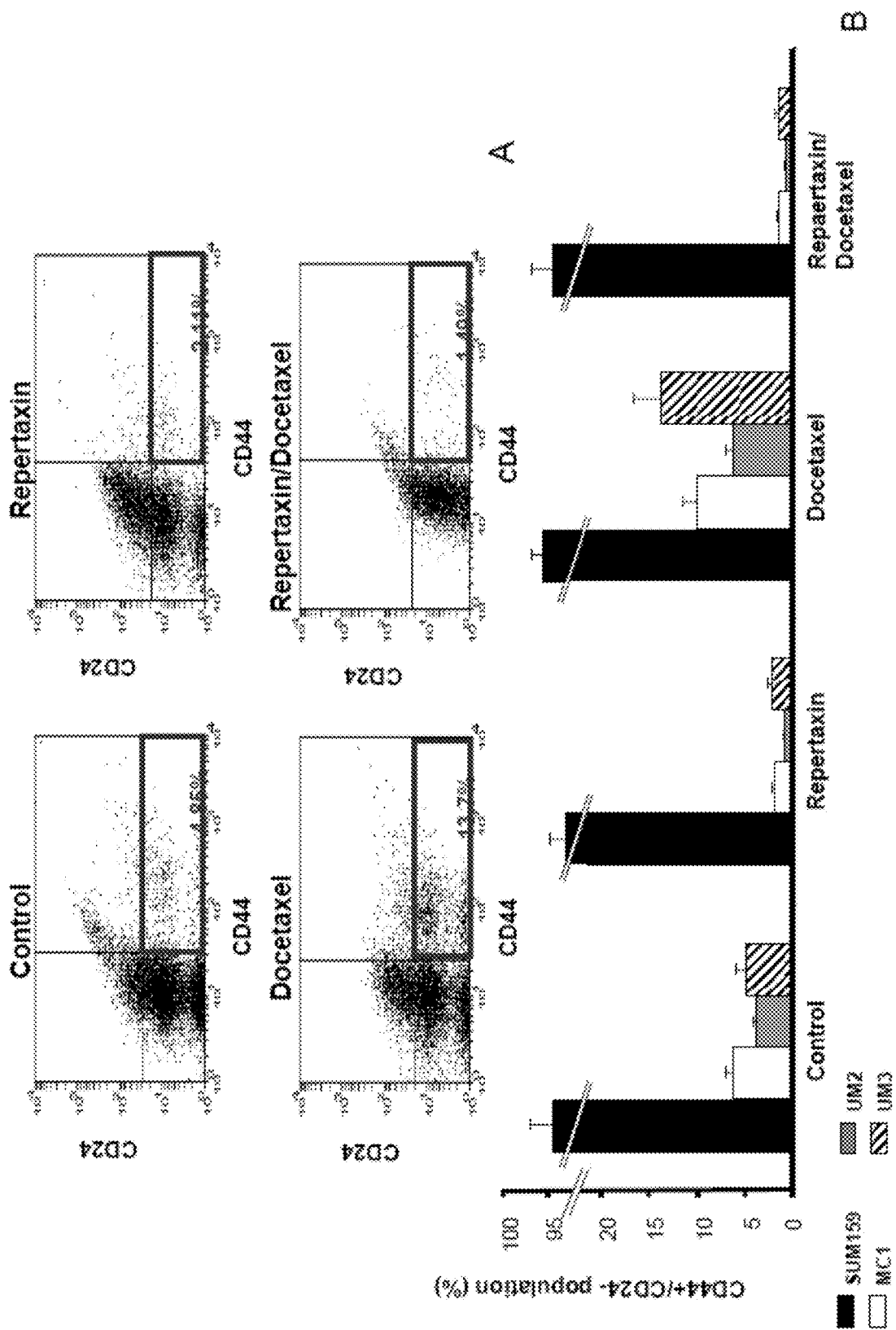

FIG. 28 shows the effect of repertaxin treatment on the breast cancer stem cell population as assessed by the CD44+/CD24− phenotype. A-B. Evaluation of repertaxin, docetaxel, or the combined treatment on the cancer stem cell population was assessed by the presence of CD44+/CD24− cells. In residual tumors treated with docetaxel alone, we consistently observed either an unchanged or increased percent of CD44+/CD24− cells whereas repertaxin treatment alone or in combination with docetaxel resulted in a reduction of the CD44+/CD24− cell population. A. Flow chart analysis for UM3 xenograft is presented. B. Similar results were observed for MC1, UM2, and UM3. Almost all of SUM159 cells are CD44+/CD24− under all treatment conditions.

Figure 29:
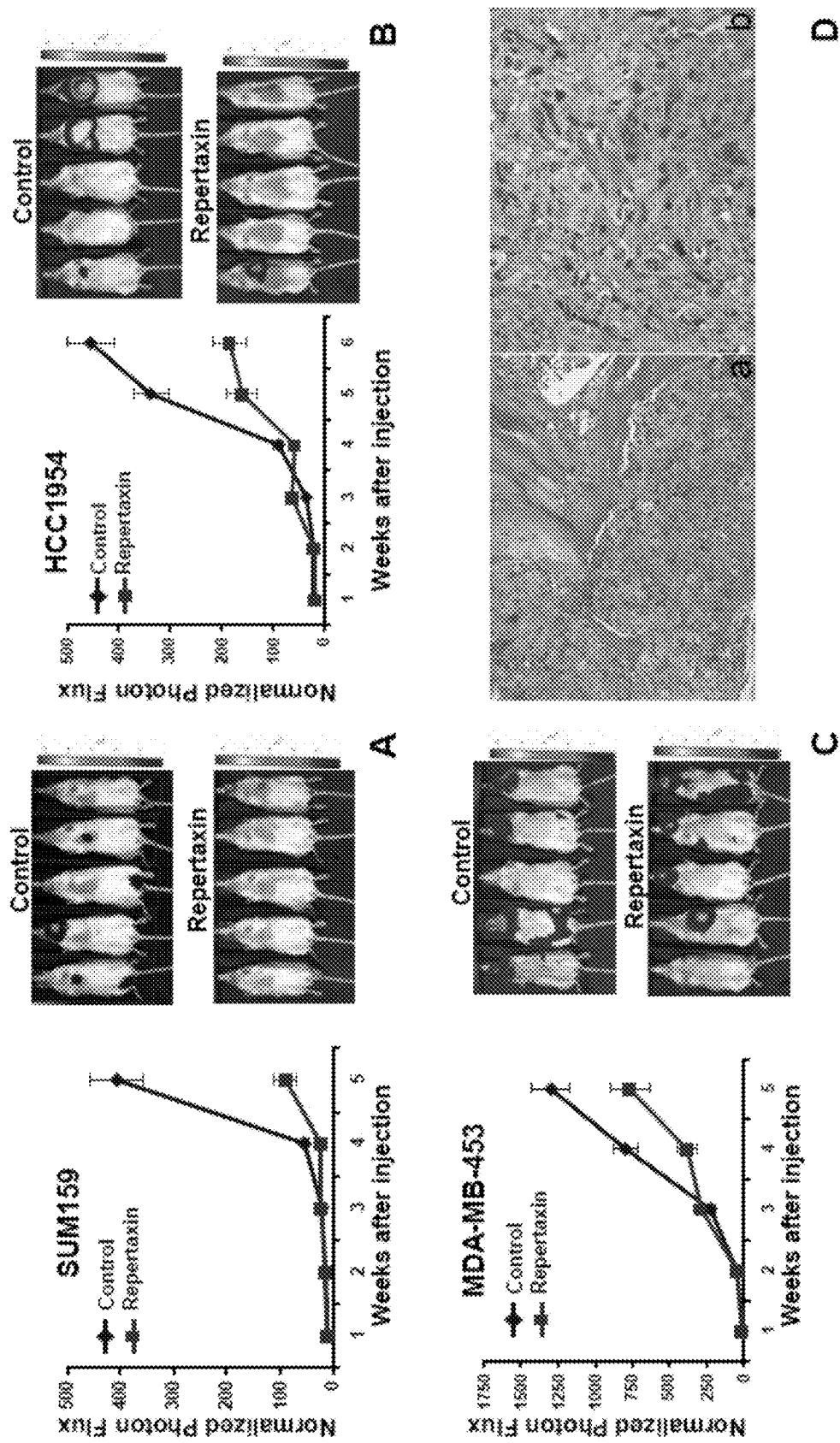

FIG. 29 shows repertaxin treatment reduces the development of systemic metastasis. To evaluate the effect of repertaxin treatment on metastasis formation HCC1954 (A), SUM159 (B), MDA-MB-453 (C) breast cancer cell lines were infected with a lentivirus expressing luciferase and inoculated 250,000 luciferase infected cells into NOD/SCID mice via intracardial injection. Mice were treated 12 hours after the intracardiac injection either with s.c. injection of saline solution or s.c. injection of repertaxin (15 mg/kg), twice a day during 28 days. Metastasis formation was monitored using bioluminescence imaging. Quantification of the normalized photon flux measured at weekly intervals following inoculation revealed a statistically significant decrease in metastasis formation in repertaxin compared to saline controls for mice inoculated with HCC1954 or SUM159 cells (A-B). In contrast, repertaxin treatment did not have any effect on metastasis formation for the mice injected with MDA-MB-453 cells. (C). Histologic confirmation, by H&E staining, of metastasis in bone, and soft tissue resulting from mice not treated by repertaxin (D).

Figure 30:
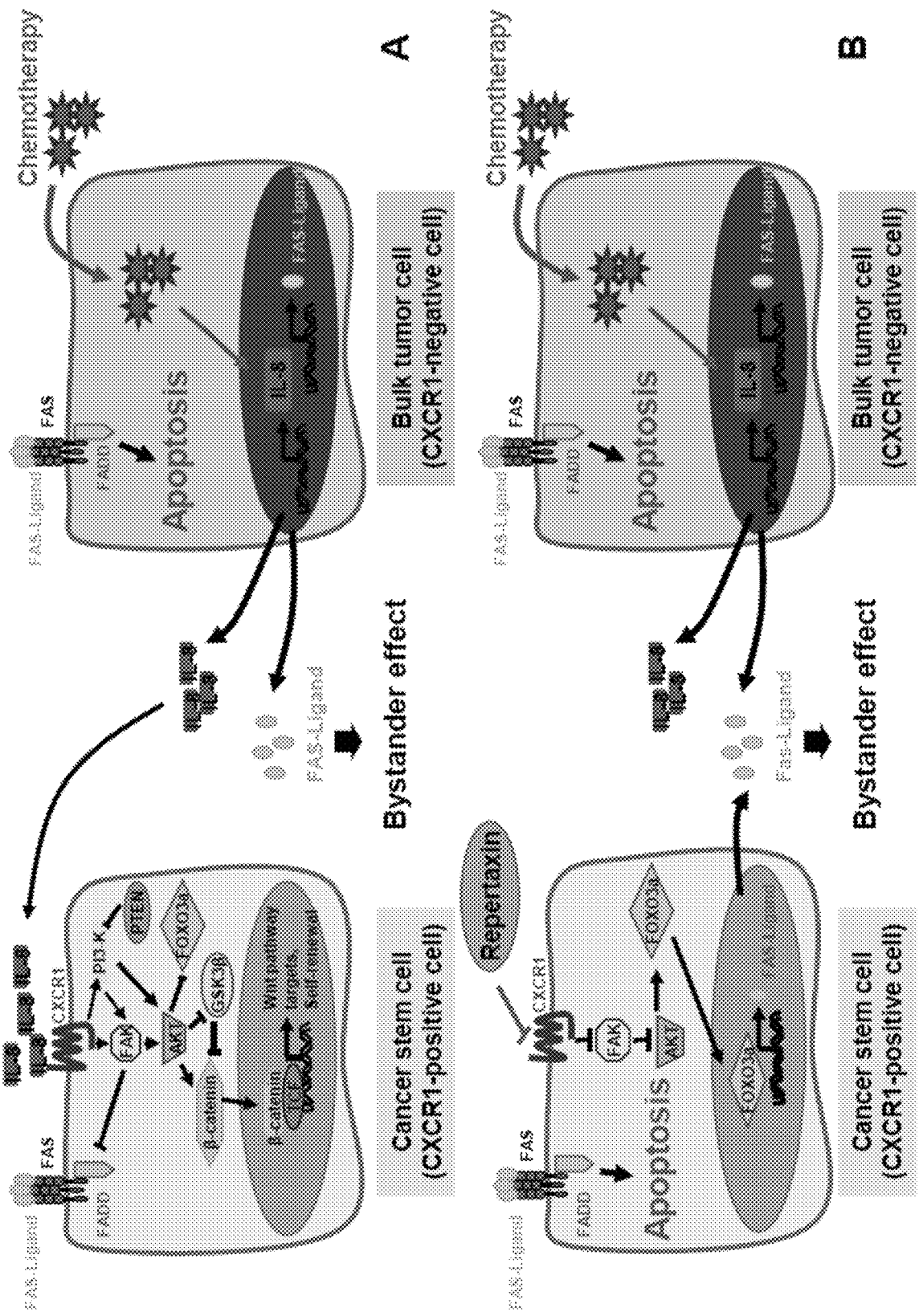

FIG. 30 shows IL-8/CXCR1 signalling in cancer stem cells treated with chemotherapy alone or in combination with repertaxin. A. Representation of potential IL-8/CXCR1 cell signaling in cancer stem cells. CXCR1 activation following IL-8 binding induces phosphorylation of the Focal Adhesion Kinase (FAK). Active FAK phosphorylates AKT and activates the WNT pathway, which regulates stem cell self renewal and FOXO3A that regulates cell survival. Activation of FAK protects cancer stem cells from a FAS-ligand/FAS mediated bystander effect by inhibiting FADD, a downstream effector of FAS signaling. In the presence of chemotherapy, only the bulk tumor cells are sensitive to the treatment and release a high level of IL-8 and FAS-ligand proteins during the apoptotic process. Breast cancer stem cells are stimulated via an IL-8 mediated bystander effect and are resistant to the bystander killing effect mediated via FAS-ligand. B. Repertaxin treatment blocks IL-8/CXCR1 signaling and inhibits breast cancer stem cell self-renewal and survival. When repertaxin treatment is combined with chemotherapy the cancer stem cells are sensitized to the bystander killing effect mediated by FAS-ligand.

DEFINITIONS

To facilitate an understanding of the present invention, a number of terms and phrases are defined below:

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

An "effective amount" is an amount sufficient to effect beneficial or desired results. An effective amount can be administered in one or more administrations.

As used herein, the term "administration" refers to the act of giving a drug, prodrug, antibody, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Coadministration" refers to administration of more than one chemical agent or therapeutic treatment (e.g., radiation therapy) to a physiological system (e.g., a subject or in vivo, in vitro, or ex vivo cells, tissues, and organs). "Coadministration" of the respective chemical agents (e.g. IL8-CXCR1 signaling pathway antagonist and additional chemotherapeutic) may be concurrent, or in any temporal order or physical combination.

As used herein, the term "regression" refers to the return of a diseased subject, cell, tissue, or organ to a nonpathological, or less pathological state as compared to basal nonpathogenic exemplary subject, cell, tissue, or organ. For example, regression of a tumor includes a reduction of tumor mass as well as complete disappearance of a tumor or tumors.

As used herein the term, "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "subject" or "patient" refers to organisms to be treated by the methods of the present invention. Such organisms include, but are not limited to, humans and veterinary animals (dogs, cats, horses, pigs, cattle, sheep, goats, and the like). In the context of the invention, the term "subject" or "patient" generally refers to an individual who will receive or who has received treatment.

The term "diagnosed," as used herein, refers to the recognition of a disease by its signs and symptoms or genetic analysis, pathological analysis, histological analysis, and the like.

As used herein, the term "antisense" is used in reference to nucleic acid sequences (e.g., RNA, phosphorothioate DNA) that are complementary to a specific RNA sequence (e.g., mRNA). Included within this definition are natural or synthetic antisense RNA molecules, including molecules that regulate gene expression, such as small interfering RNAs or micro RNAs. One type of antisense sequence that may be employed by the present invention is the type that are specific for CXCR1 mRNA.

The term "test compound" or "candidate compound" refers to any chemical entity, pharmaceutical, drug, and the like, that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are anticancer agents. In particularly preferred embodiments, "test compounds" are anticancer agents that induce apoptosis in cells.

As used herein, the term "antigen binding protein" refers to proteins which bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibodies, various host animals can be immunized by injection with the peptide corresponding to the desired epitope including, but not limited to, rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 (1975)), as well as the trioma technique, the human B-cell hybridoma technique (See e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 (1989)) to allow rapid and easy identification of monoclonal Fab fragments with the desired specificity.

Antibody fragments that contain the idiotype (antigen binding region) of the antibody molecule can be generated by known techniques. For example, such fragments include, but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein, the term "modulate" refers to the activity of a compound to affect (e.g., to promote or retard) an aspect of the cellular function including, but not limited to, cell growth, proliferation, invasion, angiogenesis, apoptosis, and the like.

DETAILED DESCRIPTION OF THE INVENTION

The present invention provides methods of treating cancer by administering an IL8-CXCR1 pathway inhibitor (e.g., an anti-CXCR1 antibody or Repertaxin) alone or in combination with an additional chemotherapeutic agent such that non-tumorigenic and tumorigenic cancer cells in a subject are killed. The present invention also provides compositions and methods for treating and diagnosing the presence of solid tumor stem cells in a patient (e.g., based on the presence of CXCR1 or FBXO21).

I. Tumorigenic Cancer Cells, ALDH, CXCR1, and CXCR1 Inhibition

The evolution of a normal cell into a fully transformed one requires the deregulation of multiple cellular processes (1, 2). According to classical models of carcinogenesis, these events can occur in any cell. In contrast, the "cancer stem cell hypothesis" holds that the preferential targets of oncogenic transformation are tissue stem or early progenitor cells that have acquired self-renewal potential (3-6). These "tumor-initiating cells" or "cancer stem cells" (CSC), in turn, are characterized by their ability to undergo self-renewal, a process that drives tumorigenesis and differentiation which contributes to tumor cellular heterogeneity. Recent evidence supporting the cancer stem cell hypothesis has been generated utilizing xenografts of primary human tumors. These studies have suggested that tumors are composed of a cellular hierarchy driven by the cancer stem cell component. In addition, recent data suggest that immortalized cell lines derived from both murine and human tissues may also contain a cellular population displaying stem cell properties. Most of these studies have been based on in vitro properties including clonogenic potential, sphere formation and multi-lineage differentiation potential (7-10). More limited studies utilizing functional transplantation of immortalized cell lines in xenografts have also suggested the existence of such a hierarchy. These studies have generally utilized Hoechst dye exclusion to identify the so-called "side population" (SP) (7, 9, 11). In addition, cell surface markers defined using primary tumor xenografts such as CD44 and CD133 have also been utilized to identify similar populations in established cell lines (7, 8).

As described in the Examples below, the expression of the stem cell marker Aldehyde dehydrogenase (ALDH) was studied in a series of 33 cell lines derived from human breast cancers and non-transformed breast cells. ALDH is a detoxifying enzyme responsible for the oxidation of intracellular aldehydes and is thought to play a role in stem cell differentiation through metabolism of retinal to retinoic acid (12, 13). ALDH activity as assessed by the fluorescent ALDEFLUOR assay has been successfully utilized to isolate cancer stem cells in multiple myeloma and acute myeloid leukemia (AML) as well as from brain tumors (14-16). It was recently demonstrated that ALDH activity can be utilized to isolate a subpopulation of cells that display stem cell properties from normal human breast tissue and breast carcinomas (17). The ALDEFLUOR-positive population isolated from reduction mammoplasty tissue is able to reconstitute ductal alveolar structures in mammary fat pads of humanized NOD/SCID mice. Furthermore, ALDEFLUOR-positive cells isolated from human mammary carcinomas have stem cell properties as demonstrated by their ability to reconstitute tumors on serial passage in NOD/SCID mice as well as to generate the phenotypic heterogeneity of the initial tumors (17). In the Examples below, it is demonstrated that the majority of breast cancer cell lines contain an ALDEFLUOR-positive population with a distinct molecular profile that displays cancer stem cell properties.

As described in the Examples below, work conducted during the development of embodiments of the present invention identified CXCR1 (which is a receptor for the inflammatory chemokine IL8) as a cancer stem cell marker. Only cells within the Aldefluor-positive population expressed CXCR1. Furthermore, it was demonstrated that this receptor plays a functional role in that recombinant IL8 is able to increase the stem cell proportion in cell lines as determined by Aldefluor and sphere formation assays. Although IL8 has been reported to be associated with aggressive breast cancers and is higher in the serum women with metastatic disease, it is believe that the present invention is the first to show a functional link between IL8 and its receptor CXCR1 in stem cells.

As further described in the Examples below, it was demonstrated that one can selectively target cancer stem cells by blocking the CXCR1 receptor in these cells. In one approach described in the Examples, breast cancer cells lines were treated with monoclonal antibodies to CXCR1, but not to the other IL8 receptor CXCR2. Such treatment selectively targeted cancer stem cells as demonstrated by reduced Aldefluor-positive populations. Remarkably, it found that although CXCR1 is only expressed in a very small percentage of cells (e.g., less than 1%), that blockade of the CXCR1 receptor induced cell death in the majority of other cancer cells despite the fact that they lack the CXCR1 receptor. The molecular pathway which mediates the effects of IL on cancer stem cells and accounts for this so-called "bystander effect" of killing other cells has been elucidated. IL8 stimulates stem cell self-renewal by binding to CXCR1, which in turn activates the focal adhesion kinase Fak pathway. This results in activation of Akt which drives stem cell self-renewal. When this pathway is blocked in cancer stem cells, the decrease in Akt signaling causes cytoplasmic sequestration of the Foxo transcription factors resulting in an increased synthesis of Fas ligand. Fas ligand is secreted from cancer stem cells and induces cell death in surrounding cells which contain the Fas receptor.

While the present invention is not limited to any particular mechanism, and an understanding of the mechanism is not necessary to practice the present invention, it is believed that CXCR1 mediates cancer stem cell self-renewal through a pathway involving Fak and Akt and that blockade of this pathway induces cell death in cancer stem cells as well as surrounding tumor cells. As such, in certain embodiments, the present invention provides compositions and methods for disrupting the IL8-CXCR1 pathway (e.g., with anti-CXCR1 antibodies, anti-FAK antibodies, or other agents) in order to treat cancer.

Since IL8 is a chemokine involved in tissue inflammation, there has been previous interest in developing inhibitors of IL8 signaling. A small molecule inhibitor, Repartaxin, has been developed as an anti-inflammatory agent to potentially reduce complications of myocardial infarction and stroke. Repartaxin has been introduced into phase I and phase II clinical trials and has shown little toxicity. As shown in the Examples below, Repartaxin (like anti-CXCR1 antibodies) is able to target cancer stem cells as well as to induce a Fas ligand fas mediated apoptosis by bystander effect in surrounding cells. Importantly, in tumor xenografts, Repartaxin potentiates the effect of chemotherapy. Furthermore, unlike chemotherapy, which preferentially destroys the differentiated cells in tumors sparing the tumor stem cells, Repartaxin is able to target tumor stem cells. As shown in the examples, this was demonstrated by a decrease in the Aldefluor population in Repartaxin treated tumors and by the decrease in ability of these treated tumor cells to form secondary tumors in mice. Also tested was the effects of Repartaxin on the ability to block metastasis. Tumor cells were labeled with luciferase and injected intracardiac in an experimental metastasis model. One day after the tumor cells were introduced, one group of animals was placed on repartaxin alone and the other no treatment. Repartaxin significantly reduced the development of metastasis.

The present invention identified the IL8 receptor CXCR1 as a target in treating cancer stem cells. The small molecule inhibitor Repartaxin inhibits both CXCR1 and CXCR2. The Examples demonstrated that it is CXCR1 that is the most important receptor in cancer stem cells. Furthermore, the Examples indicate that the failure of cytotoxic chemotherapy to affectively treat established cancers may be not only due to the inability of this therapy to target cancer stem cells, but in addition to the documented increase of IL8 secretion upon tumor cytotoxic chemotherapy treatment. The present Examples indicate that the use of CXCR1 inhibitors have beneficial effects in being able to specifically target cancer stem cells as well as to block the IL8 stimulation of these cells induced by cytotoxic chemotherapy.

Targeting the IL8-CXCR1 pathway is not limited to breast cancer, but instead, can be employed in any type of cancer. Preferably, the type of cancer treated is one where there is evidence of increased IL8 production (e.g., in conjunction with chemotherapy). Chemotherapy agents have been shown to directly regulate IL8 transcription in cancer cells. Paclitaxel increases IL8 transcription and secretion in ovarian, breast and lung cancer cell lines (Uslu et al., 2005, Int. J. Gynecol. Cancer, 15:240-245; and Collins et al., 2000, Can. Imm. Immuno., 49:78-84, both of which are herein incorporated by reference). Also, administration of adriamycin and 5-fluoro-2'-deoxyuridine to breast cancer cells (DeLarco et al., 2001, Can. Res. 61:2857-2861, herein incorporated by reference), the addition of 5-FU to oral cancer cells (Tamatani et al., 2004, Int., J. Can., 108:912: 921, herein incorporated by reference), doxorubicin addition to small cell lung cancer cells (Shibakura et al., 2003, Int. J. Can., 103:380-386, herein incorporated by reference) and dacarbazine administration to melanoma cells (Lev et al., 2003, Mol., Can. Ther., 2:753-763, herein incorporated by reference) all result in increased CXCL8 expression. As such, in certain embodiments, the present invention provides agents for targeting the IL-CXCR1, in combination with a chemotherapy agents (e.g., such as those mentioned in the above references) for treating a subject with a type of cancer including, but not limited to, prostate cancer, ovarian cancer, breast cancer, melanoma, non-small cell lung cancer, small-cell lung cancer, and esophageal adenocarcinoma.

The present invention is not limited to the type of cancer treated and instead includes, but is not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

II. Detection of Solid Tumor Stem Cell Cancer Markers

In some embodiments, the present invention provides methods for detection of expression of stem cell cancer markers (e.g., CXCR1, FBXO21, NFYA, NOTCH2, RAD51L1, TBP, and other proteins from Table 1). In some embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine).

The present invention further provides panels and kits for the detection of markers. In some embodiments, the presence of a stem cell cancer marker is used to provide a prognosis to a subject. The information provided is also used to direct the course of treatment. For example, if a subject is found to have a marker indicative of a solid tumor stem cell (e.g., CXCR1, FBXO21, NFYA, NOTCH2, RAD51L1, TBP, and other proteins from Table 1), additional therapies (e.g., radiation therapies) can be started at an earlier point when they are more likely to be effective (e.g., before metastasis). In addition, if a subject is found to have a tumor that is not responsive to certain therapy, the expense and inconvenience of such therapies can be avoided.

In some embodiments, the present invention provides a panel for the analysis of a plurality of markers (e.g., the combination of CXCR1 or FBXO21 and at least one of CD44, CD24, and ESA). The panel allows for the simultaneous analysis of multiple markers correlating with carcinogenesis and/or metastasis. Depending on the subject, panels can be analyzed alone or in combination in order to provide the best possible diagnosis and prognosis. Markers for inclusion on a panel are selected by screening for their predictive value using any suitable method, including but not limited to, those described in the illustrative examples below.

1. Detection of RNA

In some embodiments, detection of solid tumor stem cell cancer markers are detected by measuring the expression of corresponding mRNA in a tissue sample. mRNA expression can be measured by any suitable method, including but not limited to, those disclosed below. The accession number for human CXCR1 nucleic acid is NM_000634 (herein incorporated by reference) and the accession number for human FBXO21 is NM_033624 (herein incorporated by reference). These sequences can be used to design primers and probes (as well as siRNA sequences).

In some embodiments, RNA is detected by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of stem cell cancer markers is detected by measuring the expression of the corresponding protein or polypeptide (e.g., CXCR1, FBXO21, NFYA, NOTCH2, RAD51L1, TBP, and other proteins from Table 1). Protein expression can be detected by any suitable method. In some embodiments, proteins are detected by immunohistochemistry. In other embodiments, proteins are detected by their binding to an antibody raised against the protein. The accession number for human CXCR1 protein is NP_000625 (herein incorporated by reference) and the accession number for human FBXO21 is NP_296373 (herein incorporated by reference). The generation of antibodies is described below.

Antibody binding is detected by techniques known in the art (e.g., radioimmunoassay, ELISA (enzyme linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. cDNA Microarray Technology cDNA microarrays are composed of multiple (usually thousands) of different cDNAs spotted (usually using a robotic spotting device) onto known locations on a solid support, such as a glass microscope slide. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length. Full length cDNAs, expressed sequence tags (ESTs), or randomly chosen cDNAs from any library of interest can be chosen. ESTs are partially sequenced cDNAs as described, for example, in Hillier, et al., 1996, 6:807-828. Although some ESTs correspond to known genes, frequently very little or no information regarding any particular EST is available except for a small amount of 3' and/or 5' sequence and, possibly, the tissue of origin of the mRNA from which the EST was derived. As will be appreciated by one of ordinary skill in the art, in general the cDNAs contain sufficient sequence information to uniquely identify a gene within the human genome. Furthermore, in general the cDNAs are of sufficient length to hybridize, selectively, specifically or uniquely, to cDNA obtained from mRNA derived from a single gene under the hybridization conditions of the experiment.

In a typical microarray experiment, a microarray is hybridized with differentially labeled RNA, DNA, or cDNA populations derived from two different samples. Most commonly RNA (either total RNA or poly A+RNA) is isolated from cells or tissues of interest and is reverse transcribed to yield cDNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluorophore while cDNA derived from a second sample (representing, for example, a different cell type, tissue type, or growth condition) is labeled with the second fluorophore. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

Each microarray experiment can provide tens of thousands of data points, each representing the relative expression of a particular gene in the two samples. Appropriate organization and analysis of the data is of key importance, and various computer programs that incorporate standard statistical tools have been developed to facilitate data analysis. One basis for organizing gene expression data is to group genes with similar expression patterns together into clusters. A method for performing hierarchical cluster analysis and display of data derived from microarray experiments is described in Eisen et al., 1998, PNAS 95:14863-14868. As described therein, clustering can be combined with a graphical representation of the primary data in which each data point is represented with a color that quantitatively and qualitatively represents that data point. By converting the data from a large table of numbers into a visual format, this process facilitates an intuitive analysis of the data. Additional information and details regarding the mathematical tools and/or the clustering approach itself can be found, for example, in Sokal & Sneath, Principles of numerical taxonomy, xvi, 359, W. H. Freeman, San Francisco, 1963; Hartigan, Clustering algorithms, xiii, 351, Wiley, New York, 1975; Paull et al., 1989, J. Natl. Cancer Inst. 81:1088-92; Weinstein et al. 1992, Science 258:447-51; van Osdol et al., 1994, J. Natl. Cancer Inst. 86:1853-9; and Weinstein et al., 1997, Science, 275:343-9.

Further details of the experimental methods used in the present invention are found in the Example below. Additional information describing methods for fabricating and using microarrays is found in U.S. Pat. No. 5,807,522, which is herein incorporated by reference. Instructions for constructing microarray hardware (e.g., arrayers and scanners) using commercially available parts. Additional discussions of microarray technology and protocols for preparing samples and performing microarray experiments are found in, for example, DNA arrays for analysis of gene expression, Methods Enzymol, 303:179-205, 1999; Fluorescence-based expression monitoring using microarrays, Methods Enzymol, 306: 3-18, 1999; and M. Schena (ed.), DNA Microarrays: A Practical Approach, Oxford University Press, Oxford, UK, 1999.

4. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject can visit a medical center to have the sample obtained and sent to the profiling center, or subjects can collect the sample themselves and directly send it to a profiling center. Where the sample comprises previously determined biological information, the information can be directly sent to the profiling service by the subject (e.g., an information card containing the information can be scanned by a computer and the data transmitted to a computer of the profiling center using an electronic communication system). Once received by the profiling service, the sample is processed and a profile is produced (e.g., expression data), specific for the diagnostic or prognostic information desired for the subject.

The profile data is then prepared in a format suitable for interpretation by a treating clinician. For example, rather than providing raw expression data (e.g. examining a number of the markers), the prepared format can represent a diagnosis or risk assessment for the subject, along with recommendations for particular treatment options. The data can be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject can chose further intervention or counseling based on the results. In some embodiments, the data is used for research use. For example, the data can be used to further optimize the inclusion or elimination of markers as useful indicators of a particular condition or stage of disease.

5. Kits

In yet other embodiments, the present invention provides kits for the detection and characterization of cancer (e.g. for detecting one or more of the markers, or for modulating the activity of a peptide expressed by one or more of markers). In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In some embodiments, the kits contain all of the components necessary and/or sufficient to perform a detection assay, including all controls, directions for performing assays, and any necessary software for analysis and presentation of results.

Another embodiment of the present invention comprises a kit to test for the presence of the polynucleotides or proteins. The kit can comprise, for example, an antibody for detection of a polypeptide or a probe for detection of a polynucleotide. In addition, the kit can comprise a reference or control sample; instructions for processing samples, performing the test and interpreting the results; and buffers and other reagents necessary for performing the test. In other embodiments the kit comprises pairs of primers for detecting expression of one or more of the genes of the solid tumor stem cell gene signature. In other embodiments the kit comprises a cDNA or oligonucleotide array for detecting expression of one or more of the genes of the solid tumor stem cell gene signature.

6. In Vivo Imaging

In some embodiments, in vivo imaging techniques are used to visualize the expression of cancer markers in an animal (e.g., a human or non-human mammal). For example, in some embodiments, cancer marker mRNA (e.g., CXCR1 or FBXO21 mRNA) or protein (e.g., CXCR1 or FBXO21 protein) is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the solid tumor stem cell cancer markers of the present invention. In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancer stem cells can be detected. The in vivo imaging methods of the present invention can further be used to detect metastatic cancers in other parts of the body.

In some embodiments, reagents (e.g., antibodies) specific for CXCR1 or FBXO21 are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having pancreatic cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents can also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement can be achieved by effecting radiolabeling in the presence of the specific stem cell cancer marker of the present invention, to insure that the antigen binding site on the antibody will be protected.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

III. Antibodies and Antibody Fragments

The present invention provides isolated antibodies and antibody fragments against CXCR1, FBXO21, NFYA, NOTCH2, RAD51L1, TBP, and other proteins from Table 1. The antibody, or antibody fragment, can be any monoclonal or polyclonal antibody that specifically recognizes these proteins. In some embodiments, the present invention provides monoclonal antibodies, or fragments thereof, that specifically bind to CXCR1, FBXO21, NFYA, NOTCH2, RAD51L1, TBP, and other proteins from Table 1. In some embodiments, the monoclonal antibodies, or fragments thereof, are chimeric or humanized antibodies that specifically bind to these proteins. In other embodiments, the monoclonal antibodies, or fragments thereof, are human antibodies that specifically bind to these proteins.

The antibodies against CXCR1, FBXO21, NFYA, NOTCH2, RAD51L1, TBP, and other proteins from Table 1 find use in the experimental, diagnostic and therapeutic methods described herein. In certain embodiments, the antibodies of the present invention are used to detect the expression of a cancer stem cell marker protein in biological samples such as, for example, a patient tissue biopsy, pleural effusion, or blood sample. Tissue biopsies can be sectioned and protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of a cancer stem cell marker, for example, on tumor cells, in cell lysates, or in other protein samples. In other embodiments, the antibodies of the present invention are used to inhibit the growth of tumor cells by contacting the antibodies with tumor cells either in vitro cell based assays or in vivo animal models. In still other embodiments, the antibodies are used to treat cancer in a human patient by administering a therapeutically effective amount of an antibody against a cancer stem cell marker (e.g., from Table 1).

Polyclonal antibodies can be prepared by any known method. Polyclonal antibodies can be raised by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against a cancer stem cell marker is a humanized antibody. Humanized antibodies are antibodies that contain minimal sequences from non-human (e.g., murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize cancer stem cell markers. Bispecific antibodies are antibodies that are capable of specifically recognizing and binding at least two different epitopes.

Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp.

Med. 175:217-225; Kostelny et al., 1992, J. Immunol. 148:1547-1553; Gruber et al., 1994, J. Immunol. 152:5368; and U.S. Pat. No. 5,731,168).

In certain embodiments of the invention, it may be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes. A variety of radionuclides are available for the production of radioconjugated antibodies including 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC 1065, and the derivatives of these toxins that have toxin activity, can also be used.

In some embodiments the antibody of the invention contains human Fc regions that are modified to enhance effector function, for example, antigen-dependent cell-mediated cytotoxicity (ADCC) and/or complement dependent cytotoxicity (CDC). This can be achieved by introducing one or more amino acid substitutions in an Fc region of the antibody. For example, cysteine residue(s) can be introduced in the Fc region to allow interchain disulfide bond formation in this region to improve complement-mediated cell killing and antibody-dependent cellular cytotoxicity (ADCC) (Caron et al., 1992, J. Exp Med. 176:1191-1195; Shopes, 1992, Immunol. 148:2918-2922). Homodimeric antibodies with enhanced anti-tumor activity can also be prepared using heterobifunctional cross-linkers as described in Wolff et al., 1993, Cancer Research 53:2560-2565. Alternatively, an antibody can be engineered which has dual Fc regions (Stevenson et al., 1989, Anti-Cancer Drug Design 3:219-230).

IV. Drug Screening

In some embodiments, the present invention provides drug screening assays (e.g., to screen for anticancer drugs). The screening methods of the present invention utilize stem cell cancer markers (e.g., CXCR1, FBXO21, NFYA, NOTCH2, RAD51L1, TBP, and other proteins from Table 1) identified using the methods of the present invention. For example, in some embodiments, the present invention provides methods of screening for compounds that alter (e.g., increase or decrease) the expression of, or activity of, CXCR1 or FBXO21. In some embodiments, candidate compounds are antisense agents or siRNA agents (e.g., oligonucleotides) directed against cancer markers. In other embodiments, candidate compounds are antibodies that specifically bind to a stem cell cancer marker of the present invention. In certain embodiments, libraries of compounds of small molecules are screened using the methods described herein.

In one screening method, candidate compounds are evaluated for their ability to alter stem cell cancer marker expression by contacting a compound with a cell expressing a stem cell cancer marker and then assaying for the effect of the candidate compounds on expression. In some embodiments, the effect of candidate compounds on expression of a cancer marker gene is assayed by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein. In some embodiments, other changes in cell biology (e.g., apoptosis) are detected.

Specifically, the present invention provides screening methods for identifying modulators, i.e., candidate or test compounds or agents (e.g., proteins, peptides, peptidomimetics, peptoids, small molecules or other drugs) which bind to, or alter the signaling or function associated with the cancer markers of the present invention, have an inhibitory (or stimulatory) effect on, for example, stem cell cancer marker expression or cancer markers activity, or have a stimulatory or inhibitory effect on, for example, the expression or activity of a cancer marker substrate. Compounds thus identified can be used to modulate the activity of target gene products (e.g., stem cell cancer marker genes, such as CXCR1 or FBXO21) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic cancer or eliminating or controlling tumor stem cells to prevent or reduce the risk of cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds can be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a stem cell cancer marker protein or biologically active portion thereof is contacted with a test compound, and the ability of the test compound to the modulate cancer marker's activity is determined. Determining the ability of the test compound to modulate stem cell cancer marker activity can be accomplished by monitoring, for example, changes in enzymatic activity. The cell, for example, can be of mammalian origin.

The ability of the test compound to modulate cancer marker binding to a compound, e.g., a stem cell cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the stem cell cancer marker is coupled with a radioisotope or enzymatic label to monitor the ability of a test compound to modulate cancer marker binding to a cancer markers substrate in a complex. For example, compounds (e.g., substrates) can be labeled with 125I, 35S 14C or 3H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a stem cell cancer marker substrate) to interact with a stem cell cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the stem cell cancer marker protein or biologically active portion thereof is evaluated. Biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the stem cell cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. The target gene product can be anchored onto a solid surface, and the test compound, (which is not anchored), can be labeled, either directly or indirectly, with detectable labels discussed herein.

It may be desirable to immobilize stem cell cancer markers, an anti-cancer marker antibody or its target molecule to facilitate separation of complexed from non-complexed forms of one or both of the proteins, as well as to accommodate automation of the assay. Binding of a test compound to a stem cell cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with stem cell cancer marker protein or target molecules but which do not interfere with binding of the stem cell cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-525 [1997]). Further, fluorescence energy transfer can also be conveniently utilized, as described herein, to detect binding without further purification of the complex from solution.

The assay can include contacting the stem cell cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that stem cell cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of stem cell cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein (e.g. to treat a human patient who has cancer).

In certain embodiments, the present invention employs non-adherent mammospheres for various screening procedures, including methods for screening CXCR1 or FBXO21 signaling pathway antagonists. Non-adherent mammospheres are an in vitro culture system that allows for the propagation of primary human mammary epithelial stem and progenitor cells in an undifferentiated state, based on their ability to proliferate in suspension as spherical structures. Non-adherent mammospheres have previously been described in Dontu et al Genes Dev. 2003 May 15; 17(10):1253-70, and Dontu et al., Breast Cancer Res. 2004; 6(6): R605-15, both of which are herein incorporated by reference. These references are incorporated by reference in their entireties and specifically for teaching the construction and use of non-adherent mammospheres. As described in Dontu et al., mammospheres have been characterized as being composed of stem and progenitor cells capable of self-renewal and multi-lineage differentiation. Dontu et al. also describes that mammospheres contain cells capable of clonally generating complex functional ductal-alveolar structures in reconstituted 3-D culture systems in Matrigel.

In certain embodiments, the following exemplary screening methods are employed. For in vitro studies, one could treat cells with either adenoviral constructs expressing control or CXCR1 or FBXO21 candidate siRNA (m.o.i. 10 to 100) for 3 days or a small molecule candidate (e.g., PHA665752 derivative) (0.1-0.5 uM) for 3 days and compare the ability of CXCR1+ or FBXO21+ cells to form tumor spheres compared in untreated vs. treated cells. For in vivo studies, one could infect human breast cancer cells with a lentivirus expressing luciferase to monitor tumor growth. Luciferase-expressing cancer cells could be injected into breast tissue and tumors of approximately 0.5-0.7 cm in size could be established, with 5 animals per group. Animals with established tumors could then be treated with either a candidate CXCR1 or FBXO21 inhibitor (daily i.v. 30 mg/kg/day for 7 days), or vehicle control. Parallel studies could be performed using infection with adenovirus expressing control or candidate CXCR1 or FBXO21 siRNA (m.o.i. 100 or 500 for 7 days). Animals could be imaged at day 7, 14, 21, and 28 to assess tumor size and then be sacrificed. Tumor size could be further assessed at autopsy and a portion of the tumor stained to assess tumor histology. The remaining tumor could be harvested and sorted to assess the percentage of CXCR1 or FBXO21 positive and CXCR1 or FBXO21 negative cells. To verify that administration of candidate CXCR1 or FBXO21 inhibitor and candidate CXCR1 or FBXO21 siRNA adenovirus infection is inhibiting CXCR1 or FBXO21 signaling function, phosphorylation of downstream mediators such as Gab-1 and ERK could be examined (see, Chistensen et al., Cancer Res., 2003; 63:7345-7355, herein incorporated by reference).

V. Cancer Therapies

In some embodiments, the present invention provides therapies for cancer. In some embodiments, therapies target cancer markers (e.g., including but not limited to, CXCR1 or FBXO21 and proteins in the CXCR1 or FBXO21 signaling pathway). In some embodiments, any known or later developed cancer stem cell therapy may be used. For example, cancer stem cell therapeutic agents are described in U.S. Pat. Nos. 6,984,522 and 7,115,360 and applications WO03/050502, WO05/074633, and WO05/005601, herein incorporated by reference in their entireties.

Antibody Therapy

In some embodiments, the present invention provides antibodies that target tumors that express a stem cell cancer marker of the present invention. Any suitable antibody (e.g., monoclonal, polyclonal, or synthetic) can be utilized in the therapeutic methods disclosed herein. In some embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a stem cell cancer marker of the present invention, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention can include a variety of cytotoxic moieties, including but not limited to, radioactive isotopes (e.g., iodine-131, iodine-123, technetium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments can include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some embodiments, deglycosylated ricin A chain is utilized.

In any event, it is proposed that agents such as these can, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted at stem cell cancer marker of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In some embodiments, antibody based therapeutics are formulated as pharmaceutical compositions as described below. In some embodiments, administration of an antibody composition of the present invention results in a measurable decrease in cancer (e.g., decrease or elimination of tumor).

VI. Therapeutic Compositions and Administration

A pharmaceutical composition containing a regulator of tumorigenesis according the present invention can be administered by any effective method. For example, an IL8-CXCR1 signaling pathway antagonist, or other therapeutic agent that acts as an antagonist of proteins in the IL8-CXCR1 signal transduction/response pathway can be administered by any effective method. In certain embodiments of the present invention, the therapeutic agent comprises Repertaxin or a derivative thereof.

In certain embodiments, a physiologically appropriate solution containing an effective concentration of an IL8-CXCR1 signaling pathway antagonist can be administered topically, intraocularly, parenterally, orally, intranasally, intravenously, intramuscularly, subcutaneously or by any other effective means. In particular, the IL8-CXCR1 signaling pathway antagonist agent may be directly injected into a target cancer or tumor (e.g., into breast tissue) by a needle in amounts effective to treat the tumor cells of the target tissue. Alternatively, a cancer or tumor present in a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile) containing an effective concentration of an IL8-CXCR1 signaling pathway antagonist via direct injection with a needle or via a catheter or other delivery tube placed into the cancer or tumor afflicted hollow organ. Any effective imaging device such as X-ray, sonogram, or fiber-optic visualization system may be used to locate the target tissue and guide the needle or catheter tube. In another alternative, a physiologically appropriate solution containing an effective concentration of an IL8-CXCR1 signaling pathway antagonist can be administered systemically into the blood circulation to treat a cancer or tumor that cannot be directly reached or anatomically isolated.

Such manipulations have in common the goal of placing the IL8-CXCR1 signaling pathway antagonist in sufficient contact with the target tumor to permit the antagonist to contact, transduce or transfect the tumor cells (depending on the nature of the agent). In one embodiment, solid tumors present in the epithelial linings of hollow organs may be treated by infusing the suspension into a hollow fluid filled organ, or by spraying or misting into a hollow air filled organ. Thus, the tumor cells (such as a solid tumor stem cells) may be present in or among the epithelial tissue in the lining of pulmonary bronchial tree, the lining of the gastrointestinal tract, the lining of the female reproductive tract, genitourinary tract, bladder, the gall bladder and any other organ tissue accessible to contact with the IL8-CXCR1 signaling pathway antagonist. In another embodiment, the solid tumor may be located in or on the lining of the central nervous system, such as, for example, the spinal cord, spinal roots or brain, so that the IL8-CXCR1 signaling pathway antagonist infused in the cerebrospinal fluid contacts and transduces the cells of the solid tumor in that space. One skilled in the art of oncology can appreciate that the antagonist can be administered to the solid tumor by direct injection into the tumor so that the antagonist contacts and affects the tumor cells inside the tumor.

The tumorigenic cells identified by the present invention can also be used to raise anti-cancer cell antibodies. In one embodiment, the method involves obtaining an enriched population of tumorigenic cells or isolated tumorigenic cells; treating the population to prevent cell replication (for example, by irradiation); and administering the treated cell to a human or animal subject in an amount effective for inducing an immune response to solid tumor stem cells. For guidance as to an effective dose of cells to be injected or orally administered; see, U.S. Pat. Nos. 6,218,166, 6,207,147, and 6,156,305, incorporated herein by reference. In another embodiment, the method involves obtaining an enriched population of solid tumor stem cells or isolated solid tumor stem cells; mixing the tumor stem cells in an in vitro culture with immune effector cells (according to immunological methods known in the art) from a human subject or host animal in which the antibody is to be raised; removing the immune effector cells from the culture; and transplanting the immune effector cells into a host animal in a dose that is effective to stimulate an immune response in the animal.

In some embodiments of the present invention, the anti-tumorigenic therapeutic agents (e.g. IL8-CXCR1 signaling pathway antagonists) of the present invention are co-administered with other anti-neoplastic therapies. A wide range of therapeutic agents find use with the present invention. Any therapeutic agent that can be co-administered with the agents of the present invention, or associated with the agents of the present invention is suitable for use in the methods of the present invention.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 3 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 3

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |

TABLE 3-continued

| | | |
|---|---|---|
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |

TABLE 3-continued

| | | |
|---|---|---|
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O—(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |

TABLE 3-continued

| Drug | Brand | Company |
|---|---|---|
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl (($4S$)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |

TABLE 3-continued

| | | |
|---|---|---|
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-µ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1"-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate | Valstar | Anthra --> Medeva |

TABLE 3-continued

| | | |
|---|---|---|
| ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | | |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In still further embodiments, the present invention provides compounds of the present invention (and any other chemotherapeutic agents) associated with targeting agents that are able to specifically target particular cell types (e.g., tumor cells). Generally, the therapeutic compound that is associated with a targeting agent, targets neoplastic cells through interaction of the targeting agent with a cell surface moiety that is taken into the cell through receptor mediated endocytosis.

Any moiety known to be located on the surface of target cells (e.g., tumor cells) finds use with the present invention. For example, an antibody directed against such a moiety targets the compositions of the present invention to cell surfaces containing the moiety. Alternatively, the targeting moiety may be a ligand directed to a receptor present on the cell surface or vice versa. Similarly, vitamins also may be used to target the therapeutics of the present invention to a particular cell.

As used herein, the term "targeting molecules" refers to chemical moieties, and portions thereof useful for targeting therapeutic compounds to cells, tissues, and organs of interest. Various types of targeting molecules are contemplated for use with the present invention including, but not limited to, signal peptides, antibodies, nucleic acids, toxins and the like. Targeting moieties may additionally promote the binding of the associated chemical compounds (e.g., small molecules) or the entry of the compounds into the targeted cells, tissues, and organs. Preferably, targeting moieties are selected according to their specificity, affinity, and efficacy in selectively delivering attached compounds to targeted sites within a subject, tissue, or a cell, including specific subcellular locations and organelles.

Various efficiency issues affect the administration of all drugs—and of highly cytotoxic drugs (e.g., anticancer drugs) in particular. One issue of particular importance is ensuring that the administered agents affect only targeted cells (e.g., cancer cells), tissues, or organs. The nonspecific or unintended delivery of highly cytotoxic agents to non-targeted cells can cause serious toxicity issues.

Numerous attempts have been made to devise drug-targeting schemes to address the problems associated with nonspecific drug delivery. (See e.g., K. N. Syrigos and A. A. Epenetos Anticancer Res., 19:606-614 (1999); Y. J. Park et al., J. Controlled Release, 78:67-79 (2002); R. V. J. Chari, Adv. Drug Deliv. Rev., 31:89-104 (1998); and D. Putnam and J. Kopecek, Adv. Polymer Sci., 122:55-123 (1995)). Conjugating targeting moieties such as antibodies and ligand peptides (e.g., RDG for endothelium cells) to drug molecules has been used to alleviate some collateral toxicity issues associated with particular drugs.

The compounds and anticancer agents may be administered in any sterile, biocompatible pharmaceutical carrier, including, but not limited to, saline, buffered saline, dextrose, and water. In some embodiments, the pharmaceutical compositions of the present invention may contain one agent (e.g., an antibody). In other embodiments, the pharmaceutical compositions contain a mixture of at least two agents (e.g., an antibody and one or more conventional anticancer agents). In still further embodiments, the pharmaceutical compositions of the present invention contain at least two agents that are administered to a patient under one or more of the following conditions: at different periodicities, at different durations, at different concentrations, by different administration routes, etc. In some embodiments, the IL8-CXCR1 signaling pathway antagonist is administered prior to the second anticancer agent, e.g., 0.5, 1, 2 3, 4, 5, 10, 12, or 18 hours, 1, 2, 3, 4, 5, or 6 days, 1, 2, 3, or 4 weeks prior to the administration of the anticancer agent. In some embodiments, the IL8-CXCR1 signaling pathway antagonist is administered after the second anticancer agent, e.g., 0.5, 1, 2 3, 4, 5, 10, 12, or 18 hours, 1, 2, 3, 4, 5, or 6 days, 1, 2, 3, or 4 weeks after the administration of the anticancer agent. In some embodiments, the IL8-CXCR1 signaling pathway antagonist and the second anticancer agent are administered concurrently but on different schedules, e.g., the IL8-CXCR1 signaling pathway antagonist compound is administered daily while the second anticancer agent is administered once a week, once every two weeks, once every three weeks, or once every four weeks. In other embodiments, the IL8-CXCR1 signaling pathway antagonist is administered once a week while the second anticancer agent is administered daily, once a week, once every two weeks, once every three weeks, or once every four weeks.

Depending on the condition being treated, preferred embodiments of the present pharmaceutical compositions are formulated and administered systemically or locally. Techniques for formulation and administration can be found in the latest edition of "Remington's Pharmaceutical Sciences" (Mack Publishing Co, Easton Pa.). Suitable routes may, for example, include oral or transmucosal administration as well as parenteral delivery (e.g., intramuscular, subcutaneous, intramedullary, intrathecal, intraventricular, intravenous, intraperitoneal, or intranasal administration).

The present invention contemplates administering therapeutic compounds and, in some embodiments, one or more conventional anticancer agents, in accordance with acceptable pharmaceutical delivery methods and preparation techniques. For example, therapeutic compounds and suitable anticancer agents can be administered to a subject intravenously in a pharmaceutically acceptable carrier such as physiological saline. Standard methods for intracellular delivery of pharmaceutical agents are contemplated (e.g., delivery via liposome). Such methods are well known to those of ordinary skill in the art.

In some embodiments, the formulations of the present invention are useful for parenteral administration (e.g., intravenous, subcutaneous, intramuscular, intramedullary, and intraperitoneal). Therapeutic co-administration of some contemplated anticancer agents (e.g., therapeutic polypeptides) can also be accomplished using gene therapy reagents and techniques.

In some embodiments of the present invention, therapeutic compounds are administered to a subject alone, or in combination with one or more conventional anticancer agents (e.g., nucleotide sequences, drugs, hormones, etc.) or in pharmaceutical compositions where the components are optionally mixed with excipient(s) or other pharmaceutically acceptable carriers. In preferred embodiments of the present invention, pharmaceutically acceptable carriers are biologically inert. In preferred embodiments, the pharmaceutical compositions of the present invention are formulated using pharmaceutically acceptable carriers well known in the art in dosages suitable for oral administration. Such carriers enable the pharmaceutical compositions to be formulated as tablets, pills, capsules, dragees, liquids, gels, syrups, slurries, solutions, suspensions and the like, for respective oral or nasal ingestion by a subject.

Pharmaceutical preparations for oral use can be obtained by combining the active compounds with solid excipients, optionally grinding the resulting mixture, and processing the mixture into granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

In preferred embodiments, dosing and administration regimes are tailored by the clinician, or others skilled in the pharmacological arts, based upon well known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy (e.g., destruction of cancer cells) is desired, doses in excess of the average required dose are not uncommon. This approach to dosing is commonly referred to as the "maximal dose" strategy. In certain embodiments, the IL8-CXCR1 signaling pathway antagonist is administered to a subject at a dose of 1-40 mg per day (e.g. for 4-6 weeks). In certain embodiments, subject is administered a loading dose of between 15-70 mg of the IL8-CXCR1 signaling pathway antagonist. In certain embodiments, the subject is administered a loading dose of about 35-45 mg of the IL8-CXCR1 signaling pathway antagonist (e.g. subcutaneously), and then daily doses of about 10 mg (e.g. subcutaneously) for about 4-6 weeks.

Additional dosing considerations relate to calculating proper target levels for the agent being administered, the agent's accumulation and potential toxicity, stimulation of resistance, lack of efficacy, and describing the range of the agent's therapeutic index.

In certain embodiments, the present invention contemplates using routine methods of titrating the agent's administration. One common strategy for the administration is to set a reasonable target level for the agent in the subject. In some preferred embodiments, agent levels are measured in the subject's plasma. Proper dose levels and frequencies are then designed to achieve the desired steady-state target level for the agent. Actual, or average, levels of the agent in the subject are monitored (e.g., hourly, daily, weekly, etc.) such that the dosing levels or frequencies can be adjusted to maintain target levels. Of course, the pharmacokinetics and pharmacodynamics (e.g., bioavailability, clearance or bioaccumulation, biodistribution, drug interactions, etc.) of the particular agent or agents being administered can potentially impact what are considered reasonable target levels and thus impact dosing levels or frequencies.

Target-level dosing methods typically rely upon establishing a reasonable therapeutic objective defined in terms of a desirable range (or therapeutic range) for the agent in the subject. In general, the lower limit of the therapeutic range is roughly equal to the concentration of the agent that provides about 50% of the maximum possible therapeutic effect. The upper limit of the therapeutic range is usually established by the agent's toxicity and not by its efficacy. The present invention contemplates that the upper limit of the therapeutic range for a particular agent will be the concentration at which less than 5 or 10% of subjects exhibit toxic side effects. In some embodiments, the upper limit of the therapeutic range is about two times, or less, than the lower limit. Those skilled in the art will understand that these dosing consideration are highly variable and to some extent individualistic (e.g., based on genetic predispositions, immunological considerations, tolerances, resistances, and the like). Thus, in some embodiments, effective target dosing levels for an agent in a particular subject may be 1, . . . 5, . . . 10, . . . 15, . . . 20, . . . 50, . . . 75, . . . 100, . . . 200, . . . X %, greater than optimal in another subject. Conversely, some subjects may suffer significant side effects and toxicity related health issues at dosing levels or frequencies far less (1, . . . 5, . . . 10, . . . 15, . . . 20, . . . 50, . . . 75, . . . 100, . . . 200, . . . X %) than those typically producing optimal therapeutic levels in some or a majority of subjects. In the absence of more specific information, target administration levels are often set in the middle of the therapeutic range.

In preferred embodiments, the clinician rationally designs an individualized dosing regimen based on known pharmacological principles and equations. In general, the clinician designs an individualized dosing regimen based on knowledge of various pharmacological and pharmacokinetic properties of the agent, including, but not limited to, F (fractional bioavailability of the dose), Cp (concentration in the plasma), CL (clearance/clearance rate), Vss (volume of drug distribution at steady state) Css (concentration at steady state), and t½ (drug half-life), as well as information about the agent's rate of absorption and distribution. Those skilled in the art are referred to any number of well known pharmacological texts (e.g., Goodman and Gilman's, Pharmaceutical Basis of Therapeutics, 10th ed., Hardman et al., eds., 2001) for further explanation of these variables and for complete equations illustrating the calculation of individualized dosing regimes. Those skilled in the art also will be able to anticipate potential fluctuations in these variables in individual subjects. For example, the standard deviation in the values observed for F, CL, and Vss is typically about 20%, 50%, and 30%, respectively. The practical effect of potentially widely varying parameters in individual subjects is that 95% of the time the Css achieved in a subject is between 35 and 270% that of the target level. For drugs with low therapeutic indices, this is an undesirably wide range. Those skilled in the art will appreciate, however, that once the agent's Cp (concentration in the plasma) is measured, it is possible to estimate the values of F, CL, and Vss directly. This allows the clinician to effectively fine tune a particular subject's dosing regimen.

In still other embodiments, the present invention contemplates that continuing therapeutic drug monitoring techniques be used to further adjust an individual's dosing methods and regimens. For example, in one embodiment, Css data is used is to further refine the estimates of CL/F and to subsequently adjust the individual's maintenance dosing to achieve desired agent target levels using known pharmacological principles and equations. Therapeutic drug monitoring can be conducted at practically any time during the dosing schedule. In preferred embodiments, monitoring is carried out at multiple time points during dosing and especially when administering intermittent doses. For example, drug monitoring can be conducted concomitantly, within fractions of a second, seconds, minutes, hours, days, weeks, months, etc., of administration of the agent regardless of the dosing methodology employed (e.g., intermittent dosing, loading doses, maintenance dosing, random dosing, or any other dosing method). However, those skilled in the art will appreciate that when sampling rapidly follows agent administration the changes in agent effects and dynamics may not be readily observable because changes in plasma concentration of the agent may be delayed (e.g., due to a slow rate of distribution or other pharmacodynamic factors). Accordingly, subject samples obtained shortly after agent administration may have limited or decreased value.

The primary goal of collecting biological samples from the subject during the predicted steady-state target level of administration is to modify the individual's dosing regimen based upon subsequently calculating revised estimates of the agent's CL/F ratio. However, those skilled in the art will appreciate that early postabsorptive drug concentrations do not typically reflect agent clearance. Early postabsorptive drug concentrations are dictated principally by the agent's rate of absorption, the central, rather than the steady state, volume of agent distribution, and the rate of distribution. Each of these pharmacokinetic characteristics have limited value when calculating therapeutic long-term maintenance dosing regimens.

Accordingly, in some embodiments, when the objective is therapeutic long-term maintenance dosing, biological samples are obtained from the subject, cells, or tissues of interest well after the previous dose has been administered, and even more preferably shortly before the next planned dose is administered.

In still other embodiments, where the therapeutic agent is nearly completely cleared by the subject in the interval between doses, then the present invention contemplates collecting biological samples from the subject at various time points following the previous administration, and most preferably shortly after the dose was administered.

VII. Repertaxin and Other Small Molecule CXCR1 Inhibitors

In certain embodiments, the methods, kits, and compositions of the present invention employ small molecule inhibitors of CXCR1. One exemplary agent is repartaxin. In certain embodiments, the in vivo dose of repartaxin is between 3 and 60 mg per kilogram (e.g., 3 . . . 30 . . . 50 . . . 60 mg/kg). In particular embodiments, the dose of repartaxin is about 30 mg per kilogram. The chemical formula for repartaxin is shown below:

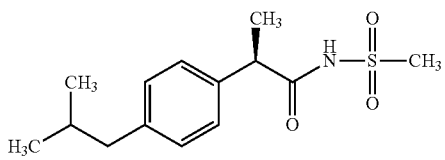 [SMILES: CC(C)Cc1ccc([C@@H](C)C(=O)NS(C)(=O)=O)cc1]

In other embodiments, derivatives of the repertaxin are employed. Other small molecule CXCR1 antagonists include SB265610 (Glaxo SmithKline Beecham; Benson et al., 2000, 151:196-197), as well as SCH 527123 (2-hydroxy-N,N-dimethyl-3-{2-[[(R)-1-(5-methylfuran-2-yl)propyl]amino]-3,4-dioxocyclobut-1-enylamino} benzamide (SCH 527123), an orally bioavailable CXCR2/CXCR1 receptor antagonist (Schering Plough)). Other small molecule inhibitors can be identified by the screening methods described above.

EXAMPLES

The following example is provided in order to demonstrate and further illustrate certain preferred embodiments and aspects of the present invention and is not to be construed as limiting the scope thereof.

Example 1

CXCR1 Identifies Cancer Stem Cells

This example describes the identification of CXCR1, as well as other proteins (e.g., FBXO21), as cancer stem cell markers.

Cell Culture.

Breast cell lines (BCL) were obtained from the ATCC ("http://www." followed by "lgcpromochem-atcc.com/common/catalog/cellBiology/cellBiologyIndex.cfm") or from collections developed in the laboratories of Drs. S. Ethier (now available on "http://www." followed by "asterand.com/asterand/BIOREPOSITORY/hbreastcancercelllines.aspx, SUM44, SUM52, SUM149, SUM159, SUM185, SUM190, SUM225, SUM229"), V. J. Maus (BrCa-MZ-01), and V. Catros (S68). All BCLs tested were derived from carcinomas except MCF10A, which is derived from fibrocystic disease, and the HMEC-derived 184A1, which was derived from normal mammary tissue. The cell lines were grown using the recommended culture conditions. All experiments were done with subconfluent cells in the exponential phase of growth.

ALDEFLUOR Assay and Separation of the ALDH-Positive Population by FACS.

ALDH activity was assessed in 33 BCLs representing the main molecular subtypes of human breast cancer. The ALDEFLUOR kit (StemCell technologies, Durham, N.C., USA) was used to isolate the population with high ALDH enzymatic activity (17). Cells obtained from subconfluent cell lines after trypsinization or from freshly dissociated xenografts were suspended in ALDEFLUOR assay buffer containing ALDH substrate (BAAA, 1 µmol/l per $1\times10^6$ cells) and incubated for 40 minutes at 37° C. In each experiment a sample of cells was stained under identical conditions with 50 mmol/L of diethylaminobenzaldehyde (DEAB), a specific ALDH inhibitor, as negative control. Flow cytometry sorting was conducted using a FACStar-PLUS (Becton Dickinson). ALDEFLUOR Fluorescence was Excited at 488 nm and Detected Using Standard Fluorescein Isothiocyanate (FITC) 530/30 Band Pass Filter. For xenotransplanted tumors, incubation with an anti-H2Kd antibody (BD biosciences, 1/200, 20 min on ice) followed by a secondary antibody labeled with phycoerythrin (Jackson labs, 1/250, 20 min on ice) was used to eliminate cells of mouse origin. The sorting gates were established using PI stained cells for viability, ALDEFLUOR-stained cells treated with DEAB, and those stained with secondary antibody alone. Prior to RNA profiling or NOD/SCID mice injection, the purity of sorted populations was checked using double sorting of 10,000 ALDEFLUOR-positive and negative cells in BrCa-MZ-01 and SUM159 cell lines. For both cell lines, sorted ALDEFLUOR-positive populations contained more than 98% of ALDEFLUOR-positive cells and no ALDEFLUOR-positive cells were detected in the ALDEFLUOR-negative population.

Tumorigenicity in NOD/SCID Mice.

Tumorigenicity of ALDEFLUOR-positive, -negative and unseparated SUM159, MDA-MB-453 and BrCa-MZ-01 cells was assessed in NOD/SCID mice. Fat pads were cleared of epithelium at 3 weeks of age prior to puberty and humanized by injecting human fibroblasts (1:1 irradiated: non-irradiated, 50,000 cells/1000 Matrigel/fat pad) as described (17). The animals were euthanized when the tumors were 1.2 cm in the largest diameter, in compliance with regulations for use of vertebrate animal in research. A portion of each fat pad was fixed in formalin and embedded in paraffin for histological analysis. Another portion was assessed by the ALDEFLUOR assay, followed by sorting and serial transplantation.

Anchorage-Independent Culture.

ALDEFLUOR-positive, -negative and unseparated cells from 184A1, SUM149 and SUM159 were plated as single cells in ultra-low attachment plates (Corning, Acton, Mass.) at low density (5000 viable cells/ml). Cells were grown in serum-free mammary epithelial basal medium (Cambrex Bio Science, Walkerville, Md.) for 3-7 days, as described (18). The capacity of cells to form spheres was quantified after treatment with different doses of IL8 (GenWay Biotech, San Diego, Calif.) added to the medium.

RNA Extraction.

Total RNA was extracted from frozen ALDEFLUOR-positive and -negative cells using DNA/RNA All Prep Maxi Kit, according to the manufacturer's instructions (Qiagen, Sample and Assay technologies, The Netherlands). Eight BCLs were used for transcriptional analysis: 184A1, BrCa-MZ-01, HCC1954, MDA-MB-231, MDA-MB-453, SK-BR-7, SUM149, and SUM159. RNA integrity was controlled by denaturing formaldehyde agarose gel electrophoresis and micro-analysis (Agilent Bioanalyzer, Palo Alto, Calif.).

Gene Expression Profiling with DNA Microarrays.

Gene expression analyses used Affymetrix U133 Plus 2.0 human oligonucleotide microarrays containing over 47,000 transcripts and variants including 38,500 well-characterized human genes. Preparation of cRNA, hybridizations, washes and detection were done as recommended by the supplier ("http://www." followed by "affymetrix.com/index.affx"). Expression data were analyzed by the RMA (Robust Multichip Average) method in R using Bioconductor and associated packages (19), as described (20, 21). RMA did background adjustment, quantile normalization and summarization of 11 oligonucleotides per gene.

Before analysis, a filtering process removed from the dataset genes with low and poorly measured expression as defined by expression value inferior to 100 units in all the 16 samples, retaining 25,285 genes/ESTs. A second filter, based on the intensity of standard deviation (SD), was applied for unsupervised analyses to exclude genes showing low expression variation across the analyses. SD was calculated on log 2-transformed data, in which lowest values were first floored to a minimal value of 100 units, i.e. the background intensity, retaining 13,550 genes/ESTs with SD superior to 0.5. An unsupervised analysis was done on 16 ALDEFLUOR-positive, -negative cells on 13,550 genes. Before hierarchical clustering, filtered data were log 2-transformed and submitted to the Cluster program (22) using data median-centered on genes, Pearson correlation as similarity metric and centroid linkage clustering. Results were displayed using TreeView program (22). To identify and rank genes discriminating ALDEFLUOR-positive and -negative populations, a Mann and Whitney U test was applied to the 25,285 genes/ESTs and false discovery rate (FDR, (23) was used to correct the multiple testing hypothesis. The classification power of the discriminator signature was illustrated by classifying samples by hierarchical clustering. A LOOCV was applied to estimate the accuracy of prediction of the identified molecular signatures and the validity of supervised analysis; each sample was excluded one by one and classified with the linear discriminant analysis (LDA, (24) by using model defined on the non-excluded samples.

Real-Time RT-PCR.

After ALDEFLUOR-positive and ALDEFLUOR-negative populations from different cell lines were sorted, total RNA was isolated using RNeasy Mini Kit (QIAGEN) and utilized for real-time quantitative RT-PCR (qRT-PCR) assays in a ABI PRISM® 7900HT sequence detection system with 384-well block module and automation accessory (Applied Biosystems). Primers and probes for the Taqman system were selected from the Applied Biosystems website. The sequences of the PCR primer pairs and fluorogenic probes used for CXCR1, FBXO21, NFYA, NOTCH2, RAD51L1 and TBP are available on the Applied Biosystems website (CXCR1 assay ID: Hs_00174146_mi; FBXO21 assay ID: Hs_00372141_mi, NFYA assay ID: Hs_00953589_mi, NOTCH2 assay ID: Hs_01050719_mi, RAD51L1 assay ID: Hs_00172522_mi, TBP assay ID: Hs_00427620_mi). The relative expression mRNA level of CXCR1, FBXO21, NFYA, NOTCH2, RAD51L1 was computed with respect to the internal standard TBP gene to normalize for variations in the quality of RNA and the amount of input cDNA, as described previously (25).

Invasion Assay.

Assays were done in triplicate in transwell chambers with 8 μm pore polycarbonate filter inserts for 12-well plates (Corning, N.Y.). Filters were coated with 30 ul of ice-cold 1:6 basement membrane extract (Matrigel, BD-Bioscience) in DMEM/F12 incubated 1 hour at 37° C. Cells were added to the upper chamber in 200 ul of serum-free medium. For the invasion assay, 5000 cells were seeded on the Matrigel-coated filters and the lower chamber was filled with 600 ul of medium supplemented with 10% human serum (Cambrex) or with 600 ul of serum-free medium supplemented with IL8 (100 ng/mL). After 48 hours incubation, the cells on the underside of the filter were counted using light microscopy. Relative invasion was normalized to the unseparated corresponding cell lines under serum condition.

Lentivirus Infection.

For luciferase gene transduction, 70% confluent cells from HCC1954, MDA-MB-453, and SUM159 were incubated overnight with a 1:3 precipitated mixture of lentiviral supernatants Lenti-LUC-VSVG (Vector Core, Ann Arbor, Mich.) in culture medium. The following day the cells were harvested by trypsin/EDTA and subcultured at a ratio of 1:6. After 1 week incubation, cells were sorted according to the ALDEFLUOR phenotype and luciferase expression was verified in each sorted population (ALDEFLUOR-positive and ALDEFLUOR-negative) by adding 2 ml D-luciferin 0.0003% (Promega, Madison, Wis.) in the culture medium and counting photon flux by device camera system (Xenogen, Alameda, Calif.).

Intracardiac Inoculation.

Six weeks-old NOD/SCID mice were anesthetized with 2% isofluorane/air mixture and injected in the heart left ventricle with 100,000 cells in 100 μL of sterile Dulbecco's PBS lacking Ca2+ and Mg2+. For each of the three cell lines (HCC1954, MDA-MB-453, SUM159) and for each population (ALDEFLUOR-positive, ALDEFLUOR-negative and unsorted), three animals were injected.

Bioluminescence Detection.

Baseline bioluminescence was assessed before inoculation and each week thereafter inoculations. Mice were anesthetized with a 2% isofluorane/air mixture and given a single i.p. dose of 150 mg/kg D-luciferin (Promega, Madison, Wis.) in PBS. Animals were then re-anesthetized 6 minutes after administration of D-luciferin. For photon flux counting, a charge-coupled device camera system (Xenogen, Alameda, Calif.) was used with a nose-cone isofluorane delivery system and heated stage for maintaining body temperature. Results were analyzed after 2 to 12 minutes of exposure using Living Image software provided with the Xenogen imaging system. Signal intensity was quantified as the sum of all detected photon flux counts within a uniform region of interest manually placed during data postprocessing. Normalized photon flux represents the ratio of the photon flux detected each week after inoculations and the photon flux detected before inoculation.

Statistical Analysis.

Results are presented as the mean±SD for at least three repeated individual experiments for each group. Statistical analyses used the SPSS software (version 10.0.5). Correlations between sample groups and molecular parameters were calculated with the Fisher's exact test or the one-way ANOVA for independent samples. A p-value *0.05 was considered significant.

The Majority of Breast Cell Lines Contain an ALDEFLUOR-Positive Population.

The ALDEFLUOR assay (17) was used to isolate CSC from 33 BCLs representing the diverse molecular subtypes and features of breast cancer (20). It was found that 23 out of the 33 cell lines contained an ALDEFLUOR-positive cell population that ranged from 0.2 to nearly 100%. All 16 basal/mesenchymal BCLs contained an ALDEFLUOR-positive population whereas 7 out of the 12 luminal BCLs did not contain any detectable ALDEFLUOR-positive cells (p=0.0006, Fischer's exact test).

ALDEFLUOR-Positive Cells have Tumorsphere-Forming Capacity.

It has previously been reported that mammary epithelial stem and progenitor cells are able to survive and proliferate in anchorage-independent conditions and form floating spherical colonies which are termed mammospheres (18). Data from breast tumors, as well as cell lines, have demonstrated that cancer stem-like cells or cancer-initiating cells can also be isolated and propagated as "tumorspheres" in similar assays (26). All mammosphere-initiating cells in the normal human mammary gland are contained within the ALDEFLUOR-positive population (17). To characterize the ALDEFLUOR-positive population from BCLs, the ability of ALDEFLUOR-positive and -negative populations from 184A1, SUM149 and SUM159 to form tumorspheres were compared. In each cell line, the ALDEFLUOR-positive population showed increased tumorsphere-forming capacity compared to ALDEFLUOR-negative cells.

ALDEFLUOR-Positive BCL Cells have Cancer Stem Cell Properties In Vivo.

Figure 1:
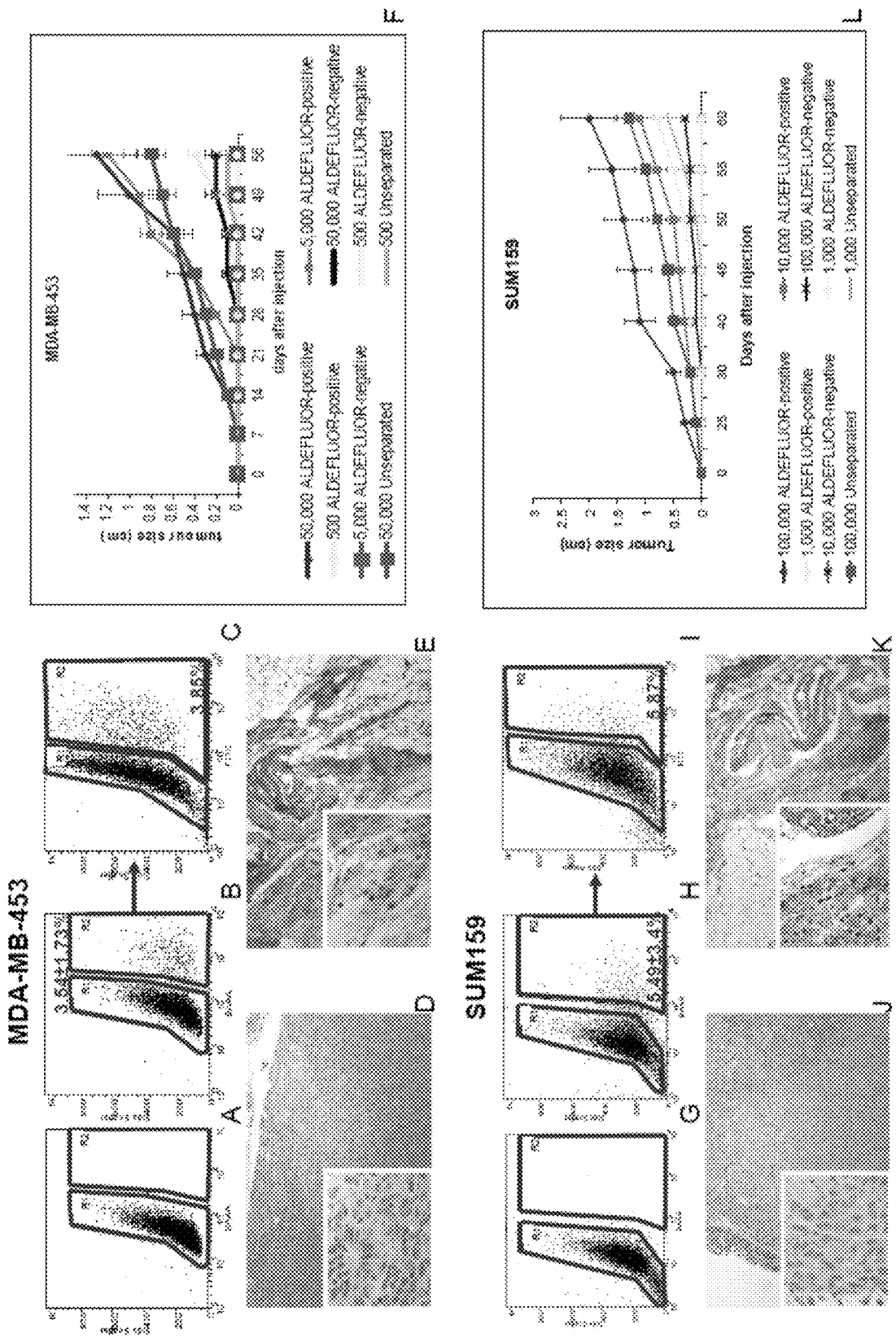
FIG. 1 shows the ALDEFLUOR-positive cell populations from breast cancer cell lines (MDA-MB-453, SUM159)

To determine the hierarchical organization of BCL, the stem cell properties of the ALDEFLUOR-positive and -negative populations of MDA-MB-453, SUM159, and BrCa-MZ-01 cell lines were analyzed. The ALDEFLUOR-positive populations of these three BCLs constituted between 3.54±1.73% and 5.49±3.36% of the total cell populations (FIG. 1A-B, G-H; FIG. 2A-B). As shown in FIG. 1F, L the size and latency of tumor formation correlated with the number of ALDEFLUOR-positive cells injected. Remarkably, 500 ALDEFLUOR-positive cells from MDA-MB-453 and 1,000 ALDEFLUOR-positive cells from SUM159 were able to form tumors. The tumor-generating capacity was maintained through serial passages demonstrating the self-renewal capacity of these cells. In contrast, ALDEFLUOR-negative cells failed to generate tumors, although limited growth was produced when 50,000 ALDEFLUOR-negative MDA-MB-453 cells were injected. H&E staining of the fat pad sections confirmed that tumors formed by ALDEFLUOR-positive cells contained malignant cells whereas only residual Matrigel, apoptotic cells and mouse tissue were seen at the sites of ALDEFLUOR-negative cell injections (FIG. 1E, K). Consistent with the ALDEFLUOR-positive population having cancer stem cell characteristics, tumors generated by this population recapitulated the phenotypic heterogeneity of the initial tumor, with a similar ratio of ALDEFLUOR-positive and -negative cells (FIG. 1C, I). This indicates that ALDEFLUOR-positive cells were able to self-renew, generating ALDEFLUOR-positive cells and were able to differentiate, generating ALDEFLUOR-negative cells.

When BrCa-MZ-01 cells were separated into ALDEFLUOR-positive and -negative components, both were capable of tumor generation. Tumors generated by the ALDEFLUOR-positive population consisted of both ALDEFLUOR-positive and -negative cells recapitulating the phenotypic heterogeneity of the initial tumor. In contrast, tumors generated by ALDEFLUOR-negative cells gave rise to slowly growing tumors containing only ALDEFLUOR-negative cells. In contrast to the ability of ALDEFLUOR-positive cells to be serially transplanted, serial passages of ALDEFLUOR-negative tumors produced decreasing tumor growth with no growth following three passages. This suggests that the ALDEFLUOR-positive component of the BrCa-MZ-01 cells contain cells with stem cell properties, whereas the ALDEFLUOR-negative cells contain progenitor cells able to undergo limited growth but not self-renewal.

Gene Expression Profiling of ALDEFLUOR-Positive and -Negative Cell Populations.

To determine whether ALDEFLUOR-positive cells isolated from different BCLs expressed a common set of "cancer stem cell" genes, the ALDEFLUOR-positive and -negative cell populations isolated from eight BCLs (184A1, BrCa-MZ-01, HCC1954, MDA-MB-231, MDA-MB-453, SK-BR-7, SUM49, and SUM159) were analyzed using Affymetrix whole-genome oligonucleotide microarrays. Unsupervised hierarchical clustering, applied to the 16 samples and the 13,550 filtered genes/ESTs, did not separate ALDEFLUOR-positive and -negative populations. Instead, ALDEFLUOR-positive and -negative populations clustered with the parental cell line. This suggests that the differences in mRNA transcripts between clonal cell lines supersede differences between ALDEFLUOR-positive and ALDEFLUOR-negative cells. This further suggests that only a limited number of genes are differentially expressed between putative cancer stem cells and their progeny.

To determine which genes discriminated ALDEFLUOR-positive and -negative populations, the Mann and Whitney U test was applied to all genes but those with low and poorly measured expression, i.e. 25,285 probe sets. This test identified and ranked after FDR correction, 413 genes/ESTs that discriminated the ALDEFLUOR-positive and -negative cell populations. The 28 overexpressed genes corresponding to unique genes are shown in Table 1, and the most frequently underexpressed genes are shown in Table 2.

TABLE 1

Up Regulated Genes

| Category | Symbol | Description | Cytoband | Probe set ID | Function |
| --- | --- | --- | --- | --- | --- |
| Genes previously described to have a role in stem cell biology | TPRXL | tetra-peptide repeat homeobox-like | chr3p25.1 | 239061_at | early embryonic development |
|  | NOTCH2 | Notch homolog 2 (*Drosophila*) | chr1p13-p11 | 202443_x_at | Self-renewal program |
|  | RBM15 | RNA binding motif protein 15 | chr1p13 | 1555760_a_at | determination of hematopoietic cell fate |
|  | ST3GAL3 | ST3 beta-galactoside alpha-2,3-sialyltransferase 3 | chr1p34.1 | 1555181_a_at | maintenance of the embryonic antigens SSEA-3 and -4 |
|  | NFYA | nuclear transcription factor Y, alpha | chr6p21.3 | 204107_at | Self-renewal program |
|  | PCNX | pecanex homolog (*Drosophila*) | chr14q24.2 | 213173_at | determination of neural cell fate of early developing embryo |
| Signaling | FBXO21 * | F-box protein 21 | chr12q24.22 | 212231_at | Ubiquitination |
|  | WWOX | WW domain containing oxidoreductase | chr16q23.3-q24.1 | 210695_s_at | Protein degradation, transcription, and RNA splicing |
|  | CAMK2B | Calcium/calmodulin-dependent protein kinase (CaM kinase) II beta | chr22q12 | 34846_at | Calcium signaling |
|  | PNPLA2 | patatin-like phospholipase domain containing 2 | chr11p15.5 | 39854_r_at | Triglyceride hydrolysis |
|  | CLIC5 | chloride intracellular channel 5 | chr6p12.1-21.1 | 213317_at | chloride ion transport |
|  | UGCGL1 | UDP-glucose ceramide glucosyltransferase-like 1 | chr2q14.3 | 222569_at | Protein glucosylation |
|  | FBXL18 | F-box and leucine-rich repeat protein 18 | chr7p22.2 | 220896_at | Ubiquitination |
|  | ADRBK1 | adrenergic, beta, receptor kinase 1 | chr11q13 | 38447_at | Phosphorylation of G-protein-coupled receptors |
|  | SLC38A2 | Solute carrier family 38, member 2 | chr12q | 1559924_at | neutral amino acid transporter |
| Membrane protein | IL8RA* (CXCR1) | interleukin 8 receptor, alpha | chr2q35 | 207094_at | Inflamatory response |
|  | TAS2R14 | Taste receptor, type 2, member 14 | chr12p13 | 241997_at | Bitter perception |
|  | CD300LB | CD300 molecule-like family member b | chr17q25.1 | 1554173_at | Immune response |
|  | GIPC3 | GIPC PDZ domain containing family, member 3 | chr19p13.3 | 236730_at |  |
| DNA repair | RAD51L1 | RAD51-like 1 (*S. cerevisiae*) | chr14q23-q24.2 | 1570166_a_at | homologous recombination repair |
| Chromatin remodeling | ARID1B | AT rich interactive domain 1B (SWI1-like) | chr6q25.1 | 225181_at | Chromatin remodeling (SWI/SNF complexe) |
| Cytoskeleton | EPPK1 | epiplakin 1 | chr8q24.3 | 208156_x_at | Maintenance of the keratin intermediate filaments |
| Extracellular matrix | COL11A2 | collagen, type XI, alpha 2 | chr6p21.3 | 216993_s_at | skeletal morphogenesis |
|  | KLK3 | Kallikrein 3, (prostate specific antigen) | chr19q13.41 | 231629_x_at | Protease |
| RNA interference | EIF2C2 | Eukaryotic translation initiation factor 2C, 2 | chr8q24 | 213310_at | short-interfering-RNA-mediated gene silencing |
| Unknown | ZFP41 | zinc finger protein 41 homolog (mouse) | chr8q24.3 | 227898_s_at | Unknown |
|  | FAM49B | Family with sequence similarity 49, member B | chr8q24.21 | 243182_at | Unknown |
|  | PSORS1C2 | psoriasis susceptibility 1 candidate 2 | chr6p21.3 | 220635_at | Unknown |

TABLE 2

Down Regulated Genes

| Category | Symbol | Description | Cytoband | Probe set ID | Function |
|---|---|---|---|---|---|
| Protein synthesis | MRPL42* | mitochondrial ribosomal protein L42 | chr12q22 | 217919_s_at | Protein synthesis within the mitochondrion |
| | MRPL54* | mitochondrial ribosomal protein L54 | chr19p13.3 | 225797_at | Protein synthesis within the mitochondrion |
| | MRPL47* | mitochondrial ribosomal protein L47 | chr3q26.33 | 223480_s_at | Protein synthesis within the mitochondrion |
| | MRPS23* | mitochondrial ribosomal protein S23 | chr17q22-q23 | 223156_at | Protein synthesis within the mitochondrion |
| | EIF3S9* | eukaryotic translation initiation factor 3, subunit 9 eta, 116 kDa | chr7p22.2 | 236274_at | Initiation of protein synthesis (EIF3 multiprotein complex) |
| Signaling | ALG5* | asparagine-linked glycosylation 5 homolog | chr13q13.3 | 218203_at | Protein glucosylation |
| | DNAJC19* | DnaJ (Hsp40) homolog, subfamily C, member 19 | chr3q26.33 | 225359_at | Importation of mithochondrial protein |
| | HBLD2* | HESB like domain containing 2 | chr9q21.33 | 221425_s_at | iron-sulfur cluster biogenesis |
| | GART* | Phosphoribosylglycinamide formyltransferase, phosphoribosylglycinamide synthetase, phosphoribosylaminoimidazole synthetase | chr21q22.1 | 230097_at | de novo purine biosynthesis |
| | NUP37* | nucleoporin 37 kDa | chr12q23.2 | 218622_at | Intrcellular protein transport across nuclear membrane |
| | RNF7* | ring finger protein 7 | chr3q22-q24 | 224439_x_at | subunit of SKP1-cullin/CDC53-F box protein ubiquitin ligases |
| | DC2* | DC2 protein | chr4q25 | 223001_at | protein glycosylation |
| | USP15* | ubiquitin specific peptidase 15 | chr12q14 | 210681_s_at | Protein degradation |
| | COMMD6* | COMM domain containing 6 | — | 225312_at | Inhibition NF-KappaB Signaling |
| | UBL5* | Ubiquitin-like 5 | chr19p13.3 | 218011_at | Ubiquitination |
| Apoptosis | MRPL41* | mitochondrial ribosomal protein L41 | chr9q34.3 | 225425_s_at | Stabilization of p53 protein, Cell cycle arrest (p21(WAF1/CIP1) and p27(Kip1) dependent) |
| | PDCD10* | programmed cell death 10 | chr3q26.1 | 210907_s_at | Initiation of apoptosis |
| | PDCD5* | Programmed cell death 5 | chr19q12- | 227751_at | Initiation of apoptosis |
| Differentiation program | NACA* | nascent-polypeptide-associated complex alpha polypeptide | chr12q23-q24.1 | 222018_at | Erythroid differentiation |
| Cell cycle | FAM82B* | family with sequence similarity 82, member B | chr8q21.3 | 218549_s_at | Regulation of microtubule dynamic |
| RNA splicing | CCNL1* | cyclin L1 | chr3q25.32 | 1555411_a_at | Pre-mRNA processing |
| | PRPF39* | PRP39 pre-mRNA processing factor 39 homolog (S. cerevisiae) | chr14q21.3 | 220553_s_at | Pre-mRNA processing |
| | LSM3* | LSM3 homolog, U6 small nuclear RNA associated (S. cerevisiae) | chr3p25.1 | 202209_at | Pre-mRNA processing |
| | SFRS7* | splicing factor, arginine/serine-rich 7, 35 kDa | chr2p22.1 | 213649_at | Regulation of RNA splicing |
| | PRPF4B* | PRP4 pre-mRNA processing factor 4 homolog B (yeast) | chr6p25.2 | 202127_at | Pre-mRNA processing |
| Oxidative phosphorylation | ATP5S* | ATP synthase, H+ transporting, mitochondrial F0 complex, subunit s (factor B) | chr14q22.1 | 206992_s_at | subunit of mitochondrial ATP synthase |

TABLE 2-continued

Down Regulated Genes

| Category | Symbol | Description | Cytoband | Probe set ID | Function |
|---|---|---|---|---|---|
| | NDUFA2* | NADH dehydrogenase (ubiquinone) 1 alpha subcomplex, 2, | chr5q31 | 209224_s_at | components of the complex I multi-subunit enzyme |
| | ATP5J2* | ATP synthase, H+ transporting, mitochondrial F0 complex, subunit F2 | chr7q22.1 | 202961_s_at | subunit of mitochondrial ATP synthase |
| | IMMP1L* | IMP1 inner mitochondrial membrane peptidase-like | chr11p13 | 230556_at | Proteolysis |
| Unknown | ASTE1* | asteroid homolog 1 (Drosophila) | chr3q22.1 | 221135_s_at | Unknown |
| | MGC61571* | hypothetical protein MGC61571 | chr3p24.1 | 228283_at | Unknown |
| | WDR53* | WD repeat domain 53 | chr3q29 | 227814_at | Unknown |
| | DKFZP686A10121* | hypothetical protein | chr7q21.13 | 234311_s_at | Unknown |
| | CHCHD8* | coiled-coil-helix-coiled-coil-helix domain containing 8 | chr11q13.4 | 220647_s_at | Unknown |
| | FLJ32745* | hypothetical protein FLJ32745 | chr2q13 | 235644_at | Unknown |
| | CHURC1* | churchill domain containing 1 | chr14q23.3 | 233268_s_at | Unknown |
| | XTP3TPA* | XTP3-transactivated protein A | chr16p11.2 | 218069_at | Unknown |
| | FLJ37953* | hypothetical protein FLJ37953 | chr2q33.1 | 235181_at | Unknown |
| | SNORD50A* | small nucleolar RNA, C/D box 50A | chr6q14.3 | 244669_at | Unknown |
| | LOC644053* | hypothetical protein LOC644053 | chr1q41 | 235466_s_at | Unknown |
| | TMEM141* | transmembrane protein 141 | chr9q34.3 | 225568_at | Unknown |
| | C8orf59* | chromosome 8 open reading frame 59 | chr8q21.2 | 226165_at | Unknown |

The classification power of this discriminating signature was illustrated by classifying the 16 ALDEFLUOR-positive and -negative samples with the 413 differentially expressed genes/ESTs. Hierarchical clustering ranked 15 out of the 16 samples (FIG. 2A).

A number of genes known to play a role in stem cell biology were upregulated in the ALDEFLUOR-positive populations (Table 1), including NFYA, NOTCH2, PCNX, RBM15, ST3GAL3, and TPRXL. Other genes encode proteins that have putative or uncharacterized role in stem cell function, such as ARID1B, RAD51L1, and the chemokine receptor CXCR1/IL8RA (27). Genes underexpressed in the ALDEFLUOR-positive population are involved in cell differentiation, apoptosis, RNA splicing, and mitochondrial metabolism.

To increase the stringency of analysis, the threshold of the Mann and Whitney analysis was raised to the 0.5 risk and obtained a list of 49 genes/ESTs that discriminated ALDEFLUOR-positive and -negative populations (genes with asterisk in Tables 1-2). With this list, all of the ALDEFLUOR-positive cells, except from SK-BR-7, clustered together. Among these 49 genes/ESTS, 45 corresponded to identified unique genes; only 3 of these 45 were overexpressed in the ALDEFLUOR-positive group while 42 were underexpressed. Characterized overexpressed genes code for an F-box protein FBXO21 and CXCR1/IL8RA. Underexpressed genes include those coding for mitochondrial proteins (MRPL41, MRPL42, MRPL47, MRPL54, MRPS23, IMMP1L), and differentiation (NACA) and pre-mRNA splicing factors (LSM3, pre-mRNA processing factor PRPF39 and PRPF4B). Leave-one-out cross-validation (LOOCV) at 0.5% risk estimated the accuracy of prediction of the identifier molecular signature and 88% of the samples were predicted in the right class with this "cancer stem cell signature" confirming the supervised analysis.

Quantitative RT-PCR assessment confirmed a significant increase of CXCR1 and FBXO21 in ALDEFLUOR-positive cells. Quantitative RT-PCR analysis of five discriminator genes overexpressed in ALDEFLUOR-positive populations (CXCR1/IL8RA, FBXO21, NFYA, NOTCH2 and RAD51L1) was performed. Three cell lines used in the profiling analysis (BrCa-MZ-01, MDA-MB-453, SUM159) and two additional luminal cell lines (MCF7, S68) were sorted by ALDEFLUOR-assay and ALDEFLUOR-positive and -negative populations were processed separately for quantitative RT-PCR analysis. The quantitative RT-PCR expression level of CXCR1 and FBXO21 are presented in FIGS. 2 B and C. Gene expression levels measured by quantitative RT-PCR confirmed the results obtained using DNA microarrays with an increase of CXCR1 and FBXO21 mRNA level in the ALDEFLUOR-positive population compared to the ALDEFLUOR-negative population (p<0.05).

IL8 Promotes Cancer Stem Cell Self-Renewal.

The profiling studies suggested that the IL8 receptor CXCR1/IL8RA was consistently expressed in the ALDEFLUOR-positive cell population. To confirm this association, the protein expression of CXCR1/IL8RA was measured by flow cytometry in ALDEFLUOR-positive and -negative populations. The ALDEFLUOR-positive and -negative populations from four different cell lines were isolated by FACS, fixed, and stained with a CXCR1 monoclonal antibody labeled with phycoerythrin. As shown in FIG. 3A, ALDEFLUOR-positive cells were highly enriched in CXCR1-positive cells compared to the ALDEFLUOR-negative populations.

To determine whether IL8 signaling is important in stem cell function, four BCLs were treated with human recombinant IL8 to determine its effect on the cancer stem cell population as measured by the formation of tumorspheres and by ALDH enzymatic activity. As shown in FIG. 3B, addition of IL8 increased the formation of primary and secondary tumorspheres in a dose-dependent manner. Furthermore, IL8 increased the ALDEFLUOR-positive population in a dose-dependent manner in each of the four BCLs analyzed (FIG. 3C). This illustrates the power of the "CSC signature" to identify pathways that may play a role in stem cell function.

The IL8/CXCR1 Axis is Involved in Cancer Stem Cell Invasion.

The IL8/CXCR1 axis has been reported to play a role in cancer stem cell invasion (28, 29). A Matrigel invasion assay was utilized, using serum as attractant, to examine the ability of ALDEFLUOR-positive and -negative cell populations from three different cell lines (HCC1954, MDA-MB-453, SUM159) to invade. As shown in FIG. 4A, ALDEFLUOR-positive cells demonstrated 6- to 20-fold higher invasion through Matrigel than the ALDEFLUOR-negative population (p<0.01). When used as a chemo-attractant IL8 (100 ng/ml) increased invasion of the ALDEFLUOR-positive cells (p<0.05) (FIG. 4A). In contrast to its effects on ALDEFLUOR-positive cells, IL8 did not have any effect on the invasive capacity of ALDEFLUOR-negative cells. These results indicate that cancer stem cells exhibited invasive behavior and furthermore that IL8 facilitates this process.

ALDEFLUOR-Positive Cells have Increased Metastatic Potential.

It has been proposed that CSCs play a crucial role in cancer metastasis (30, 31). The above experiments demonstrated that ALDEFLUOR-positive cells have increased invasive capacity compared to ALDEFLUOR-negative cells. To determine the relationship between ALDEFLUOR-positivity and metastatic capacity, HCC1954, MDA-MB-453, and SUM159 were infected with a luciferase lentivirus reporter system. Luciferase-infected cells were sorted using the ALDEFLUOR assay and introduced into NOD/SCID mice by intracardiac injection. A suspension of 100,000 cells from each population was injected and metastasis was assessed by bioluminescent imaging. Mice inoculated with ALDEFLUOR-positive cells developed metastases at different sites and displayed a higher photon flux emission than mice inoculated with unseparated cells, which developed no more than one metastasis per mouse, or mice inoculated with ALDEFLUOR-negative cells, which developed only occasional metastases limited to lymph nodes (FIG. 4B-J). Histologic sections confirmed the presence of metastases at these sites (FIG. 4K-M). Thus, the metastatic capacity of BCLs is predominantly mediated by CSCs contained in the ALDEFLUOR-positive population.

The hypothesis that tumors are organized in a cellular hierarchy driven by CSCs has fundamental implications for cancer biology as well as clinical implications for the early detection, prevention and treatment of cancer. Evidence for CSCs has largely relied on primary and early passage xenograft models (32-34). However, the success of establishing breast tumor xenograft has been low particularly for certain molecular subtypes. In contrast to primary tumors, cell lines are available in unlimited quantities and provide only carcinomatous populations for molecular analysis without normal tissue and stroma. In breast cancer, a large number of immortalized cell lines have been produced which represent the different molecular subtypes found in primary human breast cancers (2, 20). However, a fundamental question remains as to how closely these cell lines are able to recapitulate the biology of human breast cancer.

In Vivo Evidence for Stem Cells in Cell Lines.

Recent studies have suggested that although cell lines may be clonally derived, they contain a cellular hierarchy representing different stages of cellular differentiation. Several studies have utilized markers such as CD44+/CD24− to identify CSC within breast cancer cell lines. However, their utility is limited by the observation that frequently a large percentage of cells within a cell line express these putative stem cell markers. For example, greater than 90% of cells in basal breast cancer cell lines display the CD44+/CD24− phenotype. Indeed, the CD44+/CD24-phenotype did not isolate the tumorigenic population of these cell lines (Ginestier et al. Cell Stem Cell 1:555-567., herein incorporated by reference in its entirety). An alternative approach has been to use the SP from cell lines. However, functional studies utilizing Hoechst staining are limited by the toxicity of this agent (35). There is also evidence that the functional stem cell activity is not contained within the SP(36).

ALDH activity assessed by the ALDEFLUOR assay isolates cells with stem cell properties from various cancers (14, 37). In this Example it was demonstrated that 23 out of 33 BCLs (predominantly basal cell lines) contain an ALDEFLUOR-positive population. Lack of an ALDEFLUOR-positive population in some luminal BCLs may indicate that these luminal BCLs are derived from ALDEFLUOR-negative progenitor cells.

This Example utilized in vivo assays in NOD/SCID mice to demonstrate the stem cell properties of the ALDEFLUOR-positive populations. Self-renewal was demonstrated by serial passage in NOD/SCID mice and differentiation was demonstrated by the ability of ALDEFLUOR-positive but not ALDEFLUOR-negative cells to regenerate the cellular heterogeneity of the initial tumor.

A Breast Cancer Stem Cell Signature.

Utilizing eight breast cell lines, this Example identified 413 genes whose expression discriminates ALDEFLUOR-positive and -negative cells. This signature contained a number of genes known to play a role in stem cell biology. Genes overexpressed in the ALDEFLUOR-positive population include Notch homolog 2 (NOTCH2), which regulates self-renewal and differentiation of mammary stem cells (18, 38), NFYA, known to regulate self-renewal and differentiation of stem cells. (39, 40), pecanex homolog PCNX, RBM15/OTT, which plays a pleiotropic role in hematopoietic stem cells (41) and affects myeloid differentiation via NOTCH signaling (42), homeobox-like factor TPRXL involved in embryonic development, ST3GAL3, which codes for a stage-specific embryonic antigen-4 synthase, associated with fetal development and renal and gastric carcinogenesis (43). Notably, stage-specific embryonic antigen-4 protein (SSEA-4) is expressed in stem cell populations such as CXCR4+/CD133+/CD34+/lin− stem cells in human cord blood and quiescent mammary stem cells (44).

Genes underexpressed in the ALDEFLUOR-positive population are involved in cell differentiation, apoptosis, and mitochondrial oxidation. They include genes coding for nascent polypeptide-associated complex alpha subunit NACA, programmed death proteins PDCD5 and PDCD10, mitochondrial ribosomal protein L41 (MRPL41), which induces apoptosis through P53-dependent and independent manner via BCL2 and caspases, and proteins involved in mitochondrial processes such as oxidative phosphorylation (NDUFA2, ATP5J2, IMMP1L) and protein synthesis in the mitochondrion (MRPL42, MRPL47, MRPL54, MRPS23). Downregulation of apoptotic genes in CSCs may play a role in the resistance of these cells to radiation and chemotherapy (45, 46). ALDH1A1 was not identified as a differentially-expressed gene in the ALDEFLUOR-positive signature. However, examination of gene expression profile of individual BCLs revealed that although some showed differential expression of ALDH1A1 in the ALDEFLUOR-positive population, others showed differential expression of ALDH1A3, a different ALDH isoform in this population. This suggests that the expression of different ALDH isoforms could contribute to the ALDEFLUOR-positive phenotype.

From Chemokines to "Stemokines."

The expression of CXCR1, a receptor for IL8, is increased in a variety of cancers (47-50). Although IL8 expression is associated with ER-negative breast cancer (51), this chemokine has not previously been reported to play a role in stem cell function. Its implication in the regulation of growth and metastasis is well-established in androgen-independent prostate cancer (52). Furthermore, the expression level of IL8 is associated with tumorigenicity and metastasis through VEGF production and angiogenesis (53, 54). The gene expression data was validated in three ways. First, quantitative RT-PCR analysis confirmed a significant increase of CXCR1 mRNA in ALDEFLUOR-positive population from cell lines both included and not included in profiling analysis. Second, it was demonstrated using flow cytometry that CXCR1-containing cells were found exclusively within the ALDEFLUOR-positive population. Third, recombinant IL8 increased mammosphere formation and the percent of ALDEFLUOR-positive cells in BCLs. The IL8/CXCR1 axis thus appears to regulate mammary stem cell proliferation or self-renewal. Since endothelial and stromal cells secrete IL8 this chemokine appears to play a role in mediating interactions between tumor stem cells and the tumor microenvironment.

Recent studies have suggested a role for interleukines/chemokines in the regulation of CSCs (55, 56). This includes a role for IL6 in breast CSCs and IL4 in mediating chemoresistance of colon CSCs (56-59). These factors may be involved in the association between inflammation and cancer. This also includes a role for CCL5 (RANTES), a chemokine secreted by mesenchymal stem cells, which acts as a paracrine factor and enhance breast cancer cells motility, invasion and metastasis(55).

The Roots of Metastasis.

CSCs may be responsible for mediating tumor metastasis. A link between CSC and metastasis was first suggested with the identification of stem cell genes in an 11-gene signature generated using comparative profile of metastastatic and primary tumors in transgenic mouse model of prostate cancer and cancer patients (60). This signature was also a powerful predictor of disease recurrence, death after therapy and distant metastasis in a variety of cancer types. This Example has demonstrated that ALDEFLUOR-positive cells are more metastatic than ALDEFLUOR-negative cells and that IL8, previously reported to play a role in tumor metastasis, promotes the invasion and chemotaxis of cancer stem cells which preferentially express the IL8 receptor CXCR1. The ability to isolate metastatic cancer stem cell from cell lines should facilitate studies of the molecular mechanisms by which cancer stem cells mediate tumor metastasis.

Example 2

CXCR1 Inhibition and Combination Therapy

This example describes various methods employed to test the effect of CXCR1 inhibition on tumor cells, as well as the combination of CXCR1 inhibition in combination with an anti-mitotic agent (docetaxel).
Effect of CXCR1 Inhibition on the Cell Growth and on the ALDEFLUOR Positive Population of SUM159 Cell Line.

The SUM159 cell line was cultured in adherent condition and treated the cells using the CXCR1/CXCR2 inhibitor Repertaxin or two specific blocking antibodies for CXCR1 or CXCR2. After 4 days of treatment, the effect on cell growth was analyzed using the MTT assay (FIG. 5A) and on the cancer stem cell population using the ALDEFLUOR assay (FIG. 5B). More than 95% of cell growth inhibition was observed in the cells treated with Repertaxin or the CXCR1 blocking antibody, whereas no effect was observed for the cells treated with the CXCR2 blocking antibody (FIG. 5A). Interestingly similar effect was observed on the ALDEFLUOR-positive population with a decrease of 80% and 50% of the ALDEFLUOR-positive population in the cells treated with Repertaxin and CXCR1 blocking antibody respectively (FIG. 5B).
Repertaxin Treatment Induces a Bystander Effect Mediated by the FAS/FAS Ligand Signaling SUM159 cell line cells were cultured in adherent conditions and then treated with Repertaxin alone or in combination with a FAS antagonist. Interestingly, the cell growth inhibition induced by the Repertaxin treatment was partially rescued by the addition of a FAS antagonist (anti/Fas-ligand from BD pharmingen (cat#556371)). Moreover, the cells treated with a FAS agonist displayed a similar cell growth inhibition than the cells treated with Repertaxin. These results suggest that Repertaxin treatment induces a bystander effect mediated by the FAS/FAS ligand signaling.
Effect of Repertaxin Treatment on FAK, AKT and FOXOA3 Activation.

In order to evaluate the effect of Repertaxin treatment on the CXCR1 downstream signaling, SUM159 cells were cultured, during 2 days, in adherent condition in the absence or in presence of 100 nM of Repertaxin and stained by immunofluorescence with antibodies against p-FAK, p-AKT, and FOXOA3. In the non-treated cells (FIG. 7A), it was detected that 30% of cells expressing p-FAK and 10% of cells expressing p-AKT displayed inactivation, while cells treated with Repertaxin displayed a complete inactivation of p-FAK and p-AKT (FIG. 7B). The non-treated SUM159 cells presented 80% of cells positive in the cytoplasm for FOXOA3. Interestingly, SUM159 cells treated with Repertaxin presented 80% of cells positive in the nucleus for FOXOA3. The change in FOXOA3 cellular location from the cytoplasm to the nucleus indicates an activation of FOXOA3 protein.
Tumors Growth Curves Following the Treatment with Repertaxin, Docetaxel or the Combination The effect of Repertaxin, docetaxel, or the combination thereof was evaluated using one breast cancer cell lines (8A, SUM159) and three human breast cancer xenografts generated from different patients (8B, MC1; 8C, UM2; and 8D, UM3). For each sample, 50,000 cells were injected into the mammary fat pad of NOD-SCID mice which were monitored for tumor size. Injections were started when the tumor size was about 4 mm. Repertaxin was injected (15 mg/Kg) twice a day for 28 days or once a week, docetaxel was I.P. injected (10 mg/Kg), or the combination (Repertaxin/Docetaxel) was employed. FIG. 8 shows the tumor sizes before and during the course of each indicated treatment (arrow, beginning of the treatment). Similar results are observed for each sample (SUM159, MC1, UM2, UM3) with a statistically significant reduction of the tumor size when treated with Docetaxel alone or the combination Repertaxin/Docetaxel compared to the control ($p<0.01$) whereas no significant difference are observed between the growth of the control tumors and the tumors treated with Reperataxin.
Effect of Repertaxin, Docetaxel, or the Combination Treatment on the Cancer Stem Cell Population as Assessed by the ALDEFLUOR Assay ALDH activity was assessed by the ALDEFLUOR assay for analyzing the cancer stem cell populations size in each tumor (9A. SUM159, 9B. MC1, 9C. UM2, 9D. UM3) treated with Repertaxin, docetaxel or the combination. Similar results are observed for each sample. Docetaxel treated tumor xenografts showed similar or increase percentage of ALDEFLUOR-positive cells compare to the control, whereas Repertaxin treatment alone or in combination with docetaxel produced a statistically significant decrease in ALDEFLUOR-positive cells with 65% to 85% less cancer stem cells compare to the control (p<0.01).

Effect of Repertaxin, Docetaxel, or the Combination Treatment on the Cancer Stem Cell Population as Assessed by Implantation in Secondary Mice.

Serial dilutions of cells obtained from primary tumors (10A. SUM159, 10B. MC1, 10C. UM2, 10D. UM3) non treated (control) and treated with Repertaxin, docetaxel or the combination were implanted in the mammary fat pad of secondary NOD-SCID mice. Control and docetaxel treated primary tumors formed secondary tumors at all dilutions whereas, only higher concentration of primary tumors treated with Repertaxin or in combination with docetaxel were able form delayed secondary tumors which were significantly smaller in size than the control or docetaxel treated tumors (p<0.01). Moreover, 1000 and 100 primary treated cells with the combination failed to form secondary tumors for 3 out of 4 samples (SUM159, UM2, UM3).

Repertaxin Treatment Reduces the Metastatic Potential of SUM159 Cell Line

A SUM159 cell line was infected with a lentivirus expressing luciferase and inoculated 250,000 luciferase infected cells in the heart of NOD/SCID mice. The mice were organized into two groups. The two groups of mice were treated 12 hours after the intracardiac injection either with s.c. injection of saline solution or s.c. injection of Repertaxin (15 mg/kg), twice a day during 28 days. Metastasis formation was monitored using bioluminescence imaging (11B: Mice treated with saline solution; 11C: Mice treated with Repertaxin). Quantification of the normalized photon flux measured at weekly intervals following inoculation revealed a statistically significant increase of metastasis formation in the group of mice treated with saline solution compare to the group of mice treated with Repertaxin (11A).

Example 3

Treatment of Cancer Stem Cells by CXCR1 Blockade

This example demonstrates the effect of CXCR1 inhibition on tumor cells, through both in vitro assays and mouse models.

Dissociation of Mammary Tissue.

100-200 g of normal breast tissue from reduction mammoplasties was minced with scalpels, dissociated enzymatically, and single cells were cultured in suspension to generate mammospheres or on a collagen substratum in adherent condition to induce cellular differentiation (Dontu et al. Genes Dev. 17:1253-1270, herein incorporated by reference in its entirety).

Cell Culture.

Breast cancer cell lines were grown using recommended culture conditions (Charafe-Jauffret et al. Cancer Res. 69:1302-1313., herein incorporated by reference in its entirety). Breast cancer cell lines were treated in adherent condition with repertaxin (Sigma-Aldrich), anti-human CXCR1 mouse monoclonal antibody (Clone 42705, R&D systems), anti-human CXCR2 mouse monoclonal antibody (clone 48311, R&D systems), anti-human CD95 mouse monoclonal antibody (Clone DX2, BD Pharmingen) utilized as a FAS signaling agonist, anti-human FAS-Ligand mouse monoclonal antibody (Clone NOK-1, BD pharmingen) utilized as a FAS signaling antagonist, or with docetaxel (Taxotere, Sanofi-Aventis).

Cell Viability.

For MTT assays, cells were plated in adherent condition in 96-well plates at 5,000 cells per well. After one day, treatment with repertaxin was started. The effect of repertaxin treatment on cell viability was estimated at different time points by addition of 20 µl of MTT solution (5 mg/mL in PBS) in each well. Cells were then incubated for 1 hour at 37° C. followed by addition of 50 µL of DMSO to each well. Absorbance was measured at 560 nm in a fluorescence plate reader (Spectrafluor, Tecan). For TUNEL assays, cells were plated in adherent conditions in 6-well plates at 50,000 cells per well. After one day, treatment with repertaxin was started. The number of apoptotic cells was estimated after four days treatment. Cells were fixed in 3.7% formaldehyde and stained utilizing the TACS TdT kit (R&D systems). Nuclei were counterstained with DAPI/antifade (Invitrogen). Sections were examined with a fluorescent microscope (Leica, Bannockborn, Ill., USA) with apoptotic cells detected in green.

ALDEFLUOR Assay.

The ALDEFLUOR kit (StemCell technologies) was used to isolate the population with high ALDH enzymatic activity using a FACStarPLUS (Becton Dickinson) as previously described (Ginestier et al. Cell Stem Cell 1:555-567., herein incorporated by reference in its entirety). In order to eliminate cells of mouse origin from the xenotransplanted tumors, cell population was stained with an anti-H2Kd antibody (BD biosciences, 1/200, 20 min on ice) followed by staining with a secondary antibody labeled with phycoerythrin (PE) (Jackson labs, 1/250, 20 min on ice).

ELISA Assay.

To measure the level of soluble FAS-ligand secreted in the culture medium of cells treated or not with repertaxin, Human sFAS Ligand Elisa (Bender Medsystems) was utilized. Absorbance was read on a spectro-photometer using 450 nm as the primary wave length.

Western Blotting.

Cells were lysed in a laemmli buffer and loaded onto SDS-polyacrylamide gels. Blots were incubated with the respective primary antibodies diluted in TBST (containing 0.1% Tween20 and 2% BSA) either overnight at 4°, or 2 hours at room temperature. Blots were washed and incubated with appropriate secondary antibodies (GE Healthcare, UK) and detected using SuperSignal West Pico Chemiluminescent Substrate (Pierce).

Immunostaining.

For immunofluorescent staining, sorted CXCR1-positive cells were fixed with 95% methanol at −20° C. for 10 minutes. Cells were rehydrated in PBS and incubated with respective antibodies at room temperature for 1 hour. Primary antibodies used were P-FAK (1:50, Cell Signaling Technology), P-AKT (1:300, Cell Signaling Technology), and FOXO3a (1:250, Cell Signaling Technology). Slides were then washed and incubated 30 minutes with PE conjugated secondary antibodies (Jackson labs). The nuclei were counterstained with DAPI/antifade (Invitrogen) and coverslipped. Sections were examined with a fluorescent microscope (Leica, Bannockborn, Ill., USA). Immunohistochemistry for the detection of ALDH1 (1:100, BD biosciences), P-FAK, P-AKT, FOXO3a expression was done on paraffin section (Ginestier et al. Am. J Pathol. 161:1223-1233., herein incorporated by reference in its entirety). Staining was done utilizing the Histostainplus kit (Zymed laboratories). Diaminobenzidine (DAB) or 3-amino-9-ethylcarbazole (AEC) was used as chromogen and sections were counterstained with hematoxylin.

Animal Model.

Tumorigenicity of ALDEFLUOR-positive/CXCR1-positive and ALDEFLUOR-positive/CXCR1-negative SUM159 cells was assessed in NOD/SCID mice (Ginestier et al. Cell Stem Cell 1:555-567., herein incorporated by reference in its entirety)., The SUM159 cell line and three primary human breast cancer xenografts generated from three different patients (MC1, UM2, UM3) were utilized to determine the efficiency of repertaxin treatment on tumor growth (Ginestier et al. Cell Stem Cell 1:555-567., herein incorporated by reference in its entirety). Cells from these tumors were transplanted orthotopically in the humanized cleared fat-pad of NOD/SCID mice, without cultivation in vitro. Fat pads were prepared as described previously (Ginestier et al. Cell Stem Cell 1:555-567., herein incorporated by reference in its entirety). 50,000 cells from each xenotransplants were injected in the humanized fat pad of NOD/SCID mice and monitored the tumor growth. When the tumor size was approximately 4 mm, treatment with repertaxin alone (s.c., 15 mg/Kg, twice a day, during 28 days), docetaxel alone (i.p., 10 mg/Kg, once a week, during 4 weeks), in combination (repertaxin/docetaxel), or a control group injected with saline (i.p., once a week and s.c. twice a day, during 28 days) was initiated. The animals were euthanized when the tumors were approximately 1.5 cm in the largest diameter, to avoid tumor necrosis and in compliance with regulations for use of vertebrate animal in research. A portion of each fat pad injected was fixed in formalin and embedded in paraffin for histological analysis. The rest of the tumor cells were re-implanted into secondary NOD/SCID mice. Serial dilutions of cells were utilized for the re-implantation with injection of 10,000, 1,000, and 100 cells for each treated tumor.

Anchorage-Independent Culture.

BCLs treated, in adherent conditions, with repertaxin (100 nM), anti-CXCR1 antibody (10 µg/ml), or anti-CXCR2 (10 µg/ml) were dissociated and plated as single cells in ultra-low attachment plates (Corning, Acton, Mass.) at low density (5,000 viable cells/ml). Cells were grown as previously described (Charafe-Jauffret et al. Cancer Res. 69:1302-1313., herein incorporated by reference in its entirety). Subsequent cultures after dissociation of primary tumorospheres were plated on ultra-low attachment plates at a density of 5,000 viable cells/ml. The capacity of cells to form tumorspheres was quantified after the first (primary tumorospheres) and second (secondary tumorospheres) passage.

RNA Extraction and qRT-PCR.

After SUM159 cells were treated, total RNA was isolated using RNeasy Mini Kit (QIAGEN) and utilized for real-time quantitative RT-PCR (qRT-PCR) assays in a ABI PRISM® 7900HT sequence detection system. Primers and probes for the Taqman system were selected from the Applied Biosystems website (www dot applied biosystems dot com) (FAS-Ligand assay ID: Hs_00899442_mi; IL8 assay ID: Hs_00174103_mi, TBP assay ID: Hs_00427620_mi). The relative expression mRNA level of FAS-Ligand and IL8 was computed with respect to the internal standard TBP gene to normalize for variations in the quality of RNA and the amount of input cDNA, as described previously (Ginestier et al. Clin. Cancer Res. 12:4533-4544., herein incorporated by reference in its entirety).

Flow Cytometry Analysis.

CD44/CD24/Lin staining was performed (Ginestier et al. Cell Stem Cell 1:555-567., herein incorporated by reference in its entirety). CD95/FAS staining were performed utilizing an anti-CD95 labeled APC (1:20, BD biosciences). For CXCR1 and CXCR2 staining, primary antibodies anti-CXCR1 (1:100, Clone 42705, R&D systems) and anti-CXCR2 (1:100, clone 48311, R&D systems) were followed by a staining with a secondary antibody anti-mouse labeled with PE (dilution 1:250, Jackson Labs). Fresh cells were stained With 1 µg/ml PI (Sigma) for 5 min for viability.

Virus Infection.

Two different lentiviral constructs were produced for the expression of Luciferase gene (Lenti-LUC-VSVG) (Charafe-Jauffret et al. Cancer Res. 69:1302-1313., herein incorporated by reference in its entirety) and for the inhibition PTEN expression (Lenti-PTEN-SiRNA-DsRed) (Korkaya et al. PLoS Biolog. 7:e1000121., herein incorporated by reference in its entirety), respectively. All lentiviral constructs were prepared by the University of Michigan Vector. An adenoviral construct for the overexpression of FAK (Ad-FAK-GFP) was also utilized (Luo et al. Cancer Res. 69:466-474., herein incorporated by reference in its entirety). Cells infection with different vectors was performed as previously described (Charafe-Jauffret et al. Cancer Res. 69:1302-1313., herein incorporated by reference in its entirety). Efficiency of infection was verified by measuring the percentage of DsRed or GFP expressing cells.

Intracardiac Inoculation.

Six weeks-old NOD/SCID mice were anesthetized with 2% isofluorane/air mixture and injected in the heart left ventricle with 250,000 cells in 100 µL of sterile Dulbecco's PBS lacking $Ca^{2+}$ and $Mg^{2+}$. For each of the three cell lines (HCC1954, MDA-MB-453, and SUM159) and for each treatment (saline or repertaxin) six animals were injected. Twelve hours after intracardiac injections, mice were begun on twice per day repertaxin injections or saline for the controls.

Bioluminescence Detection.

Baseline bioluminescence was assessed before inoculation and each week thereafter inoculations. Bioluminescence detection procedures was performed as previously described (Charafe-Jauffret et al. Cancer Res. 69:1302-1313., herein incorporated by reference in its entirety). Normalized photon flux represents the ratio of the photon flux detected each week after inoculations and the photon flux detected before inoculation.

CXCR1 Expression Subdivides Cancer Stem Cell Populations.

Identifying cell signaling pathways that regulate cancer stem cells (CSC) provides potential therapeutic targets in a cell population. A breast CSC signature based on gene expression profiling that contained several genes potentially involved in breast CSC regulatory pathways has been identified (Charafe-Jauffret et al. Cancer Res. 69:1302-1313., herein incorporated by reference in its entirety). Among the genes overexpressed in the breast CSC population, CXCR1 a receptor that binds the proinflammatory chemokine IL-8/CXCL8 appeared to be a promising candidate since recombinant IL-8 stimulated the self-renewal of breast C (Charafe-Jauffret et al. Cancer Res. 69:1302-1313., herein incorporated by reference in its entirety). Utilizing flow cytometry, CXCR1 protein expression was measured in the breast CSC population as assessed by the ALDEFLUOR assay in the human breast cancer cell lines HCC1954, MDA-MB-453, and SUM159. Cells with functional stem cell properties in NOD/SCID mouse xenographs were contained within the ALDEFLUOR-positive cell population (Charafe-Jauffret et al. Cancer Res. 69:1302-1313., herein incorporated by reference in its entirety). The CXCR1-positive population, which represents less than 2% of the total population, was almost exclusively contained within the ALDEFLUOR-positive population (SEE FIG. 12A and Table 4).

TABLE 4

|  | ALDEFLUOR (%) | CXCR1 (%) | Overlap CXCR1/ ALDEFLUOR (%) |
|---|---|---|---|
| Breast cancer cell lines | | | |
| HCC1954 | 3.42 | 1.72 | 0.94 |
| MDA-MB-453 | 4.22 | 0.8 | 0.5 |
| SUM159 | 5.24 | 0.52 | 0.48 |
| Human breast cancer xenografts | | | |
| MC1 | 12.3 | 1.81 | 1.32 |
| UM2 | 8.4 | 1.23 | 0.88 |
| UM3 | 9.7 | 0.84 | 0.76 |

CXCR2 expression was also assessed. CXCR2 is a receptor that can also bind IL-8/CXL8 although with reduced affinity compared to CXCR1. In contrast to CXCR1-positive cells, CXCR2-positive cells were equally distributed between the ALDEFLUOR-positive and ALDEFLUOR-negative populations (SEE FIG. 12A). To determine the hierarchical organization of the cancer stem cell population according to CXCR1 expression, ALDEFLUOR-positive/CXCR1-positive and ALDEFLUOR-positive/CXCR1-negative cell populations were sorted and injected in NOD/SCID mice (SEE FIG. 13). Both cell populations generated tumors. Tumor growth kinetics correlated with the latency and size of tumor formation and the number of cells injected. Tumors generated by the ALDEFLUOR-positive/CXCR1-positive population reconstituted the phenotypic heterogeneity of the initial tumor upon serial passages whereas the ALDEFLUOR-positive/CXCR1-negative population gave rise to tumors containing only ALDEFLUOR-positive/CXCR1-negative cells. These results suggest that CSC cellular hierarchy is organized according to CXCR1 expression, however both cell populations displayed similar tumorigenic capacity.

CXCR1 Blockade Decreases the Breast Cancer Stem Cell Population In Vitro.

Three different cell lines were treated with repertaxin (100 nM), a CXCR1/2 inhibitor, to evaluate the effect of CXCR1 blockade on the breast CSC population (Bertini et al. Proc. Natl. Acad. Sci. USA 101:11791-11796., herein incorporated by reference in its entirety). For SUM159, after three days of treatment a five-fold reduction in the proportion of ALDEFLUOR-positive cells was observed (SEE FIG. 12B). A similar effect was observed after treatment of SUM159 cells with an anti-CXCR1 blocking antibody. In contrast, no effect was observed after treatment with an anti-CXCR2 blocking antibody, suggesting that the effects of repertaxin on the ALDEFLUOR-positive population were mediated by CXCR1.

Data from breast tumors, as well as cell lines, demonstrate that cancer stem-like cells or cancer-initiating cells can also be isolated and propagated as "tumorspheres" in suspension culture (Ponti et al. Cancer Res. 65:5506-5511., herein incorporated by reference in its entirety). After three days of treatment with repertaxin or with the anti-CXCR1 blocking antibody, when cells were detached and cultured in suspension, an 8-fold decrease in primary and secondary tumorsphere formation was observed compared to controls. In contrast, anti-CXCR2 blocking antibody had no effect on tumorsphere formation (SEE FIG. 14).

Surprisingly, after five days of treatment with repertaxin we observed a massive decrease in viability of the entire cell population as assessed by MTT assay, with only 3% of cells remaining viable (SEE FIG. 12C). Similar results were observed with the anti-CXCR1 blocking antibody but not the anti-CXCR2 blocking antibody, thus indicating that this effect was dependent on CXCR1 blockade. This effect of repertaxin was delayed with loss of cell viability beginning three days after treatment (SEE FIG. 15A). Repertaxin treatment induced a similar effect on the HCC1954 breast cancer cell line whereas no effect was observed on MDA-MB-453 cells which harbor a PTEN mutation (Hollestelle et al. Cancer Res. 5:195-201., herein incorporated by reference in its entirety) (SEE FIGS. 14, 15B-C, and 16).

Utilizing a TUNEL assay, SUM159 cells were stained after 4 days of treatment with repertaxin and a massive decrease in cell viability, due to induction of apoptosis with 36% apoptotic cells detected after repertaxin treatment, was observed (SEE FIG. 12D). Results suggest that CXCR1 blockade results in a decrease of the breast CSC population followed by induction of massive apoptosis in the remaining bulk tumor population.

CXCR1 Blockade Induces Cell Death in CXCR1-Negative Cells Via a Bystander Effect.

The observation that repertaxin or anti-CXCR1 blocking antibody induced massive cell death despite the fact that the CXCR1-positive population represented less than 2% of the total cell population suggested that CXCR1 blockade in CXCR1-positive cells induced CXCR1-negative cell death via a bystander effect. The sorted CXCR1-positive and CXCR1-negative populations were treated with repertaxin (SEE FIG. 12E). Repertaxin decreased cell viability in the CXCR1-positive population within three days whereas no effect was observed in the CXCR1-negative population. Repertaxin induced massive cell death in unseparated cells. The effect of repertaxin on cell viability of the unseparated and CXCR1-positive populations was dose-dependent (SEE FIG. 12E). The results are consistent with repertaxin treatment targeting the CXCR1-positive population that in turn induces CXCR1-negative cell death via a bystander effect.

To determine whether this effect was mediated by a soluble factor induced by repertaxin, conditioned medium was collected from the CXCR1-positive population after three days of repertaxin treatment and dialyzed this medium utilizing a membrane with 3.5 KDa exclusion in order to remove repertaxin from the medium while retaining molecules larger than 3.5 KDa. The dialyzed conditioned medium induced a massive decrease in cell viability in both CXCR1-negative and unseparated populations but not in the CXCR1-positive population (SEE FIG. 12F). These results demonstrate that CXCR1 blockade in the CXCR1-positive population induces cell death in the CXCR1-negative population via a soluble non dialyzable factor. Although the CXCR1-positive population is sensitive to repertaxin it is resistant to the dialyzable death factor.

The Bystander Effect Induced by CXCR1 Blockade is Mediated by FAS-Ligand/FAS Signaling.

FAS-ligand/FAS interaction is activated in different physiologic states such as mammary gland involution or in conditions of tissue injury including that induced by chemotherapy (Chhipa et al. J Cell Biochem. 101:68-79., Song et al. J Clin. Invest 106:1209-1220, herein incorporated by reference in their entireties). The level of soluble FAS-ligand in the medium of SUM159 cells treated with repertaxin using an ELISA Assay to evaluate the role of FAS-ligand/

FAS interaction in mediating the apoptotic bystander effect induced by CXCR1 blockade. More than a five-fold increase of soluble FAS-ligand in the medium of cells treated for four days with repertaxin compared to non-treated cells was observed (SEE FIG. 17A). The transcriptional regulation of FAS-ligand by repertaxin treatment by measuring FAS-ligand mRNA level was confirmed by RT-PCR (SEE FIG. 17B). A 4-fold increase of the FAS-ligand mRNA level in the repertaxin treated cells was observed compared to non-treated cells. Similar results were observed after treatment with a FAS agonist that activates FAS signaling, indicating that FAS-ligand is a target of FAS signaling generating a positive feed-back loop. 100% of the SUM159 cells expressed FAS protein as determined by flow cytometry. Treatment of the SUM159 cells with the FAS agonist reproduced the killing effect observed with the repertaxin treatment with massive reduction in cell viability (SEE FIG. 17C). The effect of repertaxin treatment on cell viability was partially reversed by an anti-FAS-Ligand blocking antibody, with 44% of cells remaining viable after treatment with repertaxin and anti-FAS-ligand antibody compared to only 3% with repertaxin alone (SEE FIG. 17C). Results suggest that the massive cell death induced by repertaxin is due to a bystander effect mediated by the FAS-Ligand/FAS pathway.

Treatment of SUM159 cells with the FAS agonist resulted in a ten-fold and three-fold increase in the percent of CXCR1-positive and ALDEFLUOR-positive cells, respectively (SEE FIG. 17D/E and 18). The effects of repertaxin on both populations were not rescued by anti-FAS-ligand (SEE FIG. 17D/E), suggesting that the ALDEFLUOR-positive population that contains the CXCR1-positive population, while directly sensitive to CXCR1 blockade which in turn induces FAS-ligand production by these cells is resistant to FAS-ligand/FAS pro-apoptotic signaling. In contrast, the ALDEFLUOR-negative bulk cell population does not express CXCR1 but is sensitive to FAS-ligand mediated cell death.

FAS-ligand/FAS signaling plays an important role during mammary gland involution (Song et al. J Clin. Invest 106:1209-1220, herein incorporated by reference in its entirety). The effect of CXCR1 blockade on human normal mammary epithelial cells obtained from reduction mammoplasties was examined. As observed in breast cancer cell lines, CXCR1-positive normal mammary cells were almost exclusively contained within the ALDEFLUOR-positive population (SEE FIG. 19A). To determine whether IL-8 signaling is important in normal breast stem/progenitor function, normal mammary epithelial cells cultured in suspension were treated with human recombinant IL-8 and determined its effect on the CSC population as measured by the formation of mammospheres (Dontu et al. Genes Dev. 17:1253-1270, herein incorporated by reference in its entirety). Addition of IL-8 increased the formation of primary and secondary mammospheres in a dose-dependent manner (SEE FIG. 19B), suggesting that the IL-8/CXCR1 axis may be involved in the regulation of normal mammary stem/progenitor cells proliferation or self-renewal. Treatment with repertaxin or the FAS agonist had no effect on the viability of normal mammary epithelial cells cultured in adherent conditions, even when high concentrations of repertaxin (500 nM) were utilized (SEE FIG. 16A). However, as observed for breast cancer cell lines, an increase of soluble FAS-ligand was detected in the medium of normal mammary epithelial cells treated with repertaxin (SEE FIG. 20B). This observation may be explained by the absence of FAS expression in the normal epithelial cells cultured under these conditions (SEE FIG. 20C). This is consistent with studies that demonstrate that expression of FAS in the mammary gland occurs only during the involution process following lactation (Song et al. J Clin. Invest 106:1209-1220, herein incorporated by reference in its entirety). In contrast to its lack of effect on the bulk population of normal mammary epithelial cells, repertaxin significantly decreased mammosphere formation by these cells (SEE FIG. 20C).

These results suggest that the IL-8/CXCR1 axis plays an important role in the regulation and the survival of normal and malignant mammary epithelial stem/progenitor cell populations. The ability to affect bulk cell populations via a FAS-ligand mediated bystander effect may relate to the level of FAS expression in these cells.

CXCR1 Blockade Effects on Cancer Stem Cells are Mediated by the FAK/AKT/FOXO3A Pathway.

CXCR1 acts through a signal transduction pathway involving the phosphorylation of the focal adhesion kinase (FAK) resulting in activation of AKT (Waugh et al. Clin. Cancer Res. 14:6735-6741., herein incorporated by reference in its entirety). To evaluate the impact of CXCR1 blockade on the FAK and AKT activation the level of FAK and AKT phosphorylated proteins was measured by western blot for the three different cell lines. For SUM159 and HCC1954, we detected a decrease in FAK $Tyr^{397}$ and AKT $Ser^{473}$ phosphorylation in cells treated with repertaxin compared to untreated cells suggesting that repertaxin effects may be mediated by the FAK/AKT pathway (SEE FIGS. 21A and 22). The observation that MDA-MB453 is resistant to repertaxin treatment may be explained by the presence of a PTEN mutation (919G>A) that activates the PI3K/AKT pathway (Hollestelle et al. Mol. Cancer Res. 5:195-201., herein incorporated by reference in its entirety). No modification in FAK $Tyr^{397}$ and AKT $Ser^{473}$ phosphorylation was detected after repertaxin treatment in MDAMB453 cell line (SEE FIG. 22). To confirm a functional role of the FAK/AKT pathway in mediating the effects of the CXCR1 blockade, two viral constructs were used, one knocking down PTEN expression via a PTEN shRNA and the other leading to FAK overexpression. PTEN, through its lipid phosphatase antagonizes PI3-K/AKT signaling (Vivanco et al. Nat. Rev. Cancer 2:489-501., herein incorporated by reference in its entirety). PTEN knockdown resulted in AKT activation as demonstrated by an increase of AKT $Ser^{473}$ phosphorylation (SEE FIGS. 21A and 22). PTEN knockdown blocked the effect of repertaxin treatment on FAK and AKT activity. FAK overexpression also blocked the effects of repertaxin and induced an activation of FAK and AKT, measured by increased expression of FAK $Tyr^{397}$ and AKT $Ser^{473}$ phosphorylation. These results indicate that CXCR1 blockade effects are mediated by FAK/AKT signaling.

Utilizing immunofluorescence staining on CXCR1-positive cells confirmed that repertaxin treatment results in a dramatic decrease of phospho-FAK and phospho-AKT expression compared to untreated cells (SEE FIG. 21B). AKT regulates the activity of the forkhead transcription factor FOXO3A via a phosphorylation event resulting in cytoplasmic FOXO3A sequestration (Brunet et al. Mol. Cell Biol. 21:952-965., herein incorporated by reference in its entirety). In contrast, the non-phosphorylated form of FOXO3A transits to the nucleus where it acts as a transcription factor that regulates the synthesis of FAS-ligand (Jonsson et al. Nat. Med. 11:666-671.), herein incorporated by reference in its entirety. Repertaxin induces cell death via a FAS-ligand mediated bystander effect; the effects of repertaxin on this signal transduction pathway were examined by immunofluorescence staining FOXO3A was present in a cytoplasmic localization in untreated cells but shuttled to the nucleus upon repertaxin treatment (SEE FIG. 21B). This indicates that CXCR1 blockade induces FOXO3A activity through inhibition of the FAK/AKT pathway. Cells with PTEN deletion or FAK overexpression display a high level of phospho-FAK and phospho-Akt expression, detected by immunofluorescence, in both repertaxin-treated and untreated cells. Repertaxin treatment did not induce FOXO3A activation in cells with PTEN deletion or FAK overexpression, as shown by the cytoplasmic location of FOXO3A (SEE FIG. 21B).

As a consequence of the constitutive activation of the FAK/AKT pathway, cells with PTEN deletion or FAK overexpression displayed resistance to repertaxin treatment. Cells with PTEN deletion or FAK overexpression did not display any decrease in cell viability with repertaxin treatment. It has been proposed that AKT signaling plays a critical role in the biology of CSC (SEE FIGS. 21B and 22) (Dubrovska et al. Proc. Natl. Acad. Sci. U.SA 106:268-273., Korkaya et al. PLoS Biolog. 7:e1000121., Yilmaz et al. Nature 441:475-482., herein incorporated by reference in their entireties). Activation of the FAK/AKT pathway blocked the repertaxin effects on the CSC populations, as shown by the maintenance of the ALDEFLUOR-positive populations after treatment with the inhibitor (SEE FIG. 21B). All the results indicate CXCR1 blockade directly affects the FAK/AKT/FOXO3A pathway. Repertaxin treatment inhibits AKT signaling which is crucial for CSC activity and subsequently induces a bystander effect on the bulk tumor cells mediated by CSC-generated FAS-ligand.

Repertaxin Treatment Reduces the Breast Cancer Stem Cell Population In Vivo.

Recent evidence suggests that breast CSC are relatively resistant to chemotherapy and radiation and may contribute to tumor regrowth following therapy (Phillips et al. J Natl. Cancer Inst. 98:1777-1785., Yu et al. Cell 131:1109-1123., Li et al. J Natl. Cancer Inst. 100:672-679., herein incorporated by reference in their entireties). The CSC concept suggests that significant improvements in clinical outcome will require effective targeting of the CSC population (Reya et al. Nature 414:105-111., herein incorporated by reference in its entirety). Several factors are synthesized and secreted during the apoptotic process when the bulk tumor cells are targeted by chemotherapy. Among these factors, FAS-ligand amplifies chemotherapy effects by mediating a bystander killing effect (Chhipa et al. J Cell Biochem. 101:68-79. herein incorporated by reference in its entirety). Chemotherapy may also induce IL-8 production in injured cells. The commonly utilized chemotherapeutic agent, docetaxel, induced both IL-8 and FAS-ligand mRNA in SUM159 cells (SEE FIG. 10a/B). We also detected a 4-fold increase of IL-8 mRNA level after FAS agonist treatment (SEE FIG. 10B). We have shown that IL-8 is able to regulate the CSC population. This indicates that the addition of repertaxin to cytotoxic chemotherapy may block this effect and target the cancer stem cell population.

The SUM159 cell line and three primary human breast cancer xenografts generated from three different patients (MC1, UM2, UM3) were used to explore the efficiency of repertaxin treatment on tumor growth. Cells from these tumors were transplanted orthotopically into the humanized cleared fat-pad of NOD/SCID mice, without cultivation in vitro. For each of these xenotransplants the CSC population was exclusively contained within the ALDEFLUOR-positive population (Ginestier et al. Cell Stem Cell 1:555-567., Charafe-Jauffret et al. Cancer Res. 69:1302-1313., herein incorporated by reference in their entireties). In each of the tumors, the CXCR1-positive population was almost exclusively contained within this ALDEFLUOR-positive population (SEE Table 5) and the PTEN/FAK/AKT pathway is activated (SEE FIG. 25).

TABLE 5

|  | ALDEFLUOR (%) | CXCR1 (%) | Overlap CXCR1/ ALDEFLUOR (%) |
|---|---|---|---|
| Breast cancer cell lines | | | |
| HCC1954 | 3.42 | 1.72 | 0.94 |
| MDA-MB-453 | 4.22 | 0.8 | 0.5 |
| SUM159 | 5.24 | 0.52 | 0.48 |
| Human breast cancer xenografts | | | |
| MC1 | 12.3 | 1.81 | 1.32 |
| UM2 | 8.4 | 1.23 | 0.88 |
| UM3 | 9.7 | 0.84 | 0.76 |

50,000 cells from each xenotransplant were injected into the humanized fat pad of NOD/SCID mice and monitored tumor growth. When the tumor size was approximately 4 mm, treatment was initiated with repertaxin alone (15 mg/Kg, twice a day, during 28 days), docetaxel alone (10 mg/Kg, once a week, during 4 weeks), or a combination of both drugs. Tumor growth was compared to saline injected controls. For each xenotransplant, a significant inhibition of tumor growth induced by docetaxel treatment or the combination repertaxin/docetaxel was observed (SEE FIGS. 26A and 27). Repertaxin treatment alone had a moderate impact on tumor growth. After four weeks of treatment, animals were sacrificed and the residual tumors were analyzed utilizing the ALDEFLUOR assay. Residual tumors treated with docetaxel alone contained either an unchanged or increased percent of ALDEFLUOR-positive cells compared to untreated controls (SEE FIGS. 26B and 27). In contrast, repertaxin treatment alone or in combination with docetaxel reduced the ALDEFLUOR-positive population by over 75% (SEE FIGS. 26B and 27). The results were confirmed by immunohistochemistry of ALDH1 expression in the different xenotransplants. A decrease in ALDH1-positive cells was detected in repertaxin-treated tumors compared to untreated tumors, whereas the percent of ALDH1-positive cells was unchanged or increased in tumors treated with docetaxel alone (SEE FIG. 26D).

The presence of CD44+/CD24- cells in these tumors was evaluated. Markers have previously been shown to be expressed in breast cancer stem cells (Al Hajj et al. Proc. Natl. Acad. Sci. U.SA 100:3983-3988., herein incorporated by reference in its entirety). The overlap between the CD44+/CD24- phenotype and CXCR1 expression was measured. CXCR1-positive cells were present in the CD44+/CD24- cell population and the cell population expressing CD24 or CD44-negative (SEE Table 6).

TABLE 6

| Human breast cancer xenografts | CD24-/CD44+ (%) | CXCR1 (%) | Overlap CD24-/ CD44+/CXCR1+ (%) |
|---|---|---|---|
| MC1 | 6.8 | 1.8 | 0.5 |
| UM2 | 3.7 | 1.2 | 0.3 |
| UM3 | 4.8 | 0.8 | 0.2 |

In residual tumors treated with docetaxel alone, either an unchanged or increased percent of CD44+/CD24- cells was observed, whereas repertaxin treatment alone or in combination with docetaxel resulted in a reduction of the CD44+/CD24− cell population (SEE FIG. 28).

A functional in vivo assay consisting of re-implantation of cells from treated tumors into secondary NOD/SCID mice provided a direct test assessing the tumor-initiating and self-renewal capacity of CSC remaining after treatment. Tumor cells derived from control or docetaxel-treated animals showed similar tumor regrowth at all dilutions in secondary NOD/SCID mice. In contrast, repertaxin treatment with or without docetaxel, reduced tumor growth in secondary recipients (SEE FIG. 26C). When equal numbers of cells were injected, those from repertaxin-treated animals showed a 2-5-fold reduction in tumor growth compared to cells from control or docetaxel-treated animals (SEE FIG. 26C). For each xenotransplant model, 1000 or 100 tumor cells obtained from animals treated with a combination of repertaxin and docetaxel failed to form any secondary tumors in NOD/SCID mice (SEE FIG. 26C, 27, and Table 7). These studies demonstrate that repertaxin treatment specifically targets and reduces the CSC population.

TABLE 7

| | Tumors/Injections number of cells injected | | | | | | |
|---|---|---|---|---|---|---|---|
| | 10,000 | 5,000 | 2,500 | 1,000 | 500 | 250 | 100 |
| Control | 6/6 | 2/2 | — | 8/8 | — | — | 6/8 |
| Repertaxin | 4/4 | 2/2 | 2/2 | 4/8 | 1/3 | 0/2 | 0/9 |
| Docetaxel | 2/2 | 4/4 | 2/2 | 6/6 | 3/4 | 2/3 | 8/9 |
| Repertaxin/Docetaxel | 2/2 | 3/4 | 2/2 | 1/6 | 1/4 | 0/4 | 0/9 |

Repertaxin Treatment Inhibits FAK/AKT Signaling and Activates FOXO3A In Vivo.

The expression of phospho-FAK and phospho-AKT was examined by immunohistochemistry in each of the xenotransplants after treatment. Membranous phospho-FAK expression was detected in 50% of cells from the control and docetaxel-treated tumors whereas the phospho-FAK expression was abolished in the tumors treated with repertaxin alone or in combination with docetaxel (SEE FIG. 26D). Similar results were observed for the phospho-AKT expression, with 70% of cells expressing phospho-AKT in the untreated tumors, 20% phospho-AKT-positive cells in docetaxel-treated tumors and a complete inhibition of phospho-AKT expression in the tumors treated with repertaxin alone or in combination with docetaxel (SEE FIG. 26D). Nuclear FOXO3A was detected in the cells from the tumors treated with docetaxel alone, repertaxin alone, and the combination repertaxin/docetaxel. These in vivo data are consistent with the in vitro data and confirm that repertaxin treatment inhibits FAK/AKT signaling and activates FOXO3A.

Repertaxin Treatment Reduces the Development of Systemic Metastasis.

To determine whether repertaxin reduces systemic metastasis we infected HCC1954, MDA-MB-453, and SUM159 breast cancer cell lines with a luciferase lentivirus reporter system and introduced the cells into NOD/SCID mice by intracardiac injection. A suspension of 250,000 cells for each cell line was injected and metastasis formation was monitored once per week by bioluminescent imaging. Twelve hours after intracardiac injection, mice were treated twice per day by repertaxin injection or saline for the controls. Repertaxin treatment in mice injected with HCC1954 and SUM159 cells significantly reduced metastasis formation with a lower photon flux emission in the treated compared to the untreated mice (SEE FIG. 29A/B). Histologic sections confirmed the presence of metastases at several sites in untreated animals (SEE FIG. 29D). Repertaxin treatment did not have any effect on metastasis formation in mice injected with MDA-MB-453 cells (SEE FIG. 29C). The photon flux emission and the number of animals that developed metastasis were similar in both repertaxin-treated and untreated group. This result is consistent with data that described MDA-MB-453 as a cell line resistant to repertaxin due to the presence of a PTEN mutation. These results indicate that CXCR1 blockade with agents such as repertaxin may be able to reduce metastasis which is mediated by the CSC population (Charafe-Jauffret et al. Cancer Res. 69:1302-1313., herein incorporated by reference in its entirety).

Experiments conducted during development of embodiments of the present invention indicate that cellular subcomponents with stem cell properties drive tumor growth and metastasis Visvader et al. Nat. Rev. Cancer 8:755-768., herein incorporated by reference in its entirety). By virtue of their relative resistance to current therapeutic modalities, these cells may contribute to treatment resistance and relapse (Reya et al. Nature 414:105-111., herein incorporated by reference in its entirety). The present invention provides an approach based on blocking the CXCR1 cytokine receptor, which is expressed on breast cancer stem cells, to effectively target the cancer stem cell population and to improve therapeutic outcome. Experiments conducted during development of embodiments of the present invention in a number of systems have demonstrated that cytokine networks play an important role in tumorigenesis. There is evidence that several of these cytokines may regulate stem cell behavior. IL-4 is capable of regulating self-renewal of pancreatic cancer stem cells and IL-6 of regulating cancer stem cells in colon and breast cancer (Todaro et al. Cell Stem Cell 1:389-402., Sansone et al. J Clin. Invest 117:3988-4002., herein incorporated by reference in their entireties). The role of IL-8 in mediating tumor invasion and metastasis has previously been demonstrated (Waugh & Wilson. Cancer Res. 14:6735-6741., Inoue et al. Clin. Cancer Res. 6:2104-2119., herein incorporated by reference in their entireties). In addition, IL-8 increases neural stem cell self-renewal during wound healing in the brain (Beech et al. J Neuroimmunol. 184:198-208., herein incorporated by reference in its entirety). Lung cancer stem cells were described as expressing the chemokine receptor CXCR1 (Levina et al. PLoS. ONE. 3:e3077., herein incorporated by reference in its entirety). Experiments conducted during development of embodiments of the present invention demonstrated that the CXCR1-positive population is almost exclusively contained within the ALDEFLUOR-positive population in breast cancer cell lines and primary xenografts as well as in normal mammary cells. The chemokine receptor is overexpressed in ALDEFLUOR-positive breast cancer cell populations (Charafe-Jauffret et al. Cancer Res. 69:1302-1313., herein incorporated by reference in its entirety). In breast cancers, IL-8 is produced in the tumor microenvironment by a number of cell types including inflammatory cells, vascular endothelial cells, tumor-associated fibroblasts and mesenchymal stem cells (Waugh et al. Clin. Cancer Res. 14:6735-6741., herein incorporated by reference in its entirety). Cytokine networks mediate interaction between these cell types, therefore cancer stem cells can be targeted through the blockade of the IL-8 receptor CXCR1.

Utilizing in vitro assays, it was demonstrated that CXCR1 but not CXCR2 (an alternative IL-8 receptor) blockade reduced the breast cancer stem cell population. This was followed by induction of apoptosis in the entire remaining cell population, which lacks CXCR1 expression. In addition to CXCR1 blocking antibodies, experiments performed during development of embodiments demonstrate that repertaxin, a CXCR1/2 inhibitor, induced similar effects by targeting the CXCR1-positive population. In contrast to its direct effects on the CXCR1-expressing cancer stem cell population, repertaxin had no direct effect on the bulk tumor cell population that lack CXCR1 expression. This indicates that CXCR1 blockade in CXCR1-positive cells induced cell death in CXCR1-negative cells via a bystander effect. Experiments described herein demonstrate that the FAS-ligand/FAS pathway is the mediator of this bystander killing effect. This phenomenon explains the efficacy of repertaxin treatment in inducing massive apoptosis in the entire cell population despite the fact that the CXCR1-positive population represents less than 1% of the cell population. The role of FAS-ligand was demonstrated by the effective blocking of bystander killing by anti-FAS-ligand antibody.

Experiments conducted during development of embodiments of the present invention indicate that similar cytokine interactions may occur in tumors exposed to cytotoxic chemotherapy. Chemotherapy may directly induce cellular apoptosis in differentiated tumor cells as well as inducing the production of FAS-ligand by these dying cells that in turn induces apoptosis in surrounding tumor cells via a FAS mediated bystander effect. Concomitant with the production of FAS-ligand, these injured cells also secrete increased levels of IL-8 in a process resembling mammary involution or wound healing. As is the case in the involuting mammary gland, this IL-8 may stimulate breast cancer stem cells as well as protecting them from apoptosis. This may contribute to the relative increase in cancer stem cells observed after chemotherapy in preclinical models (4) and neo-adjuvant clinical trials (5). The effects of chemotherapy on apoptosis and self-renewal pathways in tumors are shown in FIG. 30.

To determine whether CXCR1 blockade could target breast cancer stem cells in vivo, the effects of the cytotoxic agent docetaxel were compared with repertaxin on the cancer stem cell compartment and on tumor growth in NOD/SCID mice. Docetaxel is one of the most effective chemotherapeutic agents currently used to treat women with breast cancer. The cancer stem cell populations were assessed by the ALDEFLUOR assay and by serial transplantation in NOD/SCID mice. Utilizing these assays it was determined that chemotherapy treatment alone resulted in either no change or a relative increase in the cancer stem cell populations. In contrast, repertaxin treatment alone or with chemotherapy significantly reduced the cancer stem cell population. Despite the significant reduction in the tumor-initiating populations, use of repertaxin alone did not result in significant tumor shrinkage. The combination of repertaxin plus chemotherapy resulted in significant reduction in tumor size as well as in the cancer stem cell population. Combining these agents to target both cancer stem cells and bulk tumor cell populations maximizes the efficacy of these treatments.

To elucidate the mechanism of action of repertaxin, the pathways downstream from CXCR1 were analyzed. The interaction between CXCR1, FAK and AKT was confirmed. CXCR1 blockade acts specifically through FAK and AKT activation. Experiments conducted during development of embodiments of the present invention indicate that AKT activation regulates normal and malignant breast stem cell self-renewal through phosphorylation of GSK3β resulting in the activation of the WNT pathway (Korkaya et al. PLoS Biolog. 7:e1000121, herein incorporated by reference in its entirety). These results indicate why cells with PTEN knockdown are resistant to repertaxin. An additional function of AKT is the regulation of cell survival through phosphorylation of the forkhead transcription factor FOXO3A. AKT phosphorylation of FOXO3A results in its cytoplasmic sequestration. In contrast, it was demonstrated that CXCR1 blockade leads to decreased AKT activation resulting in the translocation of FOXO3A in the nucleus whence it induces a number of genes including FAS-ligand (Jonsson et al. Nat. Med. 11:666-671., herein incorporated by reference in its entirety). FAS-ligand induced via CXCR1 blockade in turn is responsible for the observed bystander killing effects (SEE FIG. 30).

In addition to its role in CXCR1 signaling, FAK mediates the interactions of cells with extracellular matrix components through integrin receptors (Waugh et al. Clin. Cancer Res. 14:6735-6741., herein incorporated by reference in its entirety). FAK signaling plays a role in regulating the self-renewal of normal and malignant mouse mammary stem cells in transgenic models (Luo et al. Cancer Res. 69:466-474., herein incorporated by reference in its entirety). FAK activation also promotes cell survival by blocking FADD and RIP-mediated apoptosis (Kurenova et al. Mol. Cell Biol. 24:4361-4371., Xu et al. J Biol. Chem. 275:30597-30604., herein incorporated by reference in their entireties). This provides an explanation for the resistance of the cancer stem cell population to the FAS/FAS-ligand induced apoptosis.

It has been demonstrated that breast cancer stem cells play an important role in tumor invasion and metastasis (Croker et al. J Cell Mol. Med. 2008, Charafe-Jauffret et al. Cancer Res. 69:1302-1313., herein incorporated by reference in their entireties). It is shown herein that IL-8 and CXCR1 also play important roles in these processes. The effects of CXCR1 blockade was analyzed utilizing repertaxin on the formation of experimental metastasis. It was demonstrated that CXCR1 blockade reduces the development of metastasis when administered subsequent to intracardiac injection of breast cancer cells.

Clinical studies utilizing repertaxin have demonstrated a lack of toxicity. Strategies aimed at interfering with cytokine regulatory loops such as IL-8 and CXCR1 represent methods to target breast cancer stem cells.

REFERENCES

The following references are herein incorporated by reference in their entireties, as if fully set forth herein.
1. Hanahan D and Weinberg R A. The hallmarks of cancer. Cell 2000; 100: 57-70.
2. Neve R M, Chin K, Fridlyand J et al. A collection of breast cancer cell lines for the study of functionally distinct cancer subtypes. Cancer Cell 2006; 10: 515-527.
3. Bonnet D and Dick J E. Human acute myeloid leukemia is organized as a hierarchy that originates from a primitive hematopoietic cell. Nat. Med. 1997; 3: 730-737.
4. Glinsky G V. Stem cell origin of death-from-cancer phenotypes of human prostate and breast cancers. Stem Cell Rev. 2007; 3: 79-93.
5. Jaiswal S, Traver D, Miyamoto T, Akashi K, Lagasse E, and Weissman I L. Expression of BCR/ABL and BCL-2 in myeloid progenitors leads to myeloid leukemias. Proc. Natl. Acad. Sci. U.S.A 2003; 100: 10002-10007.
6. Krivtsov A V, Twomey D, Feng Z et al. Transformation from committed progenitor to leukaemia stem cell initiated by MLL-AF9. Nature 2006; 442: 818-822.
7. Christgen M, Ballmaier M, Bruchhardt H, von Wasielewski R, Kreipe H, and Lehmann U. Identification of a distinct side population of cancer cells in the Cal-51 human breast carcinoma cell line. Mol. Cell Biochem. 2007; 306: 201-212.
8. Fillmore C M and Kuperwasser C. Human breast cancer cell lines contain stem-like cells that self-renew, give rise to phenotypically diverse progeny and survive chemotherapy. Breast Cancer Res. 2008; 10: R25.
9. Kondo T, Setoguchi T, and Taga T. Persistence of a small subpopulation of cancer stem-like cells in the C6 glioma cell line. Proc. Natl. Acad. Sci. U.S.A 2004; 101: 781-786.
10. Setoguchi T, Taga T, and Kondo T. Cancer stem cells persist in many cancer cell lines. Cell Cycle 2004; 3: 414-415.
11. Patrawala L, Calhoun T, Schneider-Broussard R, Zhou J, Claypool K, and Tang D G. Side population is enriched in tumorigenic, stem-like cancer cells, whereas ABCG2+ and A. Cancer Res. 2005; 65: 6207-6219.
12. Chute J P, Muramoto G G, Whitesides J et al. Inhibition of aldehyde dehydrogenase and retinoid signaling induces the expansion of human hematopoietic stem cells. Proc. Natl. Acad. Sci. U.S.A 2006; 103: 11707-11712.
13. Duester G. Families of retinoid dehydrogenases regulating vitamin A function: production of visual pigment and retinoic acid. Eur. J Biochem. 2000; 267: 4315-4324.
14. Cheung A M, Wan T S, Leung J C et al. Aldehyde dehydrogenase activity in leukemic blasts defines a subgroup of acute myeloid leukemia with adverse prognosis and superior NOD/SCID engrafting potential. Leukemia 2007; 21: 1423-1430.
15. Corti S, Locatelli F, Papadimitriou D et al. Identification of a primitive brain-derived neural stem cell population based on aldehyde dehydrogenase activity. Stem Cells 2006; 24: 975-985.
16. Pearce D J, Taussig D, Simpson C et al. Characterization of cells with a high aldehyde dehydrogenase activity from cord blood and acute myeloid leukemia samples. Stem Cells 2005; 23: 752-760.
17. Ginestier C, Hur M H, Charafe-Jauffret E et al. ALDH1 Is a Marker of Normal and Malignant Human Mammary Stem Cells and a Predictor of Poor Clinical Outcome. Cell Stem Cell 2007; 1: 555-567.
18. Dontu G, Abdallah W M, Foley J M et al. In vitro propagation and transcriptional profiling of human mammary stem/progenitor cells. Genes Dev. 2003; 17: 1253-1270.
19. Irizarry R A, Hobbs B, Collin F et al. Exploration, normalization, and summaries of high density oligonucleotide array probe level data. Biostatistics. 2003; 4: 249-264.
20. Charafe-Jauffret E, Ginestier C, Monville F et al. Gene expression profiling of breast cell lines identifies potential new basal markers. Oncogene 2006; 25: 2273-2284.
21. Finetti P, Cervera N, Charafe-Jauffret E et al. Sixteen-kinase gene expression identifies luminal breast cancers with poor prognosis. Cancer Res. 2008; 68: 767-776.
22. Eisen M B, Spellman P T, Brown P O, and Botstein D. Cluster analysis and display of genome-wide expression patterns. Proc. Natl. Acad. Sci. U.S.A 1998; 95: 14863-14868.
23. Reiner A, Yekutieli D, and Benjamini Y. Identifying differentially expressed genes using false discovery rate controlling procedures. Bioinformatics. 2003; 19: 368-375.
24. Hua J, Balagurunathan Y, Chen Y et al. Normalization benefits microarray-based classification. EURASIP. J Bioinform. Syst. Biol. 2006; 43056.
25. Ginestier C, Cervera N, Finetti P et al. Prognosis and gene expression profiling of 20q13-amplified breast cancers. Clin. Cancer Res. 2006; 12: 4533-4544.
26. Ponti D, Costa A, Zaffaroni N et al. Isolation and in vitro propagation of tumorigenic breast cancer cells with stem/progenitor cell properties. Cancer Res. 2005; 65: 5506-5511.
27. Ringe J, Strassburg S, Neumann K et al. Towards in situ tissue repair: human mesenchymal stem cells express chemokine receptors CXCR1, CXCR2 and CCR2, and migrate upon stimulation with CXCL8 but not CCL2. J Cell Biochem. 2007; 101: 135-146.
28. Hughes L, Malone C, Chumsri S, Burger A M, and McDonnell S. Characterisation of breast cancer cell lines and establishment of a novel isogenic subclone to study migration, invasion and tumourigenicity. Clin. Exp. Metastasis 2008.
29. Itoh Y, Joh T, Tanida S et al. IL-8 promotes cell proliferation and migration through metalloproteinase-cleavage proHB-EGF in human colon carcinoma cells. Cytokine 2005; 29: 275-282.
30. Gupta G P, Perk J, Acharyya S et al. ID genes mediate tumor reinitiation during breast cancer lung metastasis. Proc. Natl. Acad. Sci. U.S.A 2007; 104: 19506-19511.
31. Li F, Tiede B, Massague J, and Kang Y. Beyond tumorigenesis: cancer stem cells in metastasis. Cell Res. 2007; 17: 3-14.
32. Al Hajj M, Wicha M S, Benito-Hernandez A, Morrison S J, and Clarke M F. Prospective identification of tumorigenic breast cancer cells. Proc. Natl. Acad. Sci. U.S.A 2003; 100: 3983-3988.
33. Li C, Heidt D G, Dalerba P et al. Identification of pancreatic cancer stem cells. Cancer Res. 2007; 67: 1030-1037.
34. Ricci-Vitiani L, Lombardi D G, Pilozzi E et al. Identification and expansion of human colon-cancer-initiating cells. Nature 2007; 445: 111-115.
35. Montanaro F, Liadaki K, Schienda J, Flint A, Gussoni E, and Kunkel L M. Demystifying SP cell purification: viability, yield, and phenotype are defined by isolation parameters. Exp. Cell Res. 2004; 298: 144-154.
36. Stingl J, Eirew P, Ricketson I et al. Purification and unique properties of mammary epithelial stem cells. Nature 2006; 439: 993-997.
37. Matsui W, Huff C A, Wang Q et al. Characterization of clonogenic multiple myeloma cells. Blood 2004; 103: 2332-2336.
38. Farnie G and Clarke R B. Mammary stem cells and breast cancer—role of Notch signalling. Stem Cell Rev. 2007; 3: 169-175.
39. Krstic A, Mojsin M, and Stevanovic M. Regulation of SOX3 gene expression is driven by multiple NF-Y binding elements. Arch. Biochem. Biophys. 2007; 467: 163-173.
40. Zhu J, Zhang Y, Joe G J, Pompetti R, and Emerson S G. NF-Ya activates multiple hematopoietic stem cell (HSC) regulatory genes and promotes HSC self-renewal. Proc. Natl. Acad. Sci. U.S.A 2005; 102: 11728-11733.
41. Raffel G D, Mercher T, Shigematsu H et al. Ott1(Rbm15) has pleiotropic roles in hematopoietic development. Proc. Natl. Acad. Sci. U.S.A 2007; 104: 6001-6006.
42. Ma X, Renda M J, Wang L et al. Rbm15 modulates Notch-induced transcriptional activation and affects myeloid differentiation. Mol. Cell Biol. 2007; 27: 3056-3064.
43. Peiffer I, Eid P, Barbet R et al. A sub-population of high proliferative potential-quiescent human mesenchymal stem cells is under the reversible control of interferon alpha/beta. Leukemia 2007; 21: 714-724.
44. Villadsen R, Fridriksdottir A J, Ronnov-Jessen L et al. Evidence for a stem cell hierarchy in the adult human breast. J Cell Biol. 2007; 177: 87-101.
45. Hambardzumyan D, Becher O J, and Holland E C. Cancer stem cells and survival pathways. Cell Cycle 2008; 7.
46. Jagani Z and Khosravi-Far R. Cancer stem cells and impaired apoptosis. Adv. Exp. Med. Biol. 2008; 615: 331-344.
47. Maxwell P J, Gallagher R, Seaton A et al. HIF-1 and NF-kappaB-mediated upregulation of CXCR1 and CXCR2 expression promotes cell survival in hypoxic prostate cancer cells. Oncogene 2007; 26: 7333-7345.
48. Murphy C, McGurk M, Pettigrew J et al. Nonapical and cytoplasmic expression of interleukin-8, CXCR1, and CXCR2 correlates with cell proliferation and microvessel density in prostate cancer. Clin. Cancer Res. 2005; 11: 4117-4127.
49. Trentin L, Miorin M, Facco M et al. Multiple myeloma plasma cells show different chemokine receptor profiles at sites of disease activity. Br. J Haematol. 2007; 138: 594-602.
50. Varney M L, Johansson S L, and Singh R K. Distinct expression of CXCL8 and its receptors CXCR1 and CXCR2 and their association with vessel density and aggressiveness in malignant melanoma. Am. J Clin. Pathol. 2006; 125: 209-216.
51. Freund A, Chauveau C, Brouillet J P et al. IL-8 expression and its possible relationship with estrogen-receptor-negative status of breast cancer cells. Oncogene 2003; 22: 256-265.
52. Inoue K, Slaton J W, Eve B Y et al. Interleukin 8 expression regulates tumorigenicity and metastases in androgen-independent prostate cancer. Clin. Cancer Res. 2000; 6: 2104-2119.
53. Balbay M D, Pettaway C A, Kuniyasu H et al. Highly metastatic human prostate cancer growing within the prostate of athymic mice overexpresses vascular endothelial growth factor. Clin. Cancer Res. 1999; 5: 783-789.
54. Kim S J, Uehara H, Karashima T, Mccarty M, Shih N, and Fidler I J. Expression of interleukin-8 correlates with angiogenesis, tumorigenicity, and metastasis of human prostate cancer cells implanted orthotopically in nude mice. Neoplasia. 2001; 3: 33-42.
55. Karnoub A E, Dash A B, Vo A P et al. Mesenchymal stem cells within tumour stroma promote breast cancer metastasis. Nature 2007; 449: 557-563.
56. Schafer Z T and Brugge J S. IL-6 involvement in epithelial cancers. J Clin. Invest 2007; 117: 3660-3663.
57. Todaro M, Alea M P, Di Stefano A B et al. Colon cancer stem cells dictate tumor growth and resist cell death by production of interleukin-4 Cell Stem Cell 2007; 1: 389-402.
58. Landi S, Bottari F, Gemignani F et al. Interleukin-4 and interleukin-4 receptor polymorphisms and colorectal cancer risk. Eur. J Cancer 2007; 43: 762-768.
59. Sansone P, Storci G, Tavolari S et al. IL-6 triggers malignant features in mammospheres from human ductal breast carcinoma and normal mammary gland. J Clin. Invest 2007; 117: 3988-4002.
60. Glinsky G V, Berezovska O, and Glinskii A B. Microarray analysis identifies a death-from-cancer signature predicting therapy failure in patients with multiple types of cancer. J Clin. Invest 2005; 115: 1503-1521.
61. Golub T R, Slonim D K, Tamayo P et al. Molecular classification of cancer: class discovery and class prediction by gene expression monitoring. Science 1999; 286: 531-537.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:
1. A method of treating a human subject diagnosed with ER-negative breast cancer, comprising:
    (a) administering a pharmaceutical composition containing an effective concentration of Compound 1 to the human subject in need of said treatment, wherein Compound 1 is:

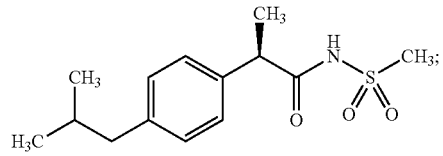

and
    (b) administering an effective concentration of paclitaxel to the subject in need of said treatment.
2. The method of claim 1 in which Compound 1 is administered at a dose between 3 and 60 mg per kg.
3. A method of treating a human subject diagnosed with metastatic ER-negative breast cancer, comprising:
    (a) administering a pharmaceutical composition containing an effective concentration of Compound 1 to the human subject in need of said treatment, wherein Compound 1 is:

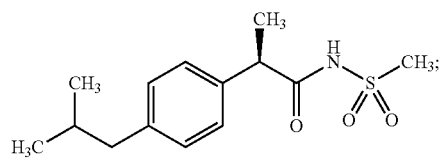

and
    (b) administering an effective concentration of paclitaxel to the human subject in need thereof.
4. The method of claim 3, in which Compound 1 is administered at a dose between 3 and 60 mg per kg.
5. The method of claim 1, wherein Compound 1 is administered concurrently with paclitaxel.
6. The method of claim 1, wherein Compound 1 is administered at a time prior to the administration of paclitaxel.

7. The method of claim 1, wherein Compound 1 is administered at a time subsequent to the administration of paclitaxel.

8. The method of claim 3, wherein Compound 1 is administered concurrently with paclitaxel.

9. The method of claim 3, wherein Compound 1 is administered at a time prior to the administration of paclitaxel.

10. The method of claim 3, wherein Compound 1 is administered at a time subsequent to the administration of paclitaxel.

11. The method of claim 3, wherein the method results in a reduction of metastasis.

12. The method of claim 3, wherein Compound 1 is administered orally.

* * * * *